(12) United States Patent
Thorne et al.

(10) Patent No.: US 12,016,893 B2
(45) Date of Patent: Jun. 25, 2024

(54) ONCOLYTIC VIRUSES FOR MODIFIED MHC EXPRESSION

(71) Applicant: KaliVir Immunotherapeutics, Inc., Pittsburgh, PA (US)

(72) Inventors: Stephen Howard Thorne, Pittsburgh, PA (US); Mingrui Zhang, Pittsburgh, PA (US)

(73) Assignee: KaliVir Immunotherapeutics, Inc., Pittsburgh, PA (US)

( * ) Notice: Subject to any disclaimer, the term of this patent is extended or adjusted under 35 U.S.C. 154(b) by 0 days.

(21) Appl. No.: 18/080,253

(22) Filed: Dec. 13, 2022

(65) Prior Publication Data

US 2023/0263846 A1 Aug. 24, 2023

Related U.S. Application Data

(63) Continuation of application No. PCT/US2022/026703, filed on Apr. 28, 2022.

(60) Provisional application No. 63/182,243, filed on Apr. 30, 2021.

(51) Int. Cl.
| | |
|---|---|
| A61K 35/768 | (2015.01) |
| A61K 45/06 | (2006.01) |
| A61P 35/00 | (2006.01) |
| C07K 14/065 | (2006.01) |
| C07K 14/47 | (2006.01) |
| C12N 15/86 | (2006.01) |

(52) U.S. Cl.
CPC ............ *A61K 35/768* (2013.01); *A61K 45/06* (2013.01); *A61P 35/00* (2018.01); *C07K 14/065* (2013.01); *C07K 14/4702* (2013.01); *C12N 15/86* (2013.01)

(58) Field of Classification Search
None
See application file for complete search history.

(56) References Cited

U.S. PATENT DOCUMENTS

| | | | |
|---|---|---|---|
| 4,458,066 A | 7/1984 | Caruthers | |
| 4,797,368 A | 1/1989 | Carter | |
| 5,139,941 A | 8/1992 | Muzyczka | |
| 5,530,020 A | 6/1996 | Gunawardana | |
| 5,543,158 A | 8/1996 | Gref | |
| 5,912,264 A | 6/1999 | Wittman | |
| 6,194,388 B1 | 2/2001 | Krieg | |
| 6,198,323 B1 | 3/2001 | Offord | |
| 6,207,646 B1 | 3/2001 | Krieg | |
| 6,352,856 B1 | 3/2002 | Falkner | |
| 6,506,559 B1 | 1/2003 | Fire | |
| 6,573,099 B2 | 6/2003 | Graham | |
| 6,579,865 B2 | 6/2003 | Mak | |
| 6,610,860 B2 | 8/2003 | Holton | |
| 6,967,023 B1 | 11/2005 | Eini | |
| 6,994,863 B2 | 2/2006 | Eini | |
| 7,105,184 B2 | 9/2006 | Pauly | |
| 7,368,122 B1 | 5/2008 | Dow | |
| 8,383,774 B2 | 2/2013 | Hill | |
| 8,536,380 B2 | 9/2013 | Scheffler | |
| 8,940,534 B2 | 1/2015 | Sandig | |
| 9,180,091 B2 | 11/2015 | Bernick | |
| 9,289,382 B2 | 3/2016 | Bernick | |
| 10,232,003 B2 | 3/2019 | Mulvey | |
| 10,238,700 B2 | 3/2019 | Szalay | |
| 10,434,136 B2 | 10/2019 | Rammensee | |
| 10,640,542 B2 | 5/2020 | Tavernier | |
| 10,647,963 B2 | 5/2020 | Hemminki | |
| 2002/0041864 A1 | 4/2002 | Fanslow, III | |
| 2002/0123099 A1 | 9/2002 | Weiner | |
| 2003/0180352 A1 | 9/2003 | Patel | |
| 2004/0143026 A1 | 7/2004 | Shah | |
| 2004/0214783 A1 | 10/2004 | Terman | |
| 2004/0248787 A1 | 12/2004 | Naito | |
| 2005/0152903 A1 | 7/2005 | Newman | |
| 2006/0099188 A1 | 5/2006 | Tagawa | |
| 2006/0111278 A1 | 5/2006 | Thim | |
| 2007/0041941 A1 | 2/2007 | Weiner | |
| 2007/0148195 A1 | 6/2007 | Ebert | |
| 2007/0178592 A1 | 8/2007 | McArthur | |
| 2007/0298054 A1 | 12/2007 | Shida | |
| 2009/0004723 A1 | 1/2009 | Kirn | |
| 2009/0208562 A1 | 8/2009 | Morein | |

(Continued)

FOREIGN PATENT DOCUMENTS

| | | |
|---|---|---|
| CN | 101381742 A | 3/2009 |
| EP | 0119621 A1 | 9/1984 |

(Continued)

OTHER PUBLICATIONS

Lin et al. Direct Priming of CD8+ T Cells Persists in the Face of Cowpox Virus Inhibitors of Antigen Presentation. Journal of Virology , May 2021. 95(10) e 00186-21. 15 pages. Originally published online Mar. 10, 2021.*
Wang et al. An Optimized HMGB1 Expressed by Recombinant Rabies Virus Enhances Immunogenicity Through Activation of Dendritic Cells in Mice. Oncotarget, 2017. 8(48): 83539-83554.*
Peritt, et al., Cutting Edge: Differentiation of Human NK Cells into NK1 and NK2 Subsets, J. Immunol., vol. 161, p. 5821-5824 (1998).
Perry et al., Clinical Scale Expansion of Human Pluripotent Stem Cells, Blood, vol. 106(11), (2005), Abstract Only.

(Continued)

*Primary Examiner* — Allison M Fox
*Assistant Examiner* — Kimberly A Aron
(74) *Attorney, Agent, or Firm* — Greenberg Traurig, LLP

(57) ABSTRACT

The present disclosure provides for recombinant oncolytic viruses with gene deletions or insertions which result in downregulation of Major Histocompatibility Complex class I and alternatively or additively upregulation of Major Histocompatibility Complex class II. Immunologic and pharmaceutical compositions comprising these recombinant viruses and methods of using these compositions are also presented.

24 Claims, 2 Drawing Sheets
Specification includes a Sequence Listing.

(56) References Cited

U.S. PATENT DOCUMENTS

| | | |
|---|---|---|
| 2010/0016224 A1 | 1/2010 | Bowie |
| 2010/0112001 A1 | 5/2010 | Djurup |
| 2010/0137198 A1 | 6/2010 | Eini |
| 2010/0291139 A1 | 11/2010 | Sutter |
| 2011/0053247 A1 | 3/2011 | Baker |
| 2011/0206640 A1 | 8/2011 | Bell |
| 2011/0274711 A1 | 11/2011 | Favier |
| 2012/0114612 A1 | 5/2012 | Evans |
| 2013/0183348 A1 | 7/2013 | Taniguchi |
| 2014/0162342 A1 | 6/2014 | Kirn |
| 2016/0060311 A1 | 3/2016 | Jo |
| 2016/0152678 A1 | 6/2016 | Bancel |
| 2016/0235793 A1 | 8/2016 | Thorne |
| 2017/0016028 A1 | 1/2017 | Yla-Herttuala |
| 2017/0173092 A1* | 6/2017 | Mulvey ............... A61K 35/768 |
| 2017/0368169 A1 | 12/2017 | Loew |
| 2018/0000733 A1 | 1/2018 | Chakroborty |
| 2018/0148694 A1 | 5/2018 | Shah |
| 2018/0214538 A1 | 8/2018 | Kirn |
| 2019/0054131 A1 | 2/2019 | Deng |
| 2019/0345204 A1 | 11/2019 | Carrió |
| 2020/0009203 A1 | 1/2020 | Sobol |
| 2020/0140824 A1 | 5/2020 | Fernandez Santidrian |
| 2020/0268831 A1* | 8/2020 | Tobin ..................... A61P 35/00 |
| 2020/0330534 A1 | 10/2020 | Delgoffe |
| 2020/0330596 A1 | 10/2020 | Borriello |
| 2021/0093684 A1 | 4/2021 | Thorne |
| 2022/0125865 A1 | 4/2022 | Thorne |

FOREIGN PATENT DOCUMENTS

| | | | |
|---|---|---|---|
| EP | 185573 A | 6/1986 | |
| EP | 488528 A | 6/1992 | |
| EP | 0689454 B1 | 3/1994 | |
| EP | 0102703 | 3/2001 | |
| WO | 9118088 A1 | 11/1991 | |
| WO | 199309239 A1 | 5/1993 | |
| WO | 199412649 A1 | 6/1994 | |
| WO | 199426914 A1 | 11/1994 | |
| WO | 199428152 A1 | 12/1994 | |
| WO | 199428938 A1 | 12/1994 | |
| WO | 199502697 A1 | 1/1995 | |
| WO | 199622378 A1 | 7/1996 | |
| WO | 1999032619 A1 | 7/1999 | |
| WO | 2001036646 A1 | 5/2001 | |
| WO | 200168820 A1 | 9/2001 | |
| WO | 2001068836 A1 | 9/2001 | |
| WO | 2003035683 A2 | 5/2003 | |
| WO | 2004018478 A2 | 3/2004 | |
| WO | 2008023077 A2 | 2/2008 | |
| WO | WO-2008100292 A2 * | 8/2008 | ........... A61K 31/282 |
| WO | 2008142479 A2 | 11/2008 | |
| WO | 2012089225 A1 | 7/2012 | |
| WO | 2015027163 A1 | 2/2015 | |
| WO | 2016033555 A1 | 3/2016 | |
| WO | 2016061286 A1 | 4/2016 | |
| WO | 2017013419 A1 | 1/2017 | |
| WO | 2017043815 A1 | 3/2017 | |
| WO | 2017165464 A1 | 9/2017 | |
| WO | 2018057755 A1 | 3/2018 | |
| WO | 2018058258 A1 | 4/2018 | |
| WO | 2018091680 A1 | 5/2018 | |
| WO | 2019089755 A1 | 5/2019 | |
| WO | 2019148109 A1 | 8/2019 | |
| WO | 2019213452 A1 | 11/2019 | |

OTHER PUBLICATIONS

Persing et al., Taking Toll: Lipid A Mimetics as Adjuvants and Immunomodulators, Trends in Microbiology, vol. 10, No. 10, S32-S37, 2002.

Pharmaceutical Preformulation and Formulation, CRC Press LLC: Boca Raton, FL, 2004).

Pipiya et al., Hypoxia reduces adenoviral replication in cancer cells by downregulation of viral protein expression, Gene Ther 2005, vol. 12(11). pp. 911-917.

Pol et al., Preclinical Evaluation of an Oncolytic Mamba Virus Vaccine in a Simian Model. 7th International Oncolytic Viruses Meeting (Quebec City, 2013).

Prestwich et al., Immune-mediated Antitumor Activity of Reovirus is Required for Therapy and is Independent of Direct Viral Oncolysis and Replication. Clin Cancer Res, vol. 15, 04374-81 (2009).

Prestwich et al., Tumor Infection by Oncolytic Reovirus Primes Adaptive Antitumor Immunity. Clinical Cancer Research : An Official Journal of the American Association for Cancer Research, vol. 14(22), p. 7358-66 (2008).

Puhlmann et al., Vaccinia is a vector for tumor-directed gene therapy: Biodistribution of a thymidine kinase-deleted mutant, Cancer Gene Ther, vol. 7, p. 676-73, 2000.

Pulido et al., Using Virally Expressed Melanoma cDNA Libraries to Identify Tumor-associated Antigens that Cure Melanoma. Nature Biotechnology, vol. 30, p. 337-43 (2012).

Putz et al., Quantification of Antibody Responses Against Multiple Antigens of the Two Infectious Forms of Vaccinia Virus Provides a Benchmark for Smallpox Vaccination. Nat Med, vol. 12, p. 1310-5 (2006).

Rakoff-Nahoum et al. Toll-like Receptors and Cancer. Nature Reviews. Cancer, vol. 9, p. 57-63 (2009).

Reading et al., Vaccinia Virus Interleukin-18-Binding Protein Promotes Virulence by Reducing Gamma Interferon Production and Natural Killer and T-cell Activity. J Virol, vol. 77, p. 9960-8 (2003).

Rehm et al., Vaccinia Virus A35R Inhibit MHC Class II Antigen Presentation, Virology, vol. 397(1), p. 176-86, 2010.

Ricca et al., Pre-existing Immunity to Oncolytic Virus Potentiates Its Immunotherapeutic Efficacy, Mol Ther 2018, vol. 26(4), pp. 1008-1019.

Rivadeneira, et al. Oncolytic Viruses Engineered to Enforce Leptin Expression Reprogram Tumor-Infiltrating T Cell Metabolism and Promote Tumor Clearance. Immunity, vol. 51, p. 548-560. 2019.

Robins et al., Comprehensive assessment of T-cell receptor B-chain diversity in αβ T cells, Blood 2009, vol. 114(19), p. 4099-107.

Rojas J, Sampath P, Hou W, Thorne SH, Defining Effective Combinations of Immune Checkpoint Blockade and Oncolytic Virotherapy. Clin. Cancer Res., (2015), PMID: 26187615.

Roman et al., Central Leptin Action Improves Skeletal Muscle AKT, AMPK, and PGC1a Activation by Hypothalamic PI3k-Dependent Mechanism, Mol Cell Endocrinol, vol. 314(1), p. 62-9, 2010.

Rommelfanger et al., Systemic Combination Virotherapy for Melanoma with Tumor Antigen-Expressing Vesicular Stomatitis Virus and Adoptive T-Cell Transfer. Cancer Research, p. 2753-4764 (2012).

Roper et al., Characterization of the Vaccinia Vrius A35R Protein and its Role in Virulence, J of Virology, vol. 80, No. 1, p. 306-313, 2006.

Rosenberg et al., Cancer Immunotherapy: Moving Beyond Current Vaccines. Nat Med, vol. 10, p. 909-15 (2004).

Russell et al., Oncolytic Viruses as Antigen-Agnostic Cancer Vaccines, Cancer Cell 2018, vol. 33(4), pp. 599-605.

Saikh, et al., Toll-Like Receptor and Cytokine Expression Patterns of CD56+ T Cells are Similar to Natural Killer Cells in Response to Infection with Venezuelan Equine Encephalitis Virus Replicons, J. Infect. Dis., vol. 188, p. 1562-1570, 2003.

Sakamoto, et al., Characteristics of T-cell Receptor Va24JaQ T Cells, a Human Counterpart of Murine NK1+ T Cells, from Normal Subjects, J. Allergy Clin. Immunol., vol. 103, S445-S451, 1999.

Sambrook et al. (ed.), Molecular Cloning: A Laboratory Manual 2nd ed., vol. 1-3, Cold Spring Harbor Laboratory Press, Cold Spring, Harbor, N.Y., 1989.

Sampath et al., Crosstalk Between Immune Cell and Oncolytic Vaccinia Therapy Enhances Tumor Trafficking and Antitumor Effects, Molecular Ther., vol. 21, No. 3, p. 620-628, 2013.

Sampath P, et al., Arming viruses in multi-mechanistic oncolytic viral therapy: current research and future developments, with emphasis on poxviruses. Oncolytic Virotherapy, vol. 3, p. 1-9, 2013.

(56) References Cited

OTHER PUBLICATIONS

Sampath P, et al., Novel therapeutic strategies in human malignancy: Combining immunotherapy and oncolytic virotherapy. Oncolytic Virotherapy, vol. 4, p. 75-82, (2015).
Samuelsson et al., Survival of Lethal Poxvirus Infection in Mice Depends on TLR9, and Therapeutic Vaccination Provides Protection. J Clin Invest, vol. 118, p. 1776-84 (2008).
Santos-Alvarez et al., Human Leptin Stimulates Proliferation and Activation of Human Circulating Monocytes, Cell Immunol, vol. 194, p. 6-11, 1999.
Sasaki et al., Regulation of DNA-raised Immune Responses by Cotransfected Interferon Regulatory Factors. Journal of Virology, vol. 76, 6652-9 (2002).
Satija et al., Spatial reconstruction of single-cell gene expression, Nat Biotechnol 2015, vol. 33(5), pp. 495-502.
Sato et al., Toll/IL-1 Receptor Domain-Containing Adaptor Inducing IFN-B (TRIF) Associates . . . in the Toll-Like Receptor Signaling1, Journal of Immunology, vol. 171, p. 4304-10 (2003).
Sautes-Fridman et al., Tumor Microenvironment is Multifaceted. Cancer Metastasis Reviews, vol. 30, vol. 13-25, 2011.
Schafer et al., Vaccinia virus-mediated intra-tumoral expression of matrix metalloproteinase 9 enhances oncolysis of PC-3 xenograft tumors, BMC Cancer, 2012, vol. 12, No. 366, p. 1-9.
Scharping et al., Efficacy of PD-1 Blockade is Potentiated by Metformin-induced Reduction of Tumor Hypoxia, Cancer Immunol. Res., vol. 5, p. 9-16, 2017.
Scharping et al., The Tumor Microenvironment Represses T Cell Mitochondrial Biogenesis to Drive Intratumoral T Cell Metabolic Insufficiency and DysfunctionImmunity 2016; vol. 45(3), p. 374-388, 2016.
Schmidt, Amgen Spikes Interest in Live Virus Vaccines for Hard-to-Treat Cancers. Nature Biotechnology, vol. 29, p. 295-6 (2011).
Senzer et al., Phase II Clinical Trial of a Granulocyte-Macrophage Colony-stimulating Factor-encoding, Second-generation Oncolytic Herpesvirus in Patients with Unresectable Metastatic Melanoma. J Clin Oncol, vol. 27, p. 5763-71 (2009).
Setoguchi et al., Homeostatic Maintenance of Natural Foxp3(+) CD25(+) CD4(+) Regulatory T Cells by Interleukin (IL)-2 and Induction of Autoimmune Disease by IL-2 Neutralization. The Journal of Experimental Medicine, vol. 201, 0723-35 (2005).
Shao L et al., (2019) IRF1 Inhibits Antitumor Immunity through the Upregulation of PD-L1 in the Tumor Cell. Cancer Immunol Res., vol. 7, Issue 8:1258-1266.
Sharma et al., The PTEN Pathway in Tregs is a Critical Driver of the Suppressive Tumor Microenvironment, Sci. Advance, p. 1-15, 2015.
Sharma et al., Primary, Adaptive, and Acquired Resistance to Cancer Immunotherapy, Cell, vol. 168(4), p. 707-23, 2017.
Sibelius et al., Role of Listeria Monocytogenes Exotoxins Listeriolysin and Phosphatidylinositol-Specific Phospholipase C in Activation of Human Neutrophils, Infection Immunity, vol. 67, p. 1125-1130, 1999.
Sidobre, et al., The T Cell Antigen Receptor Expressed by Va14i NKT Cells has a Unique Mode of Glycosphingolipid Antigen Recognition, Proc. Natl. Acad. Sci., vol. 101, p. 12254-12259, 2004.
Silva et al., Aldehyde Dehydrogenase in Combination with CD 133 Defines Angiogenic Ovarian Cancer Stem Cells that Portend Poor Patient Survival. Cancer Research, vol. 71, p. 3991-4001 (2011).
Siveen et al., Targeting the STAT3 Signaling Pathway in Cancer: Role of Synthetic and Natural Inhibitors, Biochimica et Biophysica Acta, vol. 1845, p. 136-154 (2014).
Smith et al., Comparison of Biosequences, Adv. Appl. Math., vol. 2, p. 482-489, 1981.
Smith et al., Immune Modulation by Proteins Secreted from Cells Infected by Vaccinia Virus. Arch Virol, Suppl 15, p. 111-29 (1999).
International Search Report and Written Opinion for PCT/US2018/058456, dated Feb. 5, 2019.
International Search Report and Written Opinion for PCT/US2020/012611, dated Apr. 20, 2020.
International Search Report and Written Opinion for PCT/US2020/056107, dated Mar. 1, 2021.
International Search Report and Written Opinion for PCT/US2020/056130, dated Feb. 8, 2021.
International Search Report and Written Opinion for PCT/US2021/059887, dated Feb. 2, 2022.
International Search Report and Written Opinion for PCT/US2022/026703, dated Oct. 5, 2022.
International Search Report for PCT/US2017/042910, dated Mar. 6, 2018.
International Search Report for PCT/US2017/052746, dated Feb. 13, 2018.
International Search Report for PCT/US2019/015434, dated Apr. 5, 2019.
International Search Report for PCT/US2019/062643, dated Mar. 31, 2020.
Smith et al., Infectious Poxvirus Vectors have Capacity for at Least 25 000 Base Pairs of Foreign DNA. Gene, vol. 25, p. 21-28 (1983).
Smith et al., Intracellular Cytokine Staining and Flow Cytometry: Considerations for Application in Clinical Trials of Novel Tuberculosis Vaccines, PLoS One (2015), vol. 10(9), e0138042.
Smith et al., Nonstochastic Coexpression of Activation Receptors on Murine Natural Killer Cells, J. Exp. Med., vol. 191, p. 1341-1354, (2000).
Smith G.L., et al., Vaccinia virus immune evasion. Immunol Rev, vol. 159, p. 137-154 (1997).
Sukumar et al., Mitochondrial Membrane Potential Identifies Cells with Enhanced Stemness for Cellular Therapy, Cell Metab, vol. 23(1), p. 63-76, 2016.
Sunderkotter, et al., Subpopulations of Mouse Blood Monocytes Differ in Maturation Stage and Inflammatory Response, J. Immunol., vol. 172, p. 4410-4417, 2004.
Sutter et al., A Recombinant Vector Derived from the Host Range-restricted and Highly Attenuated MVA Strain of Vaccinia Virus Stimulates Protective Immunity in Mice to Influenza Virus, Vaccine, vol. 12, No. 11, p. 1032-1040, 1994.
Symons et al., The vaccinia virus C 12L protein inhibits mouse IL-18 and promotes virus virulence in the murine intranasal model. J Gen Virol 83, 2833-2844 (2002).
Symons et al., Vaccinia Virus Encodes a Soluble Type I Interferon Receptor of Novel Structure and Broad Species Specificity, Cell., vol. 81(4), p. 551-60, 1995.
Takeshita et al., Toll-like Receptor Adaptor Molecules Enhance DNA-raised Adaptive Immune Responses Against Influenza and Tumors Through Activation of Innate Immunity. Journal of Virology, vol. 80, p. 6218-6224, 2006.
Tang et al., Endogenous HMGB1 regulates autophagy, J Cell Biol, vol. 190, No. 5, p. 881-892.
Taniguchi et al., The Regulatory Role of Va14 NKT Cells in Innate and Acquired Immune Response, Annu. Rev. Immunol., vol. 21, p. 483-513, 2003.
Terajima et al., Role of Indoleamine 2,3-Dioxygenase in Antiviral Activity of Interferon-gamma Against Vaccinia Virus. Viral Immunology, vol. 18, 722-9 (2005).
Thorne et al., Rational strain selection and engineering creates a broad-spectrum, systemically effective oncolytic poxvirus, JX-963. J Clin Invest, vol. 117, p. 3350-3358 (2007).
Thorne et al., Targeted and Armed Oncolytic Poxviruses: A Novel Multi-mechanistic Therapeutic Class for Cancer, Nat Rev Cancer, vol. 9, p. 64-71, 2009.
Thorne et al., Targeting localized immune suppression within the tumor through repeat cycles of immune cell-oncolytic virus combination therapy. Molecular Therapy : The Journal of the American Society of Gene Therapy, vol. 18, p. 1698-705 (2010).
Thorne SH, Design and testing of novel oncolytic vaccinia strains. Methods Mol Biol., Gene Therapy of Cancer, vol. 542, p. 635-647, 2009.
Thorne, Enhancing Biological Therapy through Conditional Regulation of Protein Stability. Expert Reviews in Molecular Medicine, vol. 12, e2 (2010).
Thorne, Immunotherapeutic Potential of Oncolytic Vaccinia Virus. Immunologic Research, vol. 50, p. 286-93 (2011).

(56) References Cited

OTHER PUBLICATIONS

Thorne, S. H. "Immunotherapeutic potential of oncolytic vaccinia virus," Frontiers in Oncology, Jun. 17, 2014, vol. 4, No. 155, pp. 1-5.
Thorne, Virus fuels NK cell killing of leukemia, 2016, Blood, vol. 127, Issue21, 2509.
Torres et al., Toll-Like Receptor 2 is Required for Optimal Control of Listeria monocytogenes Infection, Infection and Immunity, vol. 72, p. 2131-2139, 2004.
Tosic et al., Myxoma Virus Expressing a Fusion Protein of Interleukin-15 (IL15) and IL15 Receptor Alpha has Enhanced Antitumor Activity, PLOS One, 2014, vol. 9, No. 10, p. 3109801.
Trumpfheller et al., The microbial mimic poly IC induces durable and protective CD4+ T cell immunity together with a dendritic cell targeted vaccine. Proceedings of the National Academy of Sciences of the United States of America, vol. 105, p. 2574-9 (2008).
Tsukamoto et al., Expression of the int-I gene in transgenic mice is associated with mammary gland hyperplasia and adenocarcinomas in male and female mice. Cell, vol. 55, p. 619-625, 1988.
Tuschl T. et al., Targeted mRNA degradation by double-stranded RNA in vitro, Genes & Development, vol. 13, p. 3191-3197, 1999.
Tvinnereim et al., Neutrophil Involvement in Cross-Priming CD8+ T Cell Responses to Bacterial Antigens, J. Immunol., vol. 17. p. 1994-2002, 2004.
Umemura et al. Defective NF-kappaB signaling in metastatic head and neck cancer cells leads to enhanced apoptosis by double-stranded RNA. Cancer Research, vol. 72, p. 45-55 (2012).
Van Der Windt et al., CD8 memory T cells have a bioenergetic advantage that underlies their rapid recall ability, PNAS, vol. 110(35), p. 14336-41, 2013.
Van Der Windt et al., Mitochondrial Respiratory Capacity Is a Critical Regulator Of CD8+ T Cell Memory Development, Immunity, vol. 36(1), p. 68-78, 2012.
Van Eijl et al., The Vaccinia Virus A36R Protein Is a Type Ib Membrane Protein Present on Intracellular but Not Extracellular Enveloped Virus Particles, Virology, vol. 271, p. 26-36, 2000.
Vella et al., Healthy individuals have T-cell and antibody responses to the tumor antigen cyclin BI that when elicited In mice protect from cancer. Proceedings of the National Academy of Sciences of the United States of America, vol. 106, p. 14010-5 (2009).
Visus et al., Targeting ALDH (bright) human carcinoma-initiating cells with ALDHIAI-specific CDS(+) T cells. Clinical Cancer Research : An Official Journal of the American Association for Cancer Research, vol. 17, p. 6174-84 (2011).
Von Beust, In vivo priming of bovine T lymphocytes with vaccinia viruses expresssing the bovine leukemia virus envelope gene together with bovine interleukin-4 or bovine interleukin-12, Washington State University, 1997, pp. 1-18.
Walzer et al., Differential In Vivo Persistence of Two Subsets of Memory Phenotype CD8 T Cells Defined by CD44 and CD122 Expression Levels, J. Immunol., vol. 168, p. 2704-2711, 2002.
Wang et al., Treating Tumors With a Vaccinia Virus Expressing IFNbeta Illustrates the Complex Relationships Between Oncolytic Ability and Immunogenicity. Molecular Therapy : The Journal of the American Society of Gene Therapy, vol. 20, No. 4, p. 736-748, (2012).
Weber et al., antiSMASH 3.0—a comprehensive resource for the genome mining of biosynthetic gene clusters, Nucleic Acids Research, vol. 43, W237-W243, 2015.
Wei et al., Interleukin-2 administration alters the CD4+FOXP3+ T-cell pool and tumor trafficking in patients with ovarian carcinoma. Cancer Research, vol. 67, p. 7487-94 (2007).
Weiss et al., Trafficking of high avidity HER-2/neu-specific T cells into HER-2/neu-expressing tumors after depletion of effector/memory-like regulatory T cells. PLoS One 7, vol. 7, e31962 (2012).
Wesa et al., Polarized type-I dendritic cells (DCI) producing high levels of IL-12 family members rescue patient THI-type antimelanoma CD4+ T cell responses in vitro. J Immunother, vol. 30, p. 75-82 (2007).

Whitman et al., In vitro and in vivo kinetics of recombinant vaccinia virus cancer-gene therapy. Surgery. Surgery 1994; vol. 116(2), p. 183-8.
Wong et al., Helper Activity of Natural Killer Cells During the Dendritic Cell-mediated Induction of Melanoma-specific Cytotoxic T Cells. Journal of Immunotherapy, vol. 34, 270-8 (2011).
Workenhe et al., Mitoxantrone synergizes with oncolytic herpes simplex virus to regress established breast tumors In part by increasing recruitment of CDS+ T cells. 7th International Oncolytic Viruses Meeting (Quebec City, 2013).
Worschech A., et al., Systemic treatment of xenografts with vaccinia virus GLV-I h68 reveals the immunologic facet of oncolytic therapy. BMC Genomics vol. 10, 301 (2009).
Yan et al., (2012) High mobility group box 1 activates caspase-1 and promotes hepatocellular carcinoma invasiveness and metastases. Hepatology. Jan. 1, 20121, vol. 55, Issue 6, pp. 1863-1875.
Yang et al., Mechanisms of Monophosphoryl Lipid A Augmentation of Host Responses to Recombinant HagB from Porphyromonas gingivalis, Infection and Immunity, Jul. 2002, p. 3557-3565.
Yang et al., Persistent Toll-like receptor signals are required for reversal of regulatory T cell-mediated CD8 tolerance. Nature Immunology, vol. 5, p. 508-15 (2004).
Yu et al., Visualization of tumors and metastases in live animals with bacteria and vaccinia virus encoding light-emitting proteins. Nat Biotechnol, vol. 22, p. 313-20 (2004).
Yue et al., Targeting STAT3 in cancer: how successful are we? Expert Opin. Investig. Drugs, vol. 18(1), p. 45-56 (2009).
Zamarin et al., Intratumoral modulation of the inducible co-stimulator ICOS by recombinant oncolytic virus promotes systemic anti-tumour immunity, Nature Communication, 2017; 8: p. 1-14.
Albarnaz, Modulating Vaccinia Virus Immunomodulators to Improve Immunological Memory, Viruses, 2018, vol. 10, p. 1-33.
Albelda SM, et al., (2014) Giving Oncolytic Vaccinia Virus More BiTE. Mol Ther., vol. 22(1), p. 6-8.
Alcami et al., A Soluble Receptor for Interleukin-1B Encoded by Vaccinia Virus: A Novel Mechanism of Virus Modulation of the Host Response to Infection, 1992, Cell. 71(1), p. 153-67.
Alferink et al., Compartmentalized Production of CCL17 In Vivo . . . (2003) J. Exp. Med. 197, p. 585-599.
Myers and Miller, Approximate matching of regular expressions, Bulletin of Mathematical Biology, vol. 51, Issue 1, p. 5-37; (1989).
Altschul et al., Basic Local Alignment Search Tool, J. Mol. Biol., 1990, vol. 215, p. 403-410.
Altschul et al., Issues in Searching Molecular Sequence Databases, Nature Genet., vol. 6, p. 119-129, 1994.
Altschul, S. et al., Gapped BLAST and PSI-BLAST: a new generation of protein database search programs, Nucleic Acids Res., vol. 25, p. 3389-3402 (1997).
Alvarez-Breckenridge et al., NK Cells Impede Glioblastoma Virotherapy Through NKp30 and NKp46 Natural Cytotoxicity Receptors. Nature Medicine, vol. 18, p. 1827-34 (2012).
Andre et al., Hyal2 is a glycosylphosphatidylinositol-anchored, lipid raft-associated hyaluronidase, Biochemical and Biophysical Research Communications, 2011, vol. 411, p. 175-179.
Andtbacka et al., Talimogene Laherparepvec Improves Durable Response Rate in Patients with Advanced Melanoma.J Clin Oncol 2015; vol. 33(25), p. 2780-8.
Arming et al., In vitro mutagenesis of PH-20 hyaluronidase from human sperm, Eur. J. Biochem, 199, vol. 247, p. 810-814.
Bahar et al., Structure and Function of A41, a Vaccinia Virus Chemokine Binding Protein. PLoS Pathog 4, e5 (2008).
Baldrick et al., Safety Evaluation of a New Allergy Vaccine Containing the Adjuvant Monophosphoryl Lipid A (MPL) for the Treatment of Grass Pollen Allergy, Journal of Applied Toxicology, vol. 24, p. 261-268, 2004.
Baldrick et al., Safety Evaluation of Monophosphoryl Lipid A (MPL): An Immunostimulatory Adjuvant, Reg. Toxi. and Pharma., vol. 35, p. 398-413, 2002.
Baldridge, et al., Monophosphoryl lipid A enhances mucosal and systemic immunity to vaccine antigens following intranasal administration. Elsevier, Vaccine, 2000, vol. 18, p. 2416-2425.
Banaszynski et al., Chemical control of protein stability and function in living mice. Nat Med, vol. 14(10), p. 1123-127, 2008.

(56) References Cited

OTHER PUBLICATIONS

Banchereau et al., Dendritic cells as therapeutic vaccines against cancer. Nat Rev Immunol, vol. 5, 296-306 (2005).
Barve et al., Induction of Immune Responses and Clinical Efficacy in a Phase II Trial of IDM-2101, a 10-Epitope Cytotoxic T-Lymphocyte Vaccine, in Metastatic Non-Small-Cell Lung Cancer, J Clin Oncol 2008; vol. 26(27), p. 4418-25.
Beard et al., Transcription Mapping of Mouse Adenovirus Type 1 Early Region 3, Virology, 1990, 175, p. 81-90.
Beaucage & Caruthers, Deoxynucleoside Phosphoramidites—A New Class of Key Intermediates for Deoxypolynucleotide Synthesis, Tetra. Letts. 22(20):1859-1862, 1981.
Becker, Immunological and Regulatory Functions of Uninfected and Virus Infected Immature and Mature Subtypes of Dendritic Cells—a Review, Virus Genes, 2003, vol. 26, p. 119-130.
Belyakov, et al., What Role does the Route of Immunization Play in the Generation of Protective Immunity Against Mucosal Pathogens? Journal of Immunology, vol. 183, p. 6883-92 (2009).
Bernard, et al. Chronic Inhibition of Cyclooxygenase-2 Attenuates Antibody Responses Against Vaccinia Infection. Vaccine, vol. 28, p. 1363-72 (2010).
Binz et al., Chemovirotherapy: Combining chemotherapeutic treatment with oncolytic virotherapy, Oncolytic Virotherapy, 2015, vol. 4, p. 39-48.
Bischoff, et al., An Adenovirus Mutant that Replicates selectively in p53-Deficient Human Tumor Cells. Science, vol. 274, p. 373-6 (1996).
Bitter et al., Expression and Secretion Vectors for Yeast, Methods in Enzymology, vol. 153, p. 516-544, 1987.
Blasco el al., Dissociation of progeny vaccinia virus from the cell membrane is regulated by a viral envelope glycoprotein: effect of a point mutation in the lectin homology domain of the A34R gene, American Society for Microbiology Journals, Jun. 1, 1993, vol. 67, Iss. 6, pp. 3319-3325.
Boonstra, et al., Flexibility of mouse classical and plasmacytoid-derived dendritic cells in directing T helper type 1 and 2 cell development: dependency on antigen dose and differential toll-like receptor ligation, J. Exp. Med., vol. 197, p. 101-109, 2003.
Brader, et al., Imaging of Lymph Node Micrometastases using an Oncolytic Herpes Virus and [18F]FEAU PET. PLoS One, vol. 4, e4789 (2009).
Breitbach, et al., Intravenous Delivery of a Multi-Mechanistic Cancer-Targeted Oncolytic Poxvirus in Humans. Nature, vol. 477, p. 99-102 (2011).
Brown et al., "The p14 FAST Protein of Reptilian Reovirus Increases Vesicular Stomatitis Virus Neuropathogenesis", Journal of Virology, 2009, vol. 83, No. 2, p. 552-561.
Brown et al., Cancer Immunotherapy with Recombinant Poliovirus Induces IFN-Dominant Activation of Dendritic Cells and Tumor Antigen-Specific CTLs; Sci Trans Med. 2017; vol. 9, No. 408, pp. 1-37.
Brown, et al., Chemical Synthesis and Cloning of a Tyrosine tRNA Gene, Meth. Enzymol., vol. 68, p. 109-151, 1979.
Brummelkamp et al., Stable Suppression of Tumorigenicity by Virus-Mediated RNA Interference, Cancer Cell, vol. 2, p. 243-247 (2002).
Brzoza, et al., Cytoplasmic Entry of Listeria Monocytogenes Enhances Dendritic Cell Maturation and T Cell Differentiation and Function, J. Immunol., vol. 173, p. 2641-2651.
Bu et al., GRIM-19 Inhibits the STAT3 Signaling Pathway and Sensitizes Gastric Cancer Cells to Radiation, Gene, vol. 512(2), p. 198-205 (2013).
Buijs et al., Oncolytic viruses: From bench to bedside with a focus on safety, Human Vaccines & Immunotherapeutics, 2015, vol. 11(7), p. 1573-1584.
Buller et al., Decreased virulence of recombinant vaccinia virus expression vectors is associated with a thymidine kinase-negative phenotype, Nature 1985, vol. 317(6040), p. 813-5.
Buller et al., Poxvirus Pathogenesis, Microbiological Reviews, vol. 55, No. 1, Mar. 1991, p. 80-122.
Cantoni et al., Role of NK cells in immunotherapy and virotherapy of solic tumors, Immunotherapy, 2015, vol. 7, No. 8, p. 861-882.
Carine, et al., Mouse Strain Differences in Plasmacytoid Dendritic Cell Frequency and Function Revealed by a Novel Monoclonal Antibody, J. Immunol., vol. 171, p. 6466-6477, 2003.
Carpenter et al., STAT3 Target Genes Relevant to Human Cancers, Cancers, vol. 6, p. 897-925, 2014.
Carrillo et al., "Enhanced adaptation of vesicular stomatitis virus in cells infected with vaccinia virus", Infection, Genetics and Evolution, Elsevier, Amsterdam, NL, 2008, vol. 8, No. 5, pp. 614-620.
Chakir, et al., Differential of Murine NK Cells into Distinct Subsets Based on Variable Expression of the IL-12Rb2 Subunit, J. Immunol., vol. 165, p. 4985-4993, 2000.
Chakrabarti et al., Compact, Synthetic, Vaccinia Virus Early/Late Promoter for Protein Expression, Biotechniques, vol. 23, p. 1094-1097, Dec. 1997.
Chang et al., The E3L Gene of Vaccinia Virus Encodes an Inhibitor of the Interferon-Induced, Double-Stranded RNA-Dependent Protein Kinase, Proc. Natl. Acad. Sci., vol. 89(11), p. 4825-9, Jun. 1992.
Chang, et al., Treatment with Cyclooxygenase-2 Inhibitors Enables Repeated Administration of Vaccinia Virus for Control of Ovarian Cancer, Molecular Therapy, The Journal of the American Society of Gene Therapy 17, 1365-72 (2009).
Charafe, Jauffret et al., Breast Cancer Cell Lines Contain Functional Cancer Stem Cells with Metastatic Capacity and a Distinct Molecular Signature. Cancer Research, vol. 69, p. 1302-13 (2009).
Chartier et al., Efficient Generation of Recombinant Adenovirus Vectors by Homologous Recombination in *Escherichia coli*, Journal of Virology, Jul. 1996, vol. 7, No. 7, p. 4805-4810.
Zeh H, et al., First-in-man Study of Western Reserve Strain Oncolytic Vaccinia Virus: Safety, Systemic Spread and Anti-tumor Activity. Molecular Therapy, vol. 23, No. 1, Jan. 2015.
Zhang et al., Eradication of solid human breast tumors in nude mice with an intravenously injected light-emitting oncolytic vaccinia virus. Cancer Res, vol. 67, p. 10038-46 (2007).
Zhu et al., High-throughput screening for TLR3-IFN regulatory factor 3 signaling pathway modulators identifies several antipsychotic drugs as TLR inhibitors. Journal of Immunology, vol. 184, p. 5768-76 (2010).
Zhu et al., Innate immunity against vaccinia virus is mediated by TLR2 and requires TLR-independent production of IFN-B. Blood, vol. 109, p. 619-25 (2007).
Zufferey et al., Self-Inactivating Lentivirus Vector for Safe and Efficient In Vivo Gene Delivery, J. Virol., 1998, vol. 72, p. 9873-80.
Chen, et al., Cancers take Their Toll—The Function and Regulation of Toll-like Receptors in Cancer Cells. Oncogene, vol. 27, p. 225-33 (2008).
Chen, et al., Regulating Cytokine Function Enhances Safety and Activity of Genetic Cancer Therapies. Molecular Therapy : The Journal of the American Society of Gene Therapy, vol. 21, p. 167-74 (2013).
Cheng et al., Anticancer Function of Polyinosinic-Polycytidylic Acid. Cancer Biology & Therapy, vol. 10, p. 1219-23 (2011).
Chertova et al. "Characterization and Favorable in Vivo Properties of Heterodimeric Soluble IL-15/IL-15Rα Cytokine Compared to IL-15 Monomer," Journal of Biological Chemistry, May 6, 2013, vol. 288, pp. 18093-18103.
Cho, et al., Isolation and Molecular Characterization of Cancer Stem Cells in MMTV-Wnt-1 Murine Breast Tumors. Stem Cells, vol. 26, p. 364-71, 2008.
Choi et al., From benchtop to bedside: a review of oncolytic virotherapy, Biomedicines, 2016, vol. 4(3), p. 1-20.
Coffin, R. Clinical Updates with oncolytic HSV. in 7th International Oncolytic Virus Meeting (Quebec City, 2013).
Colamonici et al., Vaccinia Virus B18R Gene Encodes a Type 1 Interferon-Binding Protein that Blocks Interferon a Transmembrane Signaling, J. Biol. Chem. vol. 270(27):, p. 5974-8. 1005.
Corpet et al., Multiple Sequence Alignment with Hierarchical Clustering, Nucleic Acids Research, vol. 16, 010881-10890, 1988.
Couedel et al., Diverse CD1d-Restricted Reactivity Patterns of Human T Cells Bearing "invariant" AV24BV11 TCR, Eur. J. Immunol., vol. 28, p. 4391-4397, 1988.

(56) References Cited

OTHER PUBLICATIONS

Dankort et al., BRafV600E cooperates with Pten silencing to elicit metastatic melanoma, Nat. Genet. 2009; vol. 41, No. 5, pp. 544-552.
Davies et al., The E3L and K3L vaccinia virus gene products stimulate translation through inhibition of the double-stranded RNA-dependent protein kinase by different mechanisms, J. Virol., vol. 67(3), p. 1688-92, 1993.
Dehoon et al., Open source clustering software, Bioinformatics 2004, vol. 20(9), pp. 1453-1454.
Delgoffe et al., Enhanced interaction between Hsp90 and raptor regulates mTOR signaling upon T cell activation, Mol. Immunol. 2009; vol. 46(13), p. 2694-8.
Di Pilato M, et al., Distinct Roles of Vaccinia Virus NF-kB Inhibitor Proteins A52, B15, and K7 in the Immune Response, J Virology, vol. 91, Issue 13, e00575-17.
Doe et al., Induction of HIV-1 envelope (gp120)-specific cytotoxic T lymphocyte responses in mice by recombinant CHO cell-derived gp120 is enhanced by enzymatic removal of N-linked glycans, Eur. J. Immunol., (1994), vol. 24, p. 2369-2376.
Donnenberg, et al., Rare-Event Analysis of Circulating Human Dendritic Cell Subsets and Their Presumptive Mouse Counterparts, Transplantation, vol. 72, p. 1946-1951, 2001.
Dowty and Wolff, ed, Gene Therapeutics, Methods and Applications of Direct Gene Transfer, Birkhauser, Boston, USA (1994).
Drugs and Pharmaceutical Sciences, Pharmaceutical Preformulation and Formulation, 2nd Edition, Gibson Ed., CRC Press LLC: Boca Raton, FL, 2004.
Durham et al. "Oncolytic VSV Primes Differential Responses to Immuno-oncology Therapy," Molecular Therapy, Aug. 30, 2017 (Aug. 30, 2017), vol. 25, No. 8, pp. 1917-1932.
Earl et al., Native oligomeric human immunodeficiency virus type 1 envelope glycoprotein elicits diverse monoclonal antibody reactivities, J of Virology, vol. 68, No. 5, 1994.
Earl et al., Removal of cryptic poxvirus transcription termination signals from the human immunodeficiency virus type 1 envelope gene enhances expression and immunogenicity of a recombinant vaccinia virus, J. Virol., vol. 64, p. 2448-2451, 1990.
Ehrlich, et al., Engagement of NKG2D by cognate ligand or antibody alone is insufficient to mediate costimulation of human and mouse CD8+ T cells, J. Immunol., vol. 174, p. 1922-1931, 2005.
Eisenberg, et al., Real-time Intraoperative Detection of Breast Cancer Axillary Lymph Node Metastases using a Green Fluorescent Protein-expressing Herpes Virus. Annals of surgery, vol. 243, p. 824-30; discussion 830-2 (2006).
Elbashir, S. M. et al., RNA Interference is Mediated by 21- and 22-Nucleotide RNAs, Genes & Development, vol. 15; p. 188-200, 2001.
Emoto, et al., Transient Control of Interleukin-4-Producing Natural Killer T Cells in Liver of Listeria Monocytogenes-Infected Mice by Interleukin 12, Infection Immunity, vol. 65, p. 5003-5009, 1997.
Enzler, et al., Deficiencies of GM-CSF and Interferon Gamma Link Inflammation and Cancer. The Journal of Experimental Medicine, vol. 197, p. 1213-9 (2003).
Ercolini et al., Recruitment of Latent Pools of High-avidity CDS(+) T Cells to the Antitumor Immune Response. The Journal of Experimental Medicine, vol. 201, p. 1591-602 (2005).
Erickson et al., Hepatitis C Virus-Specific CTL Responses in the Liver of Chimpanzees with Acute and Chronic Hepatitis C, J. Immunol., vol. 151. p. 4189-4199, 1993.
Errington, F., et al., Fusogenic membrane glycoprotein-mediated tumour cell fusion activates human dendritic cells for enhanced IL-12 production and T-cell priming. Gene Therapy, vol. 13, p. 138-49 (2006).
Evans et al., Enhancement of Antigen-Specific Immunity via the TLR4 Ligands MPL Adjuvant and Ribi.529, Summary of Clinical Trials, Expert Review Vaccines, vol. 2, No. 2, 2003.
Fahy et al., Vaccinia Virus Protein C16 Acts Intracellularly to Modulate the Host Response and Promote Virulence, J. Gen. Virol., vol. 89, p. 2377-2387, 2008.
Falivene et al., Improving the MVA vaccine Potential by Deleting the Viral Gene Coding for the IL-18 Binding Protein. PLoS One 7, e32220, 2012.
Falkner et al., Transient Dominant Selection of Recombinant Vaccinia Viruses, J Virol., vol. 64(6), p. 3108-3111, 1990.
Farrell et al., Cloning, nucleotide sequence determination and expression of the *Staphylococcus aureus* hyaluronate lyase gene, FEMS Microbiology Letters, 1995, vol. 130(1), p. 81-85.
Feoktistova, et al., cIAPs Block Ripoptosome Formation, a RIPI/caspase-8 Containing Intracellular Cell Death Complex Differentially Regulated by cFLIP Isoforrns. Molecular Cell, vol. 43, p. 449-63 (2011).
Feuerer et al., Fat Treg Cells: a Liaison Between the Immune and Metabolic Systems, Nat Med, vol. 15(8), p. 930-9, 2009.
Filipazzi et al., Identification of a New Subset of Myeloid Suppressor Cells . . . Antitumor Vaccine. Journal of Clinical Oncology : Official Journal of the American Society of Clinical Oncology, vol. 25, p. 2546-53 (2007).
Fountzilas et al., Review: Oncolytic Virotherapy, Updates and Future Directions, Oncotarget, vol. 8, p. 102617-39, 2017.
Friedman et al., Hypoxia Moderates γ134.5-Deleted Herpes Simplex Virus Oncolytic Activity in Human Glioma Kenoline Primary Cultures, Transl Oncol 2012, vol. 5(3), p. 200-7.
Fujita, et al.COX-2 Blockade Suppresses Gliomagenesis by Inhibiting Myeloid-Derived Suppressor Cells. Cancer Research, vol. 71, p. 2664-74, 2011.
Fukata et al., Role of Toll-like Receptors in Gastrointestinal Malignancies. Oncogene, vol. 27, p. 234-43 (2008).
Furtek et al., Strategies and Approaches of Targeting STAT3 for Cancer Treatment, ACS Chem. Biol., vol. 11(2), p. 308-318 (2016).
Galon J. et al., Type, Density, and Location of Immune Cells within Human Colorectal Tumors Predict Clinical Outcome. Science, vol. 313, p. 1960-4 (2006).
Garber, K., China Approves World's First Oncolytic Virus Therapy for Cancer Treatment. J Natl Cancer Inst, vol. 98, p. 298-300 (2006).
Gaston et al., Production of Bioactive Soluble Interleukin-15 in Complex with Interleukin-15 Receptor Alpha from a Conditionally-Replicating Oncolytic HSV-1, PLOS One, 2013, vol. 8, No. 11, p. e81768.
Gil et al., Targeting CXCL 12/CXCR4 Signaling with Oncolytic Virotherapy Disrupts Tumor, Vasculature and Inhibits Breast Cancer Metastases, Proceedings of the National Academy of Sciences, Mar. 13, 2013, vol. 110, No. 14, pp. 1291-1300.
Ginestier, et al. CXCR1 Blockade Selectively Targets Human Breast Cancer Stem Cells in Vitro and in Xenografts. The Journal of Clinical Investigation, vol. 120, p. 485-97 (2010).
Gmachl et al., The human sperm protein PH-20 has hyaluronidase activity; FEBS Letters, 1993, vol. 336, No. 3, p. 545-548.
Gnant et al., Tumor-specific Gene Delivery using Recombinant Vaccinia Virus in a Rabbit Model of Liver Metastases. J Natl Cancer Inst, vol. 91, p. 1744-50 (1999).
Godin-Ethier, et al., Indoleamine 2,3-dioxygenase Expression in Human Cancers: Clinical and Immunologic Perspectives. Clinical Cancer Research: An Official Journal of the American Association for Cancer Research, vol. 17, p. 6985-91 (2011).
Goldufsky et al., Oncolytic virus therapy for cancer. Oncolytic Virotherapy, 2013, vol. 2, p. 31-46.
Graham et al., Characteristics of a Human Cell Line Transformed by DNA from Human Adenovirus Type 5, J. Gen. Virol., vol. 36, p. 59-72, 1977.
Graham, Covalently Closed Circles of Human Adenovirus DNA are Infectious, EMBO J., vol. 3, p. 2917, 1984.
Green, D.R. et al., Immunogenic and Tolerogenic Cell Death. Nature Reviews, Immunology, vol. 9, p. 353-63 (2009).
Guedan et al., Hyaluronidase expression by an oncolytic adenovirus enhances its intratumoral spread and suppresses tumor growth, Molecular Therapy, 2010, vol. 18(7), p. 1275-83.
Gulley, et al., Pilot Study of Vaccination with Recombinant CEA-MUC-1-TRICOM Poxviral-based Vaccines in Patients with Metastatic Carcinoma. Clin Cancer Res, vol. 14, p. 3060-9 (2008).
Guo et al., Oncolytic Immunotherapy: Conceptual Evolution, Current Strategies, and Future Perspectives, Front. Oncol., vol. 8, p. 1-15, 2017.

(56) References Cited

OTHER PUBLICATIONS

Guo et al., Oncolytic Immunotherapy: Dying the Right Way is a Key to Eliciting Potent Antitumor Immunity, Frontiers In Oncology, Apr. 10, 2014 (Apr. 10, 2014), vol. 4, No. 74, pp. 1-11.
Guo et al., Rapid Generation of Multiple Loci-Engineered Marker-free Poxvirus and Characterization of a Clinical-Grade Oncolytic Vaccinia Virus, Molecular Therapy, Methods and Clinical Development, 2017, vol. 7, p. 112-122.
Guo, et al., Oncolytic Virotherapy: Molecular Targets in Tumor-Selective Replication and Carrier Cell-mediated Delivery of Oncolytic Viruses. Biochim Biophys Acta (2008).
Guo, et al., The Enhanced Tumor Selectivity of an Oncolytic Vaccinia Lacking the Host Range and Antiapoptosis Genes SPI-1 and SPI-2. Cancer Res, vol. 65, p. 9991-8 (2005).
Guy, et al., Expression of the Neu Protooncogene in the Mammary Epithelium of Transgenic Mice Induces Metastatic Disease. Proceedings of the National Academy of Sciences of the United States of America, vol. 89, p. 10578-82 (1992).
Hannon, G J., A Conserved Biological Response to Double-stranted RNA, RNA Interference, Nature, vol. 418, p. 244-251, 2002.
Hart et al., Genotypic and phenotypic assessment of hyaluronidase among type strains of a select group of *Staphylococcal* species, International Journal of Microbiology, 2009, vol. 2009, Article 614371, p. 1-8.
Hennessy, et al., Targeting Toll-like Receptors: Emerging Therapeutics? Nature Reviews. Drug Discovery, vol. 9, p. 293-307 (2010).
Herbst et al., Predictive Correlates of Response to the Anti-PD-L1 Antibody MPDL3280A in Cancer Patients, Nature, vol. 515(7528), p. 563-567, 2014.
Higgins, et al., Clustal: a package for performing multiple sequence alignment ona microcomputer, Gene, vol. 73, p. 237-244, 1988.
Higgins, et al., Fast and Sensitive Multiple Sequence Alignments on a Microcomputer, Cabios, vol. 5, No. p. 151-153, 1989.
Hiley et al., Lister strain vaccinia virus, a potential therapeutic vector targeting hypoxic tumours, Gene Therapy, 2010, vol. 17(2), p. 281-287.
Hokey et al., Tumor Cell Loaded Type-I Polarized Dendritic Cells Induce Thl-mediated Tumor Immunity. Cancer Research, vol. 65, p. 10059-67 (2005).
Hornemann et al., Replication of Modified Vaccinia Virus Ankara . . . Inteferon Resistance Gene E3L, Journal of Virology, vol. 77, No. 15, p. 394-8407, 2003.
Hou W, et al. (2014) Oncolytic Vaccinia Virus Demonstrates Anti-angiogenic Effects Mediated by Targeting of VEGF. Int J Cancer. 2014, vol. 135, p. 1238-1246.
Hsu et al., Leptin-Induced Mitochondrial Fusioni Mediates Hepatic Lipid Accumulation, Int J Obes (Lond) 2015, vol. 39 (12), p. 1750-6.
Huang B, et al., Synergistic anti-tumor effects between oncolytic vaccinia virus and paclitaxel are mediated by the IFN response and HMGB1. Gene Therapy, vol. 18, p. 164-172, 2010.
Hughes et al., A rapid Orthopoxvirus purification protocol suitable for high-containment laboratories, Journal of Virological Methods, 2017, vol. 243, p. 68-73.
Hynes, et al., Analysis of a Second Bacteriophage Hyaluronidase Gene from *Streptococcus pyogenes*: Evidence for a Third Hyaluronidase Involved in Extracellular Enzymatic Activity, Infection and Immunity, 1995, vol. 63, No. 8, p. 3015-3020.
Iwasaki, et al., Enhanced CTL Responses Mediated by Plasmid DNA Immunogens Encoding Costimulatory Molecules and Cytokines. Journal of Immunology, vol. 158, p. 4591-601, 1997.
Janssens and Beyaert, Role of Toll-Like Receptors in Pathgen Recognition, Clinical Microb. Revs., vol. 16, p. 637-646, 2003.
Jhawar et al., Oncolytic Viruses—Natural Genetically Engineered Cancer Immunotherapies, Front. Oncol., vol. 7, p. 1-11, 2017.
Jiang et al., Toll-like Receptor 3-Mediated Activation of NF-kappaB and IRF3 Diverges at Toll-IL-I Receptor Domain-Containing Adapter Inducing IFN-beta. Proceedings of the National Academy of Sciences of the United States of America, vol. 101, p. 3533-8 (2004).

Jinushi, et al., MFG-ES-mediated Uptake of Apoptotic Cells by APCs Links the Pro-and-anti-inflammatory activities of GM-CSF. The Journal of Clinical Investigation, vol. 117, p. 1902-13 (2007).
Jones et al., Therapeutic Strategies for the Clinical Blockade of IL-6/gpl30 Signaling. The Journal of Clinical Investigation, vol. 121, p. 3375-83 (2011).
Kafri et al., A Packaging Cell Line for Lentivirus Vectors, J. Virol., vol. 73, No. 1, p. 576-584, 1999.
Kalinski et al., Regulation of Immune Responses by Prostaglandin E2. Journal of Immunology, vol. 188, p. 21-8 (2012).
Kalinski et al., T-cell Priming by Type-I and Type-2 Polarized Dendritic Cells: The Concept of a Third Signal. Immunol Today, vol. 20, 561-7 (1999).
Kalinski, P. & Okada, H. Polarized dendritic cells as cancer vaccines: directing effector-type T cells to tumors. Seminars in immunology 22, 173-82 (2010).
Kang et al., HMGB1 in Cancer: Good, Bad, or Both? Clin Cancer Res., 2013, vol. 19, p. 4046-4057.
Karlin et al., Applications and Statistics for Multiple High-scoring Segments in Molecular Sequences, Proc. Natl. Acad. Sci. USA, vol. 90, p. 5873-5877 (1993).
Kaufman et al., Oncolytic viruses: a new class of immunotherapy drugs, Nature Reviews, Drug Discovery, 2015, vol. 14(9), p. 642-62.
Kelly et al., Real-time Intraoperative Detection of Melanoma Lymph Node Metastases using Recombinant Vaccinia Virus GL V -1 h68 in an Immunocompetent Animal Model. International Journal of Cancer. vol. 124, p. 911-8 (2009).
Kendrew et al. (eds.), The Encyclopedia of Molecular Biology, published by Blackwell Science Ltd., 1994.
Khuri et al., A Controlled Trial of Onyx-015, an EIB Gene-deleted Adenovirus, in Combination with Chemotherapy in Patients with Recurrent Head and Neck Cancer. Nature Medicine, vol. 6, p. 879-885 (2000).
Kim et al., Antibody Association with HER-2/neu-targeted Vaccine Enhances CD8 T Cell Responses in Mice Through Fe-mediated Activation of DCs. The Journal of Clinical Investigation, vol. 118, p. 1700-11 (2008).
Kim et al., Oncolytic and Immunotherapeutic Vaccinia Induces Antibody-mediated Complement-dependent Cancer Cell Lysis in Humans. Science Translational Medicine, vol. 5, 185ra63 (2013).
Kim et al., Systemic Armed Oncolytic and Immunologic Therapy for Cancer with JX-594, a Targeted Poxvirus Expressing GM-CSF. Mol Ther, vol. 14, p. 361-70 (2006).
Kirn DH et al., Enhancing Poxvirus Oncolytic Effects through Increased Spread and Immune Evasion, Cancer Research 2008, vol. 68, No. 7, Apr. 2008.
Kirn et al., Replication-selective Virotherapy for Cancer: Biological Principles, Risk Management and Future Directions. Nat Med, vol. 7, p. 781-7 (2001).
Kirn et al., Targeted and Armed Oncolytic Poxviruses: A Novel Multi-mechanistic Therapeutic Class for Cancer. Nat Rev Cancer, vol. 9, p. 64-71 (2009).
Kirn et at., Targeting of Interferon-beta to Produce a Specific, Multi-mechanistic Oncolytic Vaccinia Virus. PLoS Med, vol. 4, e353 (2007).
Kobayashi, et al., Bacterial Pathogens Modulate an Apoptosis Differentiation Program in Human Neutrophils, Proc. Natl. Acad. Sci. USA, vol. 100, p. 10948-10953, 2003.
Kochneva et al., Engineering of double recombinant vaccinia virus with enhanced oncolytic potential for solid tumor virotherapy, Oncotarget, 2016, vol. 7, No. 45, p. 74171-74188.
Kolb-Maurer et al., Listeria Monocytogenes-Infected Human Dendritic Cells: Uptake and Host Cell Response, Infection Immunity, vol. 68, p. 3680-3688, 2000.
Kowalsky et al., Superagonist IL-15Armed Oncolytic Virus Elicits Potent Antitumor Immunity and Therapy that are Enchanced with PD-1 Blockadge, Molecular Therapy, Nature Publishing Group, 2018, vol. 26, No. 10, p. 2476-2486.
La Cava et al., The Weight of Leptin in Immunity, Nat Rev Immunol, vol. 4, p. 371-379, 2004.
Labeck, Checkpoint Inhibitors: New Insights and Current Place in Cancer Therapy, Erratum, Pharmcotherapy Publications, Inc., 2015.

(56) References Cited

OTHER PUBLICATIONS

Lalvani et al., Rapid Effector Function in CD8+ Memory T Cells, J. Exp. Med., vol. 186, p. 859-865, 1997.
Langland et al., The Role of the PKR-Inhibitory Genes, E3L and K3L, in Determining Vaccinia Virus Host Range, Virology. vol. 299(1), p. 133-41, 2002.
Lawler et al. Oncolytic Viruses in Cancer Treatment, JAMA Oncology, Jun. 1, 2017, vol. 3, No. 6, pp. 841-849.
Le et al., CDS(+) Foxp3(+) Tumor Infiltrating Lymphocytes Accumulate in the Context of an Effective Anti-tumor Response. International Journal of Cancer. Journal International du Cancer, vol. 129, p. 636-47 (2011).
Lemoine et al., Massive Expansion of Regulatory T-cells Following Interleukin 2 Treatment During a Phase 1-11 Dendritic Cell-based Immunotherapy of Metastatic Renal Cancer. International Journal of Oncology, vol. 35, No. 569-81 (2009).
Levero et al., Defective and Nondefective Adenovirus Vectors for Expressing Foreign Genes in Vitro and in Vivo, Gene, 1991, vol. 101, p. 195-202, 1991.
Li et al., CCL5-armed oncolytic virus augments CCR5-engineered NK cell infiltration and antitumor efficiency. J Immunother Cancer. 8(1):e000131, 2020, PMID: 32098828.
Li J, et al., (2011) Chemokine Expression From Oncolytic Vaccinia Virus Enhances Vaccine Therapies of Cancer. Molecular Therapy, vol. 19, No. 5, pp. 650-657, 2011.
Liu et al., The Targeted Oncolytic Poxvirus JX-594 Demonstrates Antitumoral, Antivascular, and Anti-HBV Activities in Patients with Hepatocellular Carcinoma. Mol Ther, vol. 16, p. 1637-42 (2008).
Loffreda et al., Leptin Regulates Proinflammatory Immune Responses, FASEB J, vol. 12, 57-65, 1998.
Longhi, M.P., et al., Dendritic cells require a systemic type I interferon response to mature and induce CD4+ Thl Immunity with poly IC as adjuvant. The Journal of Experimental Medicine, vol. 206, p. 1589-1602 (2009).
Lun et al., "Effects of Intravenously Administered Recombinant Vesicular Stomatitis Virus (VSV-delta-M51) on Multifocal and Invasive Gliomas", Journal of the National Cancer Institute, 2006, vol. 98, No. 21, p. 1546-1556.
Mahoney et al., Combination cancer immunotherapy and new immunomodulatory targets, Cancer Immunotherapy, Nature Reviews, Drug Discovery, vol. 14, Aug. 2015, pp. 561-584.
Mailliard et al., Alpha-type-I Polarized Dendritic Cells: A Novel Immunization Tool with Optimized CTL-inducing Activity. Cancer Res, vol. 64, p. 5934-7, (2004).
Martin-Romero et al., Human Leptin Enhances Activation and Proliferation of Human Circulating T Lymphocytes, Cell Immunol, vol. 199(1), p. 15-24, 2000.
McCart et al., Systemic cancer therapy with a tumor-selective vaccinia virus mutant lacking thymidine kinase and vaccinia growth factor genes. Cancer Res, vol. 61, p. 8751-7 (2001).
McHeyzer-Williams et al., Enumeration and Characterization of Memory Cells in the Th Compartment, Immunol. Rev., vol. 150, p. 5-21, 1996.
McIntosh et al., Vaccinia Virus Glycoprotein A34R is Required for Infectivity of Extracellular Enveloped Virus. J Virol, vol. 70:, p. 272-81, 1996.
McManus et al., Gene Silencing Using Micro-RNA Designed Hairpins, RNA, vol. 8, p. 842-850, (2002).
McMichael et al., A New Look at T Cells, J. Exp. Med., vol. 187(9), p. 1367-1371, 1998.
Meyer et al., Mapping of Deletions in the Genome of the Highly Attenuated Vaccinia Virus MVA and Their Influence on Virulence, J. of General Virology, vol. 72, p. 1031-1038, 1991.
Millipore Sigma, Benzonase endonuclease, SAFC, 2018, pp. 1-40.
Moleirinho et al., Clinical-grade Oncolytic Adenovirus Purification Using Polysorbate 20 as an Alternative for Cell Lysis, Current Gene Therapy, 2018, vol. 18, p. 366-374.
Moon EK et al., Intra-tumoral delivery of CXCL 11 via a vaccinia virus, but not by modified T cells, enhances the efficacy of adoptive T cell therapy and vaccines. Oncoimmunology, vol. 7, Issue 3, 2018.

Moss B. Poxviridae: The Viruses and Their Replication. Field's Virology (eds. D.M., K., Fields, B.N. & Howley, P.M.) Ch.84 (Lippincott-Raven, Philadelphia, 2001).
Najjar et al., Clinical Perspectives on Targeting of Myeloid Derived Suppressor Cells in the Treatment of Cancer, Frontiers in Oncology, vol. 3(49), p. 1-9, 2013.
Naldini, Nuclear Acid Delivery: Lentiviral and Retroviral Vectors, Curr. Opin. Biotechnol., vol. 9, p. 457-63, 1998.
Narang et al., Improved Phosphotriester Method for Synthesis of Gene Fragments, Meth. Enzymol., vol. 68, p. 90-99, 1979.
Needham-Vandevanter et al., Characterization of an Adduct between CC-1065 and a Defined Oligodeoxynucleotide Duplex, Nucl. Acids Res., vol. 12, p. 6159-6168, 1984.
Needleman et al., A General Method Applicable to the Search for Similarities in the Amino Acid Sequence of Two Proteins,, J. Mol. Biol., vol. 48, p. 443-453, 1970.
Nestle et al., Cancer Vaccines: The Next Generation of Tools to Monitor the Anticancer Immune Response. PLoS Med 2, e339 (2005).
Ning et al., Cancer Stem Cell Vaccination Confers Significant Antitumor Immunity. Cancer Research, vol. 72, p. 1853-64 (2012).
Nishio et al., Oncolytic Virus Expressing Rantes and IL-15 Enhances Function of CAR-Modified T Cells in Solid Tumors, Oncoimmunology, Mar. 6, 2015 (Mar. 6, 2015), vol. 4, No. 2, pp. 1-3.
O'Gorman et al., Alternate Mechanisms of Initial Pattern Recognition Drive Differential Immune Responses to Related Poxviruses. Cell Host & Microbe, vol. 8, p. 174-85 (2010).
Okada et al., Induction of CD8+ T-cell Responses Against Novel Glioma-associated Antigen Peptides and . . . Carboxymethylcellulose in Patients with Recurrent Malignant Glioma. Journal of Clinical Oncology : Official Journal of the American Society of Clinical Oncology, vol. 29, p. 330-6 (2011).
Okamura, H., et al. Cloning of a new cytokine that induces IFN-gamma production by T cells. Nature, vol. 378, p. 88-91 (1995).
O'Neill et al., Therapeutic Targeting of Toll-like Receptors for Infectious and Inflammatory Diseases and Cancer. Pharmacological Reviews, vol. 61, p. 177-97 (2009).
Orubu et al., Expression and Cellular Immunogenicity of a Transgenic Antigen Driven by Endogenous Poxviral Early Promoters at Their Authentic Loci in MVA, PLOS One 7:e40167, 2012.
Ottolino-Perry et al. Intelligent Design: Combination Therapy With Oncolytic Viruses, Molecular Therapy, Feb. 28, 2010, vol. 18, No. 2, pp. 251-263.
Parato et al., The Oncolytic Poxvirus JX-594 Selectively Replicates in and Destroys Cancer Cells Driven by Genetic Pathways Commonly Activated in Cancers, Molecular Therapy, vol. 20, No. 4, p. 749-758, 2012.
Park et al., Use of a Targeted Oncolytic Poxvirus, JX-594, in Patients with Refractory Primary or Metastatic Liver Cancer: A Phase I Trial. Lancet Oncol, vol. 9, p. 533-42 (2008).
Paul et al., Tumor Gene Therapy by MVA-Mediated Expression of T-Cell-Stimulating Antibodies, Cancer Gene Ther., vol. 9, p. 470-7, 2002.
Pearson et al., Improved Tools for Biological Sequence Comparison, Proc. Natl. Acad. Sci. USA vol. 85, p. 2444-2448, 1988.
Penna, et al., Cutting Edge: Differential Chemokine Production by Myeloid and Plasmacytoid Dendritic Cells, J. Immunol., vol. 69, p. 6673-6676, (2002).
Asagoe, et al; Down-Regulation of CXCR2 Expression on Human Polymorphonuclear Leukocytes by TN F-a1. J Immunol, 1998, vol. 160, No. 9, p. 4518-4525.
Benfield et al., Vaccinia virus protein K7 is a virulence factor that alters the acute immune response to infection; Journal of General Virology, 2013, vol. 94, p. 1647-1657.
Billottet et al., CXCR3, a double-edged sword in tumor progression and angiogenesis, Biochimica et Biophysica Acta, 2013, vol. 1836, p. 287-295.
Cronin et al., Bacterial-Mediated Knockdown of Tumor Resistance to an Oncolytic Virus Enhances Therapy, Mol Ther, 2014, vol. 22, No. 6, p. 1188-1197.

(56) References Cited

OTHER PUBLICATIONS

Dey et al., Intranasal Oncolytic Virotherapy with CXCR4-Enhanced Stem Cells Extends Survival in Mouse Model of Glioma, Stem Cell Reports, 2016, vol. 7, p. 471-482.

Di Pilato et al., NFkB activation by modified vaccinia virus as a novel strategy to enhance neutrophil migration and HIV-specific T-cell responses, PNAS, 2015, p. E1333-E1342.

Furusato et al., CXCR4 and Cancer, AM Fulton, Chemokine Receptors in Cancer, Cancer Drug Discovery and Development, 2009, p. 31-45.

Genbank Accession No. NM_00586.4 *Homo sapiens* Interleukin 2 (IL2), mRNSA, Earliest priority 1992, 4 pages.

Genbank Accession No. NM_01123041.3 Human CCR2 mRNA, Earliest priority 1988, 5 pages.

International Search Report and Written Opinion for PCT/US2022/033524, dated Nov. 23, 2022.

KaliVir Poster Presentation 894; A novel oncolytic immunotherapy, VET3-TGI, overcomes TGFB1 mediated immunosuppression, augments type-1 immune response, and displays potent therapeutic activity in multiple mouse tumor models; Published Nov. 7, 2022.

Kleinpeter et al., Vectorization in an oncolytic vaccinia virus of an antibody, a Fab and a scFv against programmed cell death-1 (PD-1) allows their intratumorial delivery and an improved tumor-growth inhibition, Oncoimmunology, 2016; vol. 5, No. 10, e1220467, p. 1-14.

Lim et al., Targeting the CCL2-CCR2 signaling axis in cancer metastasis, Oncotarget, 2016, vol. 7, No. 19, p. 28697-28710.

Malvoisin E, et al, Soluble chemokine receptor CXCR4 is present in human sera. Anal Biochem., 2011, vol. 414, No. 2, p. 202-7.

Manthey et al., "Complement component 5a (C5a)". The International Journal of Biochemistry & Cell Biology, 2009, vol. 41, No. 11, p. 2114-2117.

Muthuswamy et al., A novel oncolytic immunotherapy, VET3-TGI, overcomes TGFB1 mediated immunosuppression, augments type-1 immune response, and displays potent therapeutic activity in multiple mouse tumor models, Journal for Immuno Therapy of Cancer 2022, vol. 10, Abstract.

Ogata et al., Overexpression of PIAS3 Suppresses Cell Growth and Restores the Drug Sensitivity of Human Lung Cancer Cells in Association with PI3-K/Akt Inactivation, Neoplasia, 2006, vol. 8, No. 10, p. 817-825.

Oghumu et al., Transgenic Expression of CXCR3 on T Cells Enhances Susceptibility to Cutaneous Leishmania major Infection by Inhibiting Monocyte Maturation and Promoting Th2 Response, Infection and Immunity, 2015, vol. 83, No. 1, p. 67-76.

Pettit et al., Vaccinia Virus Transfection of Hippocampal Slice Neurons, Neuron, 1995, vol. 14, p. 685-688.

Pilna et al., Vaccinia Virus Expressing Interferon Regulatory Factor 3 Induces Higher Protective Immune Responses against Lethal Poxvirus Challenge in Atopic Organism, Viruses, 2021, vol. 13, No. 1986, p. 1-20.

Pozzobon et al., CXCR4 signaling in health and disease, Immunology Letters, 2015, vol. 177, p. 6-15.

Raemdonck et al., CXCR3 ligands in disease and therapy, Cytokine & Growth Factor Reviews, 2015, vol. 26, p. 311-327.

Rein, D.T., et al., Evaluation of tissue-specific promoters in carcinomas of the cervix uteri. J. Gene Med., 2004, vol. 6, p. 1281-1289.

Schonbeck U, "The CD40/CD154 receptor/ligand dyad". Cellular and Molecular Life Sciences. 2001, vol. 58, No. 1, p. 4-43.

Wu et al., Altered CXCR3 isoform expression regulates prostate cancer cell migration and invasion, Molecular Cancer, 2012, vol. 11, No. 3, p. 1-16.

Wu et al., Structures of the CXCR4 Chemokine GPCR with Small-Molecule and Cyclic Peptide Antagonists, Science, 2010, vol. 330, p. 1066-1071.

Yoshie, Chemokine receptors as therapeutic targets, Japanese Journal of Clinical Immunology, 2013, vol. 36, No. 4, pp. 189-196.

Zhang JM, An J. Cytokines, inflammation, and pain. Int Anesthesiol Clin., 2007, vol. 45, No. 2, p. 27-37.

Zhou et al., Tumor-targeting bacteria engineered to fight cancer, Nat Rev Cancer, 2018, vol. 18, p. 727-743.

\* cited by examiner

ONCOLYTIC VIRUSES FOR MODIFIED MHC EXPRESSION

CROSS-REFERENCE

This application claims the benefit of PCT/US2022/026703 filed Apr. 28, 2022, which claims the benefit of U.S. Provisional Application No. 63/182,243 filed Apr. 30, 2021, each of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Apr. 24, 2023, is named 199249_716301_SL.XML and is 69,632 bytes in size.

BACKGROUND

Cancer is the second leading cause of death in the United States. Challenges for commercially available therapies exists around selective targeting of cancer cells, localized gene expression, and reaching and modifying the tumor microenvironment (TME). Thus, there remains a need for improved compositions and methods of use to address these challenges.

BRIEF SUMMARY

Provided herein are compositions, wherein the composition comprises: an oncolytic virus, wherein the oncolytic virus comprises a genome modification, wherein the genome modification comprises an exogenous nucleic acid encoding for an MHC I inhibitor. Further provided herein are compositions, wherein the genome modification further comprises: a deletion or functional deletion of an endogenous nucleic acid encoding an MHC II inhibitor; or an exogenous nucleic acid that results in activation or enhanced activation of MHC II presentation. Further provided herein are compositions, wherein the genome modification further comprises: a deletion or functional deletion of an endogenous nucleic acid encoding an MHC II inhibitor; and an exogenous nucleic acid that results in activation or enhanced activation of MHC II presentation. Further provided herein are compositions, wherein the deletion or functional deletion of the endogenous nucleic acid encoding the MHC II inhibitor comprises a deletion or functional deletion of a vaccinia virus gene encoding protein A35. Further provided herein are compositions, wherein the deletion or functional deletion of the vaccinia virus gene encoding protein A35 is a deletion or functional deletion of gene WR158. Further provided herein are compositions, wherein the exogenous nucleic acid that results in activation or enhanced activation of the MHC II presentation encodes for a protein selected from: an apoptosis inhibitor protein; a necrotic cell death activator protein; an autophagy enhancer protein; an asparaginyl endopeptidase; a class II transactivator; an interferon-gamma; a Toll-like receptor activator; or a dendritic cell maturation activator. Further provided herein are compositions, wherein the exogenous nucleic acid encodes for the autophagy enhancer protein, and wherein the autophagy enhancer protein is HMGB1 or a functional domain or a variant thereof. Further provided herein are compositions, wherein the exogenous nucleic acid encodes for the dendritic cell maturation activator, wherein the dendritic cell maturation activator comprises osteopontin, TNF-alpha, or a functional fragment or variant thereof. Further provided herein are compositions, wherein the protein encoded by the exogenous nucleic acid is fused to a secretion sequence, a cell permeabilizing domain, or a combination thereof. Further provided herein are compositions, wherein the oncolytic virus is a poxvirus, an adeno associated virus, an adenovirus, Newcastle disease virus (NDV), Reovirus (RV), mengovirus, Myxoma virus (MYXV), Measles virus (MV), Herpes Simplex virus (HSV), Vaccinia virus (VV), Vesicular Stomatitis virus (VSV), and Polio virus (PV). Further provided herein are compositions, wherein the poxvirus comprises a betaentomopoxvirus, a yatapoxvirus, a cervidpoxvirus, a gammaentomopoxvirus, a leporipoxvirus, a suipoxvirus, a molluscipoxvirus, a crocodylidpoxvirus, an alphaentomopoxvirus, a capripoxvirus, an avipoxvirus, or a parapoxvirus. Further provided herein are compositions, wherein the poxvirus is a vaccinia virus. Further provided herein are compositions, wherein the MHC I inhibitor causes an inhibition or partial inhibition of MHC I presentation. Further provided herein are compositions, wherein the exogenous nucleic acid encoding the MHC I inhibitor comprises a gene encoding one or more cowpox virus proteins. Further provided herein are compositions, wherein the exogenous nucleic acid encoding the MHC I inhibitor comprises a gene encoding cowpox protein CPXV012 or a functional fragment or a variant thereof. Further provided herein are compositions, wherein the exogenous nucleic acid encoding the MHC I inhibitor comprises a gene encoding cowpox protein CPXV203 or a functional fragment or a variant thereof. Further provided herein are compositions, wherein the exogenous nucleic acid encoding the MHC I inhibitor comprises a gene encoding at least one of: Epstein-Barr virus encoded nuclear antigen 1 protein; Herpes simplex virus encoded ICP47 protein; Herpes simplex virus encoded UL49.5 protein; Cytomegalovirus encoded US6, US2, US3, US11, or gp48 protein; Epstein-Barr Virus encoded BNLF2a protein; Adenovirus encoded E3-19K protein; Human Immunodeficiency Virus or Simian Immunodeficiency Virus encoded Nef protein; Kaposi's sarcoma-associated herpesvirus encoded kK3, vIRF3 or kK5 protein; or a dominant negative form of IRF7 or IRF3. Further provided herein are compositions, wherein the MHC I inhibitor comprises a TAP inhibitor. Further provided herein are compositions, wherein the TAP inhibitor acts wholly or primarily within infected cells. Further provided herein are compositions, wherein the genome modification reduces an immune response targeting a virus-infected tumor cell and increases an immune response targeting cells surrounding the virus-infected tumor cell. Further provided herein are compositions, further comprising a deletion of a thymidine kinase gene. Further provided herein are compositions, further comprising an exogenous nucleic acid encoding a hyaluronidase. Further provided herein are compositions, wherein the hyaluronidase is PH-20 or HysA. Further provided herein are compositions, wherein the oncolytic virus is a vaccinia virus, and the vaccinia virus is a Western Reserve strain Vaccinia virus (ATCC VR-1354), a Copenhagen strain, an IHD strain, a Wyeth strain (ATCC VR-325), a NYCBOH strain, a Tian Tan strain, a Lister strain, an Ankara strain (ATCC VR-1508 or ATTC VR1566), a USSR strain, or an ACAM2000 strain.

Provided herein are compositions, wherein the composition comprises an oncolytic virus, wherein the oncolytic virus comprises a genome modification; wherein the genome modification comprises a deletion or functional deletion of a vaccinia virus gene encoding A35 protein and insertion of an exogenous gene encoding a cowpox protein CPXV012 or a cowpox protein CPXV203. Further provided herein are compositions, wherein the oncolytic virus is a poxvirus, an adeno associated virus, an adenovirus, Newcastle disease virus (NDV), Reovirus (RV), mengovirus, Myxoma virus (MYXV), Measles virus (MV), Herpes Simplex virus (HSV), Vaccinia virus (VV), Vesicular Stomatitis virus (VSV), and Polio virus (PV). Further provided herein are compositions, wherein the poxvirus comprises a betaentomopoxvirus, a yatapoxvirus, a cervidpoxvirus, a gammaentomopoxvirus, a leporipoxvirus, a suipoxvirus, a molluscipoxvirus, a crocodylidpoxvirus, an alphaentomopoxvirus, a capripoxvirus, an avipoxvirus, or a parapoxvirus. Further provided herein are compositions, wherein the oncolytic virus is a vaccinia virus. Further provided herein are compositions, wherein the exogenous gene encoding cowpox protein CPXV012 is at a locus of the gene encoding A35 protein of a vaccinia virus. Further provided herein are compositions, wherein the exogenous gene encoding cowpox protein CPXV203 is at a locus of the gene encoding A35 protein of a vaccinia virus. Further provided herein are compositions, wherein the genome modification further comprises at least one of: an exogenous nucleic acid that codes for a chemokine receptor or a functional domain or a variant thereof; or an exogenous nucleic acid that codes for a cytokine or a functional domain or a variant thereof. Further provided herein are compositions, comprising the exogenous nucleic acid that codes for a cytokine or a functional domain or a variant thereof, wherein the cytokine comprises at least one of: interleukin-2 (IL-2), interleukin-15/interleukin-15Ra (IL15/IL15Ra), interleukin-7 (IL-7), or a functional domain or a variant thereof. Further provided herein are compositions, wherein the genome modification comprises an insertion of an exogenous nucleic acid that codes for a fusion protein comprising a cytokine and a metabolic modulator protein. Further provided herein are compositions, comprising the exogenous nucleic acid that codes for the chemokine receptor or a functional domain or a variant thereof, wherein the chemokine receptor comprises at least one of: CXCR4, CCR2, or functional domains or variants thereof. Further provided herein are compositions, wherein the chemokine receptor comprises the CXCR4 or a functional domain or a variant thereof. Further provided herein are compositions, wherein the chemokine receptor comprises the CCR2 or a functional domain or a variant thereof, wherein the CCR2 comprises a wild-type CCR2 or a mutated CCR2. Further provided herein are compositions, wherein the exogenous nucleic acid that codes for the chemokine receptor or a functional domain or a variant thereof comprises a codon optimized sequence. Further provided herein are compositions, wherein the exogenous nucleic acid that codes for the chemokine receptor or a functional domain or a variant thereof comprises a non-codon optimized sequence. Further provided herein are compositions, wherein the genome modification comprises mutation or a complete or a partial deletion of a viral gene comprising at least one of: A52R, B15R, K7R, A46R, N1L, E3L, K1L, M2L, C16, N2R, B8R, B18R, or VH1 of a vaccinia virus or a functional domain or fragment or variant thereof, or any combinations thereof. Further provided herein are compositions, further comprising a deletion of a thymidine kinase gene. Further provided herein are compositions, further comprising an exogenous nucleic acid encoding a hyaluronidase. Further provided herein are compositions, wherein the hyaluronidase is PH-20 or HysA. Further provided herein are compositions, wherein the oncolytic virus is a vaccinia virus, and the vaccinia virus is a Western Reserve strain Vaccinia virus (ATCC VR-1354), a Copenhagen strain, an IHD strain, a Wyeth strain (ATCC VR-325), a NYCBOH strain, a Tian Tan strain, a Lister strain, an Ankara strain (ATCC VR-1508 or ATTC VR1566), a USSR strain, or an ACAM2000 strain.

Provided herein are pharmaceutical compositions comprising the composition according as described herein and a pharmaceutically acceptable excipient. Further provided herein are pharmaceutical compositions, wherein the excipient comprises one or more of a buffering agent, a stabilizer, an antioxidant, a binder, a diluent, a dispersing agent, a rate controlling agent, a lubricant, a glidant, a disintegrant, a plasticizer, a preservative, or any combinations thereof. Further provided herein are pharmaceutical compositions, wherein the excipient comprises di-sodium hydrogen phosphate dihydrate, sodium dihydrogen phosphate dihydrate, sodium chloride, myo-inositol, sorbitol, or any combinations thereof. Further provided herein are pharmaceutical compositions, wherein the pharmaceutical composition does not comprise a preservative. Further provided herein are pharmaceutical compositions, further comprising one or more of a preservative, a diluent, and a carrier. Further provided herein are pharmaceutical compositions, further comprising an additional active ingredient or a salt thereof. Further provided herein are pharmaceutical compositions, wherein the excipient is sterile water. Further provided herein are pharmaceutical compositions, further comprising an additional active ingredient, wherein the additional active ingredient is an anti-cancer agent or a further oncolytic virus.

Provided herein are methods of reducing growth of a cancer cell, the methods comprising administering to a cancer cell: the composition or the pharmaceutical composition as described herein.

Provided herein are methods for treating cancer, the method comprising: administering to a subject having a cancer, the composition or the pharmaceutical composition as described herein. Further provided herein are methods, wherein the administering comprises an intratumoral administration, an intraperitoneal administration, an oral administration, an intravenous administration, an intranasal administration, a sublingual administration, a rectal administration, a transdermal administration, or any combination thereof. Further provided herein are methods, comprising administering a further therapy, wherein the further therapy comprises chemotherapy, radiation, oncolytic viral therapy with an additional virus, treatment with immunomodulatory proteins, a CAR T cellular therapy, an anti-cancer agent, or any combinations thereof. Further provided herein are methods, wherein the further therapy comprises administering an immunomodulatory agent comprising anti-CD33 antibody and variable region thereof, an anti-CD11b antibody and variable region thereof, a COX2 inhibitor, a cytokine, a chemokine, an anti-CTLA4 antibody or an antigen binding fragment thereof, an anti-PD-1 antibody or an antigen binding fragment thereof, an anti-PD-L1 antibody or an antigen binding fragment thereof, or a TLR agonist.

Provided herein are methods of treatment comprising administering to a subject in need thereof the composition or the pharmaceutical composition as described herein. Further provided herein are methods, wherein the administering comprises an intratumoral administration. Further provided herein are methods, wherein the administering comprises a systemic administration. Further provided herein are methods, wherein the systemic administration comprises at least one of: an intraperitoneal administration, an oral administration, an intravenous administration, an intranasal administration, a sublingual administration, a rectal administration, a transdermal administration, or any combination thereof. Further provided herein are methods, wherein the subject has a cancer, and wherein the cancer is at least one of: a melanoma, a hepatocellular carcinoma, a breast cancer, a lung cancer, a non-small lung cancer, a peritoneal cancer, a prostate cancer, a bladder cancer, an ovarian cancer, a leukemia, a lymphoma, a renal cell carcinoma, a pancreatic cancer, an epithelial carcinoma, a gastric/GE junction adenocarcinoma, a cervical cancer, a colon carcinoma, a colorectal cancer, a duodenal cancer, a pancreatic adenocarcinoma, an adenoid cystic, a sarcoma, a mesothelioma, a glioblastoma multiforme, a astrocytoma, a multiple myeloma, a prostate carcinoma, a hepatocellular carcinoma, a cholangiocarcinoma, a pancreatic adenocarcinoma, a head and neck squamous cell carcinoma, a cervical squamous-cell carcinoma, an osteosarcoma, an epithelial ovarian carcinoma, an acute lymphoblastic lymphoma, a myeloproliferative neoplasm, or any combination thereof. Further provided herein are methods, wherein the composition or the pharmaceutical composition is administered at a dosage from about $10^6$ PFU/mL to about $10^{10}$ PFU/mL of the oncolytic virus. Further provided herein are methods, wherein the composition or the pharmaceutical composition is administered at a dosage of about $3\times10^9$ PFU/mL of the oncolytic virus. Further provided herein are methods, wherein the composition or the pharmaceutical composition is administered in three doses, and wherein each of the three doses is administered in an amount and period of administration independent of any other dose. Further provided herein are methods, wherein the three doses are administered at a first dose, a second dose, and a third dose, and, wherein the first dose is lower than the second dose, and the second dose is lower than the third dose. Further provided herein are methods, wherein the three doses are administered at a first dose, a second dose, and a third dose, and wherein the first dose is higher than the second dose, and the second dose is higher than the third dose. Further provided herein are methods, wherein the period of administration for the three doses is each, independently, about 1 day, about 2 days, about 3 days, about 4 days, about 5 days, about 6 days, about 1 week, about 2 week, about 3 weeks, about 4 weeks, about 6 weeks, about 7 weeks, about 8 weeks, about 9 weeks, about 10, weeks, about 12 weeks, about 4 months, about 5 months, about 6 months, about 7 months, about 8 months, about 9 months, about 10 months, about 11 months or about 1 year. Further provided herein are methods, wherein the composition or the pharmaceutical composition independently comprises a liquid dosage form that is administered at a volume from about 1 mL to about 5 mL, about 5 mL to 10 mL, about 15 mL to about 20 mL, about 25 mL to about 30 mL, about 30 mL to about 50 mL, about 50 mL to about 100 mL, about 100 mL to 150 mL, about 150 mL to about 200 mL, about 200 mL to about 250 mL, about 250 mL to about 300 mL, about 300 mL to about 350 mL, about 350 mL to about 400 mL, about 400 mL to about 450 mL, about 450 mL to 500 mL, about 500 mL to 750 mL, or about 750 mL to 1000 mL. Further provided herein are methods, wherein the composition or the pharmaceutical composition is administered in a liquid dosage form, a solid dosage form, an inhalable dosage form, an intranasal dosage form, a liposomal formulation, a dosage form comprising nanoparticles, a dosage form comprising microparticles, a polymeric dosage form, or any combination thereof. Further provided herein are methods, wherein the composition or the pharmaceutical composition is administered for a duration of about 1 day, about 2 days, about 3 days, about 4 days, about 5 days, about 6 days, about 1 week, about 2 week, about 3 weeks, about 4 weeks, about 6 weeks, about 7 weeks, about 8 weeks, about 9 weeks, about 10, weeks, about 12 weeks, about 4 months, about 5 months, about 6 months, about 7 months, about 8 months, about 9 months, about 10 months, about 11 months, or about 1 year. Further provided herein are methods, wherein the composition or the pharmaceutical composition is administered once daily, twice daily, once every week, once every two weeks, or once every three weeks. Further provided herein are methods, wherein the composition or the pharmaceutical composition is administered as a bolus injection or a slow infusion. Further provided herein are methods, wherein the administration of the composition or the pharmaceutical composition results in a first peak viral load after about 1 hour to about 3 days and a second peak viral load after about 3 days to about 10 days from administration of a first dose. Further provided herein are methods, comprising administration of a further therapy, wherein the further therapy is administered for a duration of about 1 day, about 2 days, about 3 days, about 4 days, about 5 days, about 6 days, about 1 week, about 2 week, about 3 weeks, about 4 weeks, about 6 weeks, about 7 weeks, about 8 weeks, about 9 weeks, about 10, weeks, or about 12 weeks. Further provided herein are methods, wherein the further therapy is administered once daily, twice daily, once every 1 day, once every 2 days, once every 3 days, once every 4 days, once every 5 days, once every 6 days, once every 1 week, once every 2 week, once every 3 weeks, once every 4 weeks, once every 6 weeks, once every 7 weeks, once every 8 weeks, once every 9 weeks, once every 10, weeks, once every 12 weeks, once every 4 months, once every 5 months, once every 6 months, once every 7 months, once every 8 months, once every 9 months, once every 10 months, once every 11 months, or once every 1 year. Further provided herein are methods, wherein the further therapy is administered in a liquid dosage form, a solid dosage form, an inhalable dosage form, an intranasal dosage form, a liposomal formulation, a dosage form comprising nanoparticles, a dosage form comprising microparticles, a polymeric dosage form, or any combination thereof. Further provided herein are methods, wherein the further therapy is administered orally, intravenously, by an intratumoral injection, by intraperitoneal injection, or by radiation. Further provided herein are methods, wherein the further therapy comprises chemotherapy, radiation, oncolytic viral therapy with an additional virus, treatment with immunomodulatory proteins, a CAR T cellular therapy, an anti-cancer agent, or any combinations thereof. Further provided herein are methods, wherein the further therapy comprises administration of an immunomodulatory agent comprising anti-CD33 antibody and variable region thereof, an anti-CD11b antibody and variable region thereof, a COX2 inhibitor, a cytokine, a chemokine, an anti-CTLA4 antibody or an antigen binding fragment thereof, an anti-PD-1 antibody or an antigen binding fragment thereof, an anti-PD-L1 antibody or an antigen binding fragment thereof, or a TLR agonist. Further provided herein are methods, wherein the further therapy comprises administration of the anti-cancer agent, wherein the anti-cancer agent is a chemotherapeutic agent. Further provided herein are methods, wherein the subject is human.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The novel features of the disclosure are set forth with particularity in the appended claims. A better understanding of the features and advantages of this disclosure will be obtained by reference to the following detailed description that sets forth illustrative embodiments, in which the principles of this disclosure are utilized.

DETAILED DESCRIPTION OF THE DISCLOSURE

Figure 1:
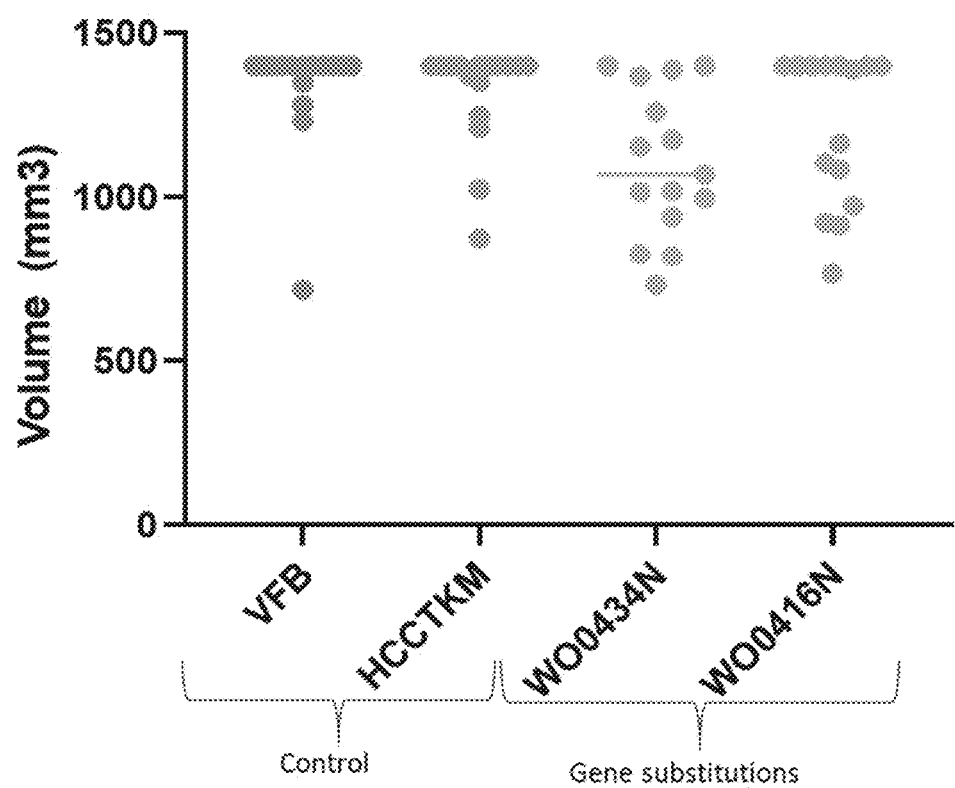
FIG. 1 depicts the change in B16 tumor volume, shown in cubic millimeters on the y-axis, following treatment with vehicle formulated buffer (VFB), or recombinant vaccinia virus comprising: a TK deletion (HCCTKM); TK and A52R deletions and substitution of the gene encoding the A35 protein with a cowpox CPXV012 gene (WO0434N); or TK and A52R deletions without insertion of the exogenous nucleic acid (WO416N).

While preferred embodiments of this disclosure have been shown and described herein, it will be obvious to those skilled in the art that such embodiments are provided by way of example only. Numerous variations, changes, and substitutions will now occur to those skilled in the art without departing from this disclosure. It should be understood that various alternatives to the embodiments of this disclosure described herein may be employed in practicing the disclosure.

This disclosure provides, in some embodiments, recombinant oncolytic viruses and methods of using said oncolytic viruses for the treatment of cancer. In some embodiments, the oncolytic viruses of this disclosure comprise modification in the viral genome encoding exogenous nucleic acids to enhance the oncolytic immunotherapy by remodeling the tumor microenvironment and with enhanced systemic delivery. The present disclosure further relates to the composition of matter comprising such oncolytic viruses and the method of use and kits for cancer treatments.

Certain Definitions

As used herein, the singular forms "a", "an" and "the," may refer to both the singular as well as plural, unless the context clearly indicates otherwise. As used herein, the term "comprises" can mean "includes." Thus, "comprising one or more modifications in the viral genome" may mean "including at least one of the modifications in the viral" without excluding other elements. In case of conflict, the present specification, including explanations of terms, will control. In addition, the materials, methods, and examples are illustrative only and not intended to be limiting. The term "about" or "approximately" can mean within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value, such as ±10% of the value modified by the term "about".

The term "recombinant oncolytic virus" as defined herein include an oncolytic virus strain engineered to delete or functionally delete one or more endogenous nucleic acid sequences and/or insert or partially insert one or more exogenous nucleic acid sequences. The term also includes the substitution of the one or more endogenous nucleic acid sequences in a viral genome with the one or more exogeneous nucleic acid at the same or different loci.

The term "effective amount" as used herein, can refer to an amount of an agent (such as a recombinant oncolytic virus disclosed herein, as well as other anti-cancer agents) that is sufficient to effect beneficial or desired results. An effective amount (also referred to as a therapeutically effective amount) may vary depending upon one or more of: the subject and disease condition being treated, the weight and age of the subject, the severity of the disease condition, the manner of administration and the like, which can readily be determined by one of ordinary skill in the art. The beneficial therapeutic effects can include, but are not limited to, enablement of diagnostic determinations; amelioration of a disease, symptom, disorder, or pathological condition; reducing or preventing the onset of a disease, symptom, disorder or condition; and generally counteracting a disease, symptom, disorder or pathological condition.

Overview

Provided herein are compositions and methods relating to inhibiting major histocompatibility complex (MHC) Class I presentation within virally infected cells as a means to (i) reduce the immune response targeting the virus and virus infected cells while increasing the immune response targeting the surrounding tumor. Further provided herein are compositions and methods for recombinant oncolytic viruses engineered to activate major histocompatibility complex (MHC) Class II presentation throughout the tumor microenvironment, while also helping to overcome immune resistance to immune oncology therapies (e.g., immune check point inhibitor therapies) mediated by tumor-mediated downregulation of MHC II presentation.

In some embodiments, the recombinant oncolytic virus is a vaccinia virus, wherein the vaccinia virus can be modified such that the virus (i) is deleted for vaccinia's natural MHC II inhibitor; and (ii) has been engineered to express an MHC I inhibitor from cowpox virus. It is shown herein, in some aspects, that substitution of vaccinia virus gene WR158 encoding protein A35 (NCBI Accession No. YP_233040) with a DNA sequence encoding viral promoter P7.5 (SEQ ID NO: 1) driving expression of cowpox protein CPXV012 (NCBI accession No. NP_619801) (SEQ ID NO: 2) or with a DNA sequence encoding cowpox protein CPXV203 can result in a greater therapeutic activity than the same virus without this substitution.

In some embodiments, the MHC I inhibitor can be selected from one or more of TAP inhibitors, such as UL49.5; ICP47; US6, BNLF2a.

In some embodiments, better activation of MHC II presentation can be achieved by other methods including or excluding the deletion of vaccinia's natural MHC II inhibitor. These other methods include but are not limited to modification in the recombinant vaccinia virus such that the viral genome is modified by insertion of the gene encoding at least one of an apoptosis inhibitor protein or a necrotic cell death activator protein; an autophagy enhancer protein (e.g., HMGB1); an asparaginyl endopeptidase; a class II transactivator (CIITA); an interferon-gamma; a Toll-like receptors (TLR) activator; a dendritic cell (DC) maturation activator (e.g., osteopontin or TNF-alpha) or Fas ligand.

In some embodiments, the inhibition of major histocompatibility complex (MHC) Class I presentation can be achieved by other methods including or excluding the insertion of a gene from cowpox virus expressing an MHC I inhibitor. These other methods include but are not limited to insertion of an exogenous gene in the viral genome from one or more of a MHC I inhibitor derived from a herpesvirus such as Epstein-Barr virus encoded nuclear antigen 1 (EBNA1) or BNLF2a proteins, Herpes simplex virus encoded ICP47 or UL49.5 proteins, Herpes simplex virus encoded protein, Human cytomegalovirus (HCMV) encoded US6, US2, US3 US11 or gp48 proteins, Epstein-Barr Virus encoded BNLF2a protein, Kaposi's sarcoma-associated herpesvirus (KSHV) encoded kK3, vIRF3 or kK5 protein, or dominant negative form of IRF7.

Other viral proteins that down regulate MHC I include for example Adenovirus encoded E3-19K protein, Human Immunodeficiency Virus 1 encoded Nef protein, Human Immunodeficiency Virus 2 encoded Nef protein, and Simian Immunodeficiency Virus 1 encoded Nef protein.

Oncolytic Viruses

Provided herein are compositions comprising an oncolytic virus which is modified. Modifications include the addition of an exogenous nucleic acid described herein. Further modifications include the addition of a genomic modification as described herein. Exemplary oncolytic viruses for inclusion in composition described herein include, without limitation, a poxvirus, an adeno associated virus, an adenovirus, Newcastle disease virus (NDV), Reovirus (RV), mengovirus, Myxoma virus (MYXV), Measles virus (MV), Herpes Simplex virus (HSV), Vaccinia virus (VV), Vesicular Stomatitis virus (VSV), and Polio virus (PV). These oncolytic viruses have a proclivity to specifically target cancer cells, and upon virus replication cause significant cell death and tumor regression. In some embodiments, oncolytic viruses as described herein, kill cancer or tumor cells through mechanisms such as the direct lysis of said cells, by stimulating immune response towards said cells, apoptosis, expression of toxic proteins, autophagy and shut-down of protein synthesis, induction of anti-tumoral immunity, or any combinations thereof. In some embodiments, the poxvirus comprises a betaentomopoxvirus, a yatapoxvirus, a cervidpoxvirus, a gammaentomopoxvirus, a leporipoxvirus, a suipoxvirus, a molluscipoxvirus, a crocodylidpoxvirus, an alphaentomopoxvirus, a capripoxvirus, an avipoxvirus, or a parapoxvirus. In some embodiments, the pox virus comprises a vaccinia virus. In some embodiments, the pox virus is a vaccinia virus.

Based on these approaches, there is also provided compositions and methods for tumor therapy such that immune response targeting infected cells in the tumor is reduced and instead uninfected tumor cells are better targeted (e.g., this approach can reduce anti-viral immunity in favor of anti-tumor immune response).

Provided herein are recombinant viruses incorporating genome modification, including insertions, mutations or deletions, as well as insertion of exogenous genes described herein. In some embodiments, such modifications are generated by spontaneous recombination with a transfer vector. For example, the vector, which can be a circular plasmid or linear DNA fragment, can comprise a desired DNA sequence to be added to the viral genome followed by a gene encoding a floxxed fluorescent reporter protein under a strong viral promoter. Such components can be flanked by 200 to 1000 bases in length of DNA sequence homologous to viral genomic DNA immediately preceding, and immediately following the desired integration site, which direct site-specific integration of the vector payload plus reporter. Purified vector DNA is transfected into a virus-susceptible adherent cell line, for example: 143B seeded at approximately one million cells in a single well of a 6-well cell culture plate. Transfected cells are then infected with a virus into which the vector DNA is intended to integrate. Recombination between the vector and viral genome occurs spontaneously during viral replication. One to three days post-infection, recombinant virus (alongside parental virus) is harvested from the transfected cells by removing medium and lysing the cell monolayer. Recombinant virus is purified from parental virus by plaque selection. Multi-well plates (e.g., 96-well, treated for adherent cell culture) are seeded with between $1.2 \times 10^4$-$3.0 \times 10^4$ cells per well on the day of plaque selection. Lysate comprising a mixture of recombinant and parental virus is sonicated, then diluted in cell culture medium and distributed between wells in the top row of a seeded 96-well plate. Medium from the infected row is mixed and transferred into the next adjacent row of cells in the plate. The process of serial dilution is performed for all rows in the selection plate. Infected plates are stored in a cell culture incubator for two to three days to allow plaques to develop. Plaques formed by recombinant virus are fluorescent due to reporter gene expression and are identified using a fluorescence microscope. Recombinant plaques are picked manually using a single-channel micropipette—typically 0.5 to 3.0 microliters of material are picked from each plaque. Preferred plaques are round, uniform in reporter intensity, and alone within their well. Picked plaques are frozen, thawed, then diluted and used to infect additional 96-well selection plates. A pure population (wholly GFP-positive) of recombinant plaques is achieved after several rounds of selection. The reporter gene is then deleted from the viral genome by transfecting cells with a vector that encodes cre recombinase under a viral promoter. Transfected cells are infected with reporter-positive virus, allowing expressed cre to remove the floxxed reporter. Reporter-free virus is purified by plaque selection in the same manner as previous described, targeting GFP-lacking plaques that are alone in their wells.

Recombinant Vaccinia Viruses

In some embodiments, the oncolytic virus is a vaccinia virus. As used interchangeably herein, the term "recombinant vaccinia virus" or a "recombinant vaccinia virus," can relate to a vaccinia virus that has been modified. Example modifications include, without limitation, introducing viral backbone mutations, to express genes/peptides of a vaccinia virus, or deleting genes, where the modification facilitates among other things, an increased immune response. In some embodiments, introducing a viral backbone mutation comprises a complete deletion or a partial deletion of one or more virulence genes, or substitutions with one or more viral virulence genes (non-limiting examples include genes that are known to inhibit cytokines involved in the Th1 immune response, or in innate immune signaling, or inhibitors of other components of the immune response, or with vaccinia virulence genes exchanged with more or less potent genes of equivalent function from other poxviruses).

Modifications in the genome of the virus can be at one or more locations within the genome. In some embodiments, modifications in the genome of the virus are located contiguously in the genome. In some embodiments, modifications in the genome of the virus are distributed throughout the genome.

Exemplary vaccinia viruses include, without limitation, the following strains for modification by inclusion of a fusion construct described herein: Western Reserve Vaccinia virus (ATCC VR-1354), Vaccinia virus Ankara (ATCC VR-1508), Vaccinia virus Ankara (ATCC VR-1566), Vaccinia virus strain Wyeth (ATCC VR-1536), or Vaccinia virus Wyeth (ATCC VR-325). Furthermore, in some embodiments the recombinant vaccinia viruses are modified versions of a wild type or attenuated vaccinia virus strain. Nonlimiting examples of vaccinia virus strains include Western Reserve strain of vaccinia virus, Copenhagen strain, Wyeth (NYCBOH) strain, Tian Tan strain, Lister, USSR, Ankara, NYVAC strain, and recombinant vaccinia virus Ankara (MVA). Additional exemplary strains for inclusion in compositions described herein are, without limitation, Western Reserve strain Vaccinia virus, a Copenhagen strain, an IHD strain, a Wyeth strain, a NYCBOH strain, a Tian Tan strain, a Lister strain, an Ankara strain, a USSR strain, or an ACAM2000 strain. The base vaccinia virus strain modified as set forth herein may itself comprise one or more mutation relative to its parent strain, for example, but not limited to, one or more of the following: deletion in TK (also referred to herein as "TK-"); deletion in A52 (also referred to herein as "A52-"). An exemplary vaccinia virus is Western Reserve vaccinia viruses. Any known vaccinia virus, or modifications thereof that correspond to those provided herein or known to those of skill in the art are also covered in the scope of this application.

Modification that Inhibits MHC I Presentation

Presentation of peptides on Major Histocompatibility Complex I, or MHC I, is a pathway in which peptides are presented on cells to alert the immune system to virally infected cells. For example, an infected cell may present a viral peptide on MHC I, thereby alerting cytotoxic T lymphocytes to destroy these cells. Upon infection of a host with a recombinant oncolytic virus, presentation of peptides on MHC I can be inhibited.

Provided herein, in some embodiments of this disclosure, are modifications of the recombinant oncolytic virus that provide inhibition or partial inhibition of MHC I presentation. The modification can comprise an insertion or partial insertion of an exogenous MHC I inhibitor. The insertion of the MHC I inhibitor can be provided by an exogenous nucleic acid that encodes said MHC I inhibitor. The exogenous nucleic acid encoding said MHC I inhibitor can be inserted into a nucleic acid sequence of an oncolytic viral genome such as the cowpox virus. In certain instances, the MHC I inhibitor is inserted into a non-coding region. In other instances, the inhibitor is inserted into a nucleic acid sequence encoding a viral protein of the oncolytic virus. In certain instances, the MHC I inhibitor is inserted into a region of the oncolytic viral genome that allows the virus to replicate in tumor cells. In certain instances, concerning the cowpox virus, the MHC I inhibitor can be inserted into at least 1, at least 2, at least 3, at least 4, at least 5, at least 6, at least 7, at least 8, at least 9, or at least 10 genes. The gene encoding the cowpox virus protein can be CPXV012, CPXV203, or any combination thereof. In some embodiments, the cowpox virus protein, including any combinations of substitution, insertion, and deletion, can result in a sequence with less than 100%, 99%, 98%, 97%, 96%, 95%, 94%, 93%, 92%, 91%, 90% or less sequence homology to the wild-type sequence of the viral gene or a viral protein coded by the gene. MHC I presentation can been decreased by at least 1%, at least 2%, at least 5%, at least 10%, at least 15%, at least 20%, at least 25%, at least 30%, at least 35%, at least 40%, at least 45%, at least 50%, at least 55%, at least 65%, at least 70%, at least 75%, at least 80%, at least 85%, at least 95%, or at least 100%.

The exogenous nucleic acid, in some embodiments, can encode at least one TAP inhibitor. The exogenous nucleic acid, in some embodiments, can encode at least one gene selected from the group consisting of: Epstein-Barr virus encoded nuclear antigen 1 (EBNA1) protein, Herpes simplex virus encoded ICP47 protein, Herpes simplex virus encoded UL49.5 protein, Human cytomegalovirus (HCMV) encoded US6, US2, US3 or US11 protein, Epstein-Barr Virus encoded BNLF2a protein, Adenovirus encoded E3-19K protein, Cytomegalovirus encoded gp48 protein, Human Immunodeficiency Virus encoded Nef protein, Kaposi's sarcoma-associated herpesvirus (KSHV) encoded kK3, vIRF3 or kK5 protein or a dominant negative form of IRF7.

Modification that Activates MHC Class II Presentation

Provided herein, in some embodiments of this disclosure, are modifications of the recombinant oncolytic virus resulting in activation of MHC II presentation, wherein the modification can comprise at least one of: i) a deletion or partial deletion of one or more MHC II inhibitors (e.g., natural MHC II inhibitors); ii) insertion of an apoptosis inhibitor proteins or necrotic cell death activator proteins; or any combination thereof. The modification can be a deletion of an oncolytic virus gene. The modification can be a deletion (a complete or a partial deletion) of A35 encoding gene. The modification of the deletion of the A35 encoding can be a deletion or functional deletion of viral gene WR158. In some embodiments, the MHC II inhibitor, including any combinations of substitution, insertion, and deletion, can result in a sequence with less than 100%, 99%, 98%, 97%, 96%, 95%, 94%, 93%, 92%, 91%, 90% or less sequence homology to the wild-type sequence of the viral gene or a viral protein coded by the gene, that is the natural MHC II inhibitor of the virus. MHC II presentation can be activated or enhanced by at least 1%, at least 2%, at least 5%, at least 10%, at least 15%, at least 20%, at least 25%, at least 30%, at least 35%, at least 40%, at least 45%, at least 50%, at least 55%, at least 65%, at least 70%, at least 75%, at least 80%, at least 85%, at least 95%, or at least 100%, compared to a virus which does not comprise the modification that activates or enhances MHC II presentation, but is otherwise identical.

The modification causing activation or enhancement of MHC II presentation can include insertion of one or more genes selected from the group consisting of: an apoptosis inhibitor protein or a necrotic cell death activator protein; an autophagy enhancer protein; an asparaginyl endopeptidase; a class II transactivator (CIITA); an interferon-gamma; a Toll-like receptors (TLR) activator; a dendritic cell (DC) maturation activator (e.g., osteopontin or TNF-alpha). In certain instances, the MHC II enhancer may be modified to include secretory sequences and cell permeability domains to provide an immunological bystander effect. In some cases, the autophagy enhancer protein comprises HMGB1, PIAS3, LIGHT, ITAC, a fractalkine, a functional domain or fragment or variant thereof, or any combinations thereof. In some cases, the autophagy enhancer protein comprises HMGB1. In some cases, the HMGB1 comprises a nucleic acid sequence as set forth in SEQ ID NO: 4 or an amino acid sequence set forth in SEQ ID NO: 5. In some cases, the secretory sequence comprises an IgE-derived signal sequence. In some cases, the IgE-derived signal sequence comprises a nucleic acid sequence as set forth in SEQ ID NO: 6 or an amino acid sequence set forth in SEQ ID NO: 7. In some cases, the HMGB1 is modified with an IgE-derived signal sequence, wherein the modified HMGB1 comprises a nucleic acid sequence as set forth in SEQ ID NO: 8 or an amino acid sequence as set forth in SEQ ID NO: 9.

Concurrent MHC II upregulation (which ideally occurs in non-infected cells, but that is not a requirement) leads to more efficient targeting of tumor antigens (MHC II down-regulation is one of the common tumor resistance mechanisms to anti-PD1/PDL1 antibodies for example).

Provided herein are modifications of the recombinant oncolytic virus that provide for inhibition or partial inhibition of MHC I presentation as described herein, and further provide for activation of MHC II presentation as described herein. In some instances, modifications are in separate locations in the genome. In some instances, modifications are in the same location in the genome. In some instances, modifications are in adjacent locations in the genome.

Other Multiple Modifications

Provided herein in some embodiments are vaccines comprising recombinant oncolytic viruses with insertions, mutations or deletions in the viral genome (also referred to herein as the viral backbone). In the case of oncolytic vaccinia viruses, they are preferably recombinant or selected to have low toxicity and to accumulate in the target tissue. In some embodiments, the modifications in the viral backbone/viral genome are modifications that render the vaccinia virus non-replicating or comprise a poor replicative capacity. Non-limiting examples of such modifications can include mutations in the following viral genes: TK, A1, A2, VH1, A33, I7, F13L, A36R, A34R, A46R, A49R, B8R, B14R, B15R, B18R, C12L, C4, C16, SPI-1, SPI-2, B15R, VGF, E3L, K1L, K3L, K7R, A41L, M2L, N1L, A52R, a functional domain or fragment or a variant thereof, or any combinations thereof.

In some embodiments, concerning the vaccinia virus, the viral backbone mutation is selected from the group consisting of: a complete or partial deletion of the A52R gene; a complete or partial deletion of the TK gene; a complete or partial deletion of the F13L gene; a complete or partial deletion of the A36R gene; a complete or partial deletion of the A34R gene; a complete or partial deletion of the B8R gene; gene; a complete or partial deletion of the B18R gene; a complete or partial deletion of the C12L gene; a complete or partial deletion of the C4 gene; a complete or partial deletion of the C16 gene; a complete or partial deletion of the SPI-1 gene; a complete or partial deletion of the SPI-2 gene; a complete or partial deletion of the VGF gene; a complete or partial deletion of the E3L gene; a complete or partial deletion of the K3L gene; a complete or partial deletion of the A41L gene; gene; a complete or partial deletion of the a complete or partial deletion of the A52R gene; a complete or partial deletion of the B15R gene; a complete or partial deletion of the K7R gene; a complete or partial deletion of the B14R gene; a complete or partial deletion of the N1L gene; a complete or partial deletion of the K1L gene; a complete or partial deletion of the M2L gene; a complete or partial deletion of the A49R gene; a complete or partial deletion of the VH1 gene; a complete or partial deletion of A33 gene; a complete or partial deletion of A1; a complete or partial deletion of A2 gene; a complete or partial deletion of 17 gene, and a complete or partial deletion of the A46R gene. As used herein, the reference to a viral gene can be made by reference to the protein encoded by the gene (e.g., A33 gene can mean a gene that codes for the A33 protein).

In some embodiments, the viral backbone mutation of the oncolytic virus, including any combinations of substitution, insertion, and deletion, can result in a sequence with less than 100%, 99%, 98%, 97%, 96%, 95%, 94%, 93%, 92%, 91%, 90% or less sequence homology to the wild-type sequence of the viral gene or a viral protein coded by the gene. The viral gene and protein coded by the same, in some embodiments, is selected from the group consisting of: TK, A1, A2, VH1, A33, I7, F13L, A36R, A34R, A46R, A49R, B8R, B14R, B15R, B18R, C12L, C4, C16, SPI-1, SPI-2, B15R, VGF, E3L, K1L, K3L, K7R, A41L, M2L, N1L, and A52R.

In some embodiments, the viral backbone can comprise 1, 2, 3, 4, 5, or more mutations in the amino acid sequence of the viral protein (e.g., a viral antigen). The viral antigen is in some examples selected from the group consisting of: TK, A1, A2, VH1, A33, I7, F13L, A36R, A34R, A46R, A49R, B8R, B14R, B15R, B18R, C12L, C4, C16, SPI-1, SPI-2, B15R, VGF, E3L, K1L, K3L, K7R, A41L, M2L, N1L, and A52R.

The disclosure provides in some embodiments, recombinant oncolytic viruses comprising one more mutation in the genome of the virus (virus back bone) such that the mutation increases the T-cell arm of the immune response. A mutation may be addition, deletion or substitution of one or more nucleic acid in the viral genome (wild type or attenuated native strains of oncolytic virus).

In non-limiting examples, the mutation can be complete or partial deletion of genes that are known to inhibit cytokines involved in the Th1 immune response. As non-limiting examples the mutation may be deletion of nucleic acid encoding B8R (interferon gamma (IFN-g) binding proteins); C12L (interleukin-18 (IL-18) binding proteins).

In further non-limiting example, the mutation can be complete or partial deletion of genes in innate immune signaling. As non-limiting examples the mutation may be deletion of nucleic acid encoding B18R (type I interferon (IFN)-binding proteins); A52R (nuclear factor κB (NF-κB) inhibitor proteins); E3L (protein kinase (PKR) inhibitors); C4, C16 (STING pathway inhibitors).

In further non-limiting example, the mutation can be complete or partial deletion of genes encoding proteins for inhibition of other components of the immune response. As non-limiting examples the mutation may be a complete or partial deletion of nucleic acid encoding B15, K7, B14, N1, K1, M2, A49, VH1, A46 or combination thereof. The viral backbone mutation may also include substituting the oncolytic virulence genes with mostly potent genes of equivalent function from other poxviruses.

Amino acid sequence variants of the polypeptides of the present disclosure can be substitutional, insertional or deletion variants. A mutation in a gene encoding a viral polypeptide may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500 or more non-contiguous or contiguous amino acids of the polypeptide, as compared to wild-type.

Deletion variants may lack one or more residues of the native or wild-type protein. Individual residues can be deleted or all or part of a domain (such as a catalytic or binding domain) can be deleted. A stop codon may be introduced (by substitution or insertion) into an encoding nucleic acid sequence to generate a truncated protein. Insertional mutants typically involve the addition of material at a non-terminal point in the polypeptide. This may include the insertion of an immunoreactive epitope or simply one or more residues. Terminal additions, called fusion proteins, may also be generated.

Substitutional variants typically comprise the exchange of one amino acid for another at one or more sites within the protein and may be designed to modulate one or more properties of the polypeptide, with or without the loss of other functions or properties. Substitutions may be conservative, that is, one amino acid is replaced with one of similar shape and charge. Conservative substitutions can include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

The oncolytic viruses provided herein comprise additional insertions, mutations, deletions or substitutions in the viral genome. An oncolytic virus may comprise one or more additional insertions or partial insertions of exogenous nucleic acids that code for one or more of chemokine receptor, TRIF protein or a functional domain thereof, or one or more of leptin, interleukin-2 (IL2), interleukin-15/interleukin-15Ra (IL15/IL15Ra), interleukin-7 (IL-7), leptin-interleukin fusion protein (e.g. leptin-IL2 fusion protein shown in example 1 as L2). In some cases, the nucleic acid encodes for an IL15 amino acid sequence as set forth in SEQ ID NO: 10. In some cases, the nucleic acid encodes for an IL-7 amino acid sequence as set forth in any of SEQ ID NOs: 13 or 14. Modifications such as insertion of chemokine receptor is insertion of wild type and/or mutant type CCL5, CXCR4, CCR2, CCL2. In some cases, the nucleic acid encodes for a CXCR4 amino acid sequence as set forth in any one of SEQ ID NOs: 18-20. In some cases, the nucleic acid encodes for a CXCR4 amino acid sequence as set forth in SEQ ID NO: 18. In some cases, the nucleic acid encodes for a CCR2 amino acid sequence as set forth in any one of SEQ ID NOs: 23-24. An oncolytic virus may further comprise one or more additional deletions or partial deletions of one or more genes from TK, A1, A2, VH1, A33, I7, F13L, A36R, A34R, A46R, A49R, B8R, B14R, B15R, B18R, C12L, C4, C16, SPI-1, SPI-2, B15R, VGF, E3L, K1L, K3L, K7R, A41L, M2L, N1L, A52R a functional domain or fragment or variant thereof, or any combinations thereof. In some cases, the oncolytic virus provided herein can comprise a complete or partial deletion of the A52R gene and an insertion of a chemokine receptor, such as CCR2. In some cases, the oncolytic virus provided herein can comprise a complete or partial deletion of the A52R gene and an insertion of a chemokine receptor, such as CCR2. In some cases, the oncolytic virus provided herein can comprise a complete or partial deletion of at least one of: A52R or TK viral genes, and insertion of an exogenous nucleic acid encoding a fusion protein (e.g., a metabolic modulator protein fused to a cytokine, such as Leptin-IL2 fusion protein).

Hyaluronan (1-IA) is a structural element of ECM and a high molecular weight linear glycosaminoglycan consisting of repeating disaccharide units. It can be distributed widely throughout connective, epithelial, and neural tissues, and its expression level can be significantly elevated in many types of tumors. Hyaluronidases are a family of enzymes that catalyze the degradation of HA. There are at least five functional hyaluronidases identified so far in human: HYAL1, HYAL2, HYAL3, HYAL4 and HYAL5 (also known as PH-20 or SPAM1), among which PH-20 is the only one known so far to be functional at relatively neutral pH. In some cases of the present disclosure, combining hyaluronidase with other tumor-targeting therapeutic agents (such as transgenes, also referred to herein as exogenous nucleic acid) can promote the therapeutic effect of the modified oncolytic virus at least by diminishing the ECM and enhancing the transportation of the therapeutic agent inside and between the tumors.

Some embodiments herein disclose a modified oncolytic virus that can comprise an exogenous nucleic acid coding for a membrane associated protein that is capable of degrading hyaluronan, such as a hyaluronidase. It should be noted that the term "hyaluronidase" as used herein can refer to any enzyme or a fragment thereof that catalyzes the degradation of HA in a tumor, including, but not limited to, PH-20 and its homologs from other species, as well as other engineered/design proteins with similar enzymatic function. As used herein, hyaluronidase can refer to a class of hyaluronan degrading enzymes. In some cases, the PH-20 comprises an amino acid sequence as described by SEQ ID NO: 26. In some cases the hyaluronidase comprises an amino acid sequence as set forth in SEQ ID NO: 28. In some cases, the hyaluronidase additionally comprises a secretory sequence. In some cases, the secretory sequence comprises an IgE-derived signal sequence. In some cases, the IgE-derived signal sequence comprises the amino acid sequence as set forth in SEQ ID NO: 7. In some cases, the hyaluronidase with IgE-derived signal sequence comprises the nucleic acid sequence set forth in SEQ ID NO: 29 or the amino acid sequence as set forth in SEQ ID NO: 30.

Vaccines, Pharmaceutical Compositions, and Delivery of Recombinant Vaccinia Viruses The present disclosure further provides for pharmaceutical or an immunogenic composition for treatment of a cancer. In addition, the present disclosure further provides, in some embodiments, pharmaceutical or an immunogenic composition that can include a vaccine comprising a recombinant vaccinia virus as described above and suitable carriers. The vaccine can be provided as a kit which include the recombinant vaccinia virus-based vaccine as described above or a pharmaceutical composition of recombinant vaccinia virus-based vaccine as described above. The pharmaceutical compositions for vaccine delivery can be for parenteral or oral delivery or nasal delivery. The pharmaceutical compositions can be administered to a human at least once. The pharmaceutical compositions can be administered to the human more than once.

Also provided herein are recombinant vaccinia viruses, compositions, and/or vaccines comprising a recombinant vaccinia virus for use as a medicament or vaccine.

In some embodiments, a pharmaceutical composition comprising a vaccine comprising a recombinant vaccinia virus as provided herein can be administered to a subject at a dose of $10^6$ to $10^9$ PFU, at a dose of $10^6$ to $5\times10^8$ PFU, or $10^7$ to $10^8$ PFU. The recombinant vaccinia viruses provided herein may also be administered to a subject at a dose of $10^6$, $10^7$ PFU, $10^8$, or $5\times10^8$ PFU. The recombinant vaccinia viruses provided herein can be administered to a human subject at a dose of $10^7$ PFU, $10^8$ PFU, or $5\times10^8$ PFU.

A recombinant vaccinia virus, a vaccine composition, or a pharmaceutical composition as described herein can be formulated in a solution in a concentration range of $10^4$ to $10^9$ PFU/mL, $10^5$ to $5\times10^8$ PFU/mL, $10^6$ to $10^8$ PFU/mL, or $10^7$ to $10^8$ PFU/mL. In some embodiments, a vaccination dose for humans can comprise from about $10^6$ to $10^9$ PFU, including a dose of about $10^6$ PFU, about $10^7$ PFU, or about $10^8$ PFU. In some embodiments, the dose for humans can comprise at least about $2\times10^7$ PFU, at least about $3\times10^7$ PFU, at least about $5\times10^7$ PFU, at least about $1\times10^8$ PFU, at least about $2\times10^8$ PFU, in a volume of 0.1 to 0.5 ml.

The pharmaceutical/immunogenic compositions provided herein may generally include one or more pharmaceutically acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycolic acids, polymeric amino acids, amino acid copolymers, lipid aggregates, or the like.

A homologous prime-boost regimen may be employed wherein a recombinant vaccinia virus as defined herein can be administered in a first dosage. One or more subsequent administrations of a recombinant vaccinia virus as defined herein can be given to boost the immune response provided in the first administration. In some embodiments, the one or more antigens delivered by a recombinant vaccinia virus can be the same or similar to those of the first administration.

A pharmaceutical composition comprising a recombinant vaccinia virus as provided herein can be administered to the subject in a single dose, or in multiple (such as 2, 3, 4, etc.) doses. The recombinant vaccinia virus can be administered in a first (priming) and second (boosting) administration. The first dose can comprise from about $10^6$ to about $10^9$ PFU/mL of a recombinant vaccinia virus and the second dose can comprise from about $10^6$ to about $10^9$ PFU/mL of recombinant vaccinia virus. The first and second dose can comprise at least 1000 PFU/mL of the modified vaccine virus.

The second dose of the vaccine or the pharmaceutical/immunogenic composition can be administered from 24 hours to about 3 months, such as from about 7 days to about 2 months, after the administration of the first dose. The second dose can be a booster dose.

The recombinant vaccinia virus or a pharmaceutical/immunogenic composition comprising a recombinant vaccinia virus can be administered intraperitoneally systemically, locally, parenterally, subcutaneously, intravenously, intramuscularly, or intranasally. The vaccine can be administered with an adjuvant, such as an adjuvant as described herein.

Another aspect of this disclosure relates to a method for affecting an immune response in a subject comprising administering to the subject a recombinant vaccinia virus as escribed herein, a vaccine comprising the same, or a pharmaceutical/immunogenic composition comprising the recombinant vaccinia virus or the vaccine compositions as described herein.

An immunization protocol may include immunization with more than one antigen together in a single dose of the vaccine, multiple doses, and multiple doses with different antigens in each dose. In some embodiments, an immunization protocol may include immunization with an antigen and an adjuvant. Adjuvants, in the present context, can include cytokines and other immunomodulatory molecules such as TLR (toll like receptor) agonists and their derivatives that stimulate the immune response.

Also provided herein are method of treating a disease, disorder, or condition by administering a recombinant vaccinia virus as described herein. In some embodiments, amount of a recombinant vaccinia virus of this disclosure administered to a subject can be between about $10^3$ and $10^{12}$ infectious viral particles or plaque forming units (PFU), or between about $10^5$ and $10^{10}$ PFU, or between about $10^5$ and $10^8$ PFU, or between about $10^8$ and $10^{10}$ PFU. In some embodiments, the amount of a recombinant vaccinia virus of this disclosure administered to a subject can be between about $10^3$ and $10^{12}$ viral particles or plaque forming units (PFU), or between about $10^5$ and $10^{10}$ PFU, or between about $10^5$ and $10^8$ PFU, or between about $10^8$ and $10^{10}$ PFU. In some embodiments, a recombinant vaccinia virus of this disclosure can be administered at a dose that can comprise about $10^3$ PFU/dose to about $10^4$ PFU/dose, about $10^4$ PFU/dose to about $10^5$ PFU/dose, about $10^5$ PFU/dose to about $10^6$ PFU/dose, about $10^7$ PFU/dose to about $10^8$ PFU/dose, about $10^9$ PFU/dose to about $10^{10}$ PFU/dose, about $10^{10}$ PFU/dose to about $10^{11}$ PFU/dose, about $10^{11}$ PFU/dose to about $10^{12}$ PFU/dose, about $10^{12}$ PFU/dose to about $10^{13}$ PFU/dose, about $10^{13}$ PFU/dose to about $10^{14}$ PFU/dose, or about $10^{14}$ PFU/dose to about $10^{15}$ PFU/dose. In some embodiments, a recombinant vaccinia virus of this disclosure can be administered at a dose that can comprise about $2\times10^3$ PFU/dose, $3\times10^3$ PFU/dose, $4\times10^3$ PFU/dose, $5\times10^3$ PFU/dose, $6\times10^3$ PFU/dose, $7\times10^3$ PFU/dose, $8\times10^3$ PFU/dose, $9\times10^3$ PFU/dose, about $10^4$ PFU/dose, about $2\times10^4$ PFU/dose, about $3\times10^4$ PFU/dose, about $4\times10^4$ PFU/dose, about $5\times10^4$ PFU/dose, about $6\times10^4$ PFU/dose, about $7\times10^4$ PFU/dose, about $8\times10^4$ PFU/dose, about $9\times10^4$ PFU/dose, about $10^5$ PFU/dose, $2\times10^5$ PFU/dose, $3\times10^5$ PFU/dose, $4\times10^5$ PFU/dose, $5\times10^5$ PFU/dose, $6\times10^5$ PFU/dose, $7\times10^5$ PFU/dose, $8\times10^5$ PFU/dose, $9\times10^5$ PFU/dose, about $10^6$ PFU/dose, about $2\times10^6$ PFU/dose, about $3\times10^6$ PFU/dose, about $4\times10^6$ PFU/dose, about $5\times10^6$ PFU/dose, about $6\times10^6$ PFU/dose, about $7\times10^6$ PFU/dose, about $8\times10^6$ PFU/dose, about $9\times10^6$ PFU/dose, about $10^7$ PFU/dose, about $2\times10^7$ PFU/dose, about $3\times10^7$ PFU/dose, about $4\times10^7$ PFU/dose, about $5\times10^7$ PFU/dose, about $6\times10^7$ PFU/dose, about $7\times10^7$ PFU/dose, about $8\times10^7$ PFU/dose, about $9\times10^7$ PFU/dose, about $10^8$ PFU/dose, about $2\times10^8$ PFU/dose, about $3\times10^8$ PFU/dose, about $4\times10^8$ PFU/dose, about $5\times10^8$ PFU/dose, about $6\times10^8$ PFU/dose, about $7\times10^8$ PFU/dose, about $8\times10^8$ PFU/dose, about $9\times10^8$ PFU/dose, about $10^9$ PFU/dose, about $2\times10^9$ PFU/dose, about $3\times10^9$ PFU/dose, about $4\times10^9$ PFU/dose, about $5\times10^9$ PFU/dose, about $6\times10^9$ PFU/dose, about $7\times10^9$ PFU/dose, about $8\times10^9$ PFU/dose, about $9\times10^9$ PFU/dose, about $10^{10}$ PFU/dose, about $2\times10^{10}$ PFU/dose, about $3\times10^{10}$ PFU/dose, about $4\times10^{10}$ PFU/dose, about $5\times10^{10}$ PFU/dose, about $6\times10^{10}$ PFU/dose, about 7×10$^{10}$ PFU/dose, about 8×10$^{10}$ PFU/dose, about 9×10$^{10}$ PFU/dose, about 10$^{10}$ PFU/dose, about 2×10$^{10}$ PFU/dose, about 3×10$^{10}$ PFU/dose, about 4×10$^{10}$ PFU/dose, about 5×10$^{10}$ PFU/dose, about 6×10$^{10}$ PFU/dose, about 7×10$^{10}$ PFU/dose, about 8×10$^{10}$ PFU/dose, about 9×10$^{10}$ PFU/dose, about 10$^{11}$ PFU/dose, about 2×10$^{11}$ PFU/dose, about 3×10$^{11}$ PFU/dose, about 4×10$^{11}$ PFU/dose, about 5×10$^{11}$ PFU/dose, about 6×10$^{11}$ PFU/dose, about 7×10$^{11}$ PFU/dose, about 8×10$^{11}$ PFU/dose, about 9×10$^{11}$ PFU/dose, or about 10$^{12}$ PFU/dose, about 10$^{12}$ PFU/dose to about 10$^{13}$ PFU/dose, about 10$^{13}$ PFU/dose to about 10$^{14}$ PFU/dose, or about 10$^{14}$ PFU/dose to about 10$^{15}$ PFU/dose. In some embodiments, a recombinant vaccinia virus of this disclosure can be administered at a dose that can comprise 3×10$^9$ PFU/dose. In some embodiments, a modified oncolytic vaccinia virus of this disclosure can be administered at a dose that can comprise up to 5×10$^9$ PFU/dose.

In some embodiments, a recombinant vaccinia virus of this disclosure, can be administered at a dose that can comprise about 10$^3$ viral particles/dose to about 10$^4$ viral particles/dose, about 10$^4$ viral particles/dose to about 10$^5$ viral particles/dose, about 10$^5$ viral particles/dose to about 10$^6$ viral particles/dose, about 10$^7$ viral particles/dose to about 10$^8$ viral particles/dose, about 10$^9$ viral particles/dose to about 10$^{10}$ viral particles/dose, about 10$^{10}$ viral particles/dose to about 10$^{11}$ viral particles/dose, about 10$^{11}$ viral particles/dose to about 10$^{12}$ viral particles/dose, about 10$^{12}$ viral particles/dose to about 10$^{13}$ viral particles/dose, about 10$^{13}$ viral particles/dose to about 10$^{14}$ viral particles/dose, or about 10$^{14}$ viral particles/dose to about 10$^{15}$ viral particles/dose.

In some embodiments, a recombinant vaccinia virus of this disclosure can be administered at a dose that can comprise about 10$^3$ PFU/kg to about 10$^4$ PFU/kg, about 10$^4$ PFU/kg to about 10$^5$ PFU/kg, about 10$^5$ PFU/kg to about 10$^6$ PFU/kg, about 10$^7$ PFU/kg to about 10$^8$ PFU/kg, about 10$^9$ PFU/kg to about 10$^{10}$ PFU/kg, about 10$^{10}$ PFU/kg to about 10$^{11}$ PFU/kg, about 10$^{11}$ PFU/kg to about 10$^{12}$ PFU/kg, about 10$^{12}$ PFU/kg to about 10$^{13}$ PFU/kg, about 10$^{13}$ PFU/kg to about 10$^{14}$ PFU/kg, or about 10$^{14}$ PFU/kg to about 10$^{15}$ PFU/kg. In some embodiments, a modified oncolytic vaccinia virus of this disclosure can be administered at a dose that can comprise about 2×10$^3$ PFU/kg, 3×10$^3$ PFU/kg, 4×10$^3$ PFU/kg, 5×10$^3$ PFU/kg, 6×10$^3$ PFU/kg, 7×10$^3$ PFU/kg, 8×10$^3$ PFU/kg, 9×10$^3$ PFU/kg, about 10$^4$ PFU/kg, 2×10$^4$ PFU/kg, about 3×10$^4$ PFU/kg, about 4×10$^4$ PFU/kg, about 5×10$^4$ PFU/kg, about 6×10$^4$ PFU/kg, about 7×10$^4$ PFU/kg, about 8×10$^4$ PFU/kg, about 9×10$^4$ PFU/kg, about 10$^5$ PFU/kg, 2×10$^5$ PFU/kg, 3×10$^5$ PFU/kg, 4×10$^5$ PFU/kg, 5×10$^5$ PFU/kg, 6×10$^5$ PFU/kg, 7×10$^5$ PFU/kg, 8×10$^5$ PFU/kg, 9×10$^5$ PFU/kg, about 10$^6$ PFU/kg, about 2×10$^6$ PFU/kg, about 3×10$^6$ PFU/kg, about 4×10$^6$ PFU/kg, about 5×10$^6$ PFU/kg, about 6×10$^6$ PFU/kg, about 7×10$^6$ PFU/kg, about 8×10$^6$ PFU/kg, about 9×10$^6$ PFU/kg, about 10$^7$ PFU/kg, about 2×10$^7$ PFU/kg, about 3×10$^7$ PFU/kg, about 4×10$^7$ PFU/kg, about 5×10$^7$ PFU/kg, about 6×10$^7$ PFU/kg, about 7×10$^7$ PFU/kg, about 8×10$^7$ PFU/kg, about 9×10$^7$ PFU/kg, about 10$^8$ PFU/kg, about 2×10$^8$ PFU/kg, about 3×10$^8$ PFU/kg, about 4×10$^8$ PFU/kg, about 5×10$^8$ PFU/kg, about 6×10$^8$ PFU/kg, about 7×10$^8$ PFU/kg, about 8×10$^8$ PFU/kg, about 9×10$^8$ PFU/kg, about 10$^9$ PFU/kg, about 2×10$^9$ PFU/kg, about 3×10$^9$ PFU/kg, about 4×10$^9$ PFU/kg, about 5×10$^9$ PFU/kg, about 6×10$^9$ PFU/kg, about 7×10$^9$ PFU/kg, about 8×10$^9$ PFU/kg, about 9×10$^9$ PFU/kg, about 10$^{10}$ PFU/kg, about 2×10$^{10}$ PFU/kg, about 3×10$^{10}$ PFU/kg, about 4×10$^{10}$ PFU/kg, about 5×10$^{10}$ PFU/kg, about 6×10$^{10}$ PFU/kg, about 7×10$^{10}$ PFU/kg, about 8×10$^{10}$ PFU/kg, about 9×10$^{10}$ PFU/kg, about 10$^{10}$ PFU/kg, about 2×10$^{10}$ PFU/kg, about 3×10$^{10}$ PFU/kg, about 4×10$^{10}$ PFU/kg, about 5×10$^{10}$ PFU/kg, about 6×10$^{10}$ PFU/kg, about 7×10$^{10}$ PFU/kg, about 8×10$^{10}$ PFU/kg, about 9×10$^{10}$ PFU/kg, about 10$^{11}$ PFU/kg, about 2×10$^{11}$ PFU/kg, about 3×10$^{11}$ PFU/kg, about 4×10$^{11}$ PFU/kg, about 5×10$^{11}$ PFU/kg, about 6×10$^{11}$ PFU/kg, about 7×10$^{11}$ PFU/kg, about 8×10$^{11}$ PFU/kg, about 9×10$^{11}$ PFU/kg, or about 10$^{12}$ PFU/kg, about 10$^{12}$ PFU/kg to about 10$^{13}$ PFU/kg, about 10$^{13}$ PFU/kg to about 10$^{14}$ PFU/kg, or about 10$^{14}$ PFU/kg to about 10$^{15}$ PFU/kg. In some embodiments, a recombinant vaccinia virus of this disclosure can be administered at a dose that can comprise 3×10$^9$ PFU/kg. In some embodiments, a recombinant vaccinia virus of this disclosure can be administered at a dose that can comprise up to 5×10$^9$ PFU/kg.

In some embodiments, a recombinant vaccinia virus of this disclosure can be administered at a dose that can comprise about 10$^3$ viral particles/kg to about 10$^4$ viral particles/kg, about 10$^4$ viral particles/kg to about 10$^5$ viral particles/kg, about 10$^5$ viral particles/kg to about 10$^6$ viral particles/kg, about 10$^7$ viral particles/kg to about 10$^8$ viral particles/kg, about 10$^9$ viral particles/kg to about 10$^{10}$ viral particles/kg, about 10$^{10}$ viral particles/kg to about 10$^{11}$ viral particles/kg, about 10$^{11}$ viral particles/kg to about 10$^{12}$ viral particles/kg, about 10$^{12}$ viral particles/kg to about 10$^{13}$ viral particles/kg, about 10$^{13}$ viral particles/kg to about 10$^{14}$ viral particles/kg, or about 10$^{14}$ viral particles/kg to about 10$^{15}$ viral particles/kg.

A liquid dosage form of a recombinant vaccinia virus as described herein can comprise, in certain embodiments, a viral dose of about 10$^3$ PFU/mL to about 10$^4$ PFU/mL, about 10$^4$ PFU/mL to about 10$^5$ PFU/mL, about 10$^5$ PFU/mL to about 10$^6$ PFU/mL, about 10$^7$ PFU/mL to about 10$^8$ PFU/mL, about 10$^9$ PFU/mL to about 10$^{10}$ PFU/mL, about 10$^{10}$ PFU/mL to about 10$^{11}$ PFU/mL, about 10$^{11}$ PFU/mL to about 10$^{12}$ PFU/mL, about 10$^{12}$ PFU/mL to about 10$^{13}$ PFU/mL, about 10$^{13}$ PFU/mL to about 10$^{14}$ PFU/mL, or about 10$^{14}$ PFU/mL to about 10$^{15}$ PFU/mL. In some embodiments, a recombinant vaccinia virus of this disclosure can be administered at a dose that can comprise about 2×10$^3$ PFU/mL, 3×10$^3$ PFU/mL, 4×10$^3$ PFU/mL, 5×10$^3$ PFU/mL, 6×10$^3$ PFU/mL, 7×10$^3$ PFU/mL, 8×10$^3$ PFU/mL, 9×10$^3$ PFU/mL, about 10$^4$ PFU/mL, about 2×10$^4$ PFU/mL, about 3×10$^4$ PFU/mL, about 4×10$^4$ PFU/mL, about 5×10$^4$ PFU/mL, about 6×10$^4$ PFU/mL, about 7×10$^4$ PFU/mL, about 8×10$^4$ PFU/mL, about 9×10$^4$ PFU/mL, about 10$^5$ PFU/mL, 2×10$^5$ PFU/mL, 3×10$^5$ PFU/mL, 4×10$^5$ PFU/mL, 5×10$^5$ PFU/mL, 6×10$^5$ PFU/mL, 7×10$^5$ PFU/mL, 8×10$^5$ PFU/mL, 9×10$^5$ PFU/mL, about 10$^6$ PFU/mL, about 2×10$^6$ PFU/mL, about 3×10$^6$ PFU/mL, about 4×10$^6$ PFU/mL, about 5×10$^6$ PFU/mL, about 6×10$^6$ PFU/mL, about 7×10$^6$ PFU/mL, about 8×10$^6$ PFU/mL, about 9×10$^6$ PFU/mL, about 10$^7$ PFU/mL, about 2×10$^7$ PFU/mL, about 3×10$^7$ PFU/mL, about 4×10$^7$ PFU/mL, about 5×10$^7$ PFU/mL, about 6×10$^7$ PFU/mL, about 7×10$^7$ PFU/mL, about 8×10$^7$ PFU/mL, about 9×10$^7$ PFU/mL, about 10$^8$ PFU/mL, about 2×10$^8$ PFU/mL, about 3×10$^8$ PFU/mL, about 4×10$^8$ PFU/mL, about 5×10$^8$ PFU/mL, about 6×10$^8$ PFU/mL, about 7×10$^8$ PFU/mL, about 8×10$^8$ PFU/mL, about 9×10$^8$ PFU/mL, about 10$^9$ PFU/mL, about 2×10$^9$ PFU/mL, about 3×10$^9$ PFU/mL, about 4×10$^9$ PFU/mL, about 5×10$^9$ PFU/mL, about 6×10$^9$ PFU/mL, about 7×10$^9$ PFU/mL, about 8×10$^9$ PFU/mL, about 9×10$^9$ PFU/mL, about 10$^{10}$ PFU/mL, about 2×10$^{10}$ PFU/mL, about 3×10$^{10}$ PFU/mL, about 4×10$^{10}$ PFU/mL, about 5×10$^{10}$ PFU/mL, about 6×10$^{10}$ PFU/mL, about 7×10$^{10}$ PFU/mL, about 8×10$^{10}$ PFU/mL, about 9×10$^{10}$ PFU/mL, about 10$^{10}$ PFU/mL, about 2×10$^{10}$ PFU/mL, about $3 \times 10^{10}$ PFU/mL, about $4 \times 10^{10}$ PFU/mL, about $5 \times 10^{10}$ PFU/mL, about $6 \times 10^{10}$ PFU/mL, about $7 \times 10^{10}$ PFU/mL, about $8 \times 10^{10}$ PFU/mL, about $9 \times 10^{10}$ PFU/mL, about $10^{11}$ PFU/mL, about $2 \times 10^{11}$ PFU/mL, about $3 \times 10^{11}$ PFU/mL, about $4 \times 10^{11}$ PFU/mL, about $5 \times 10^{11}$ PFU/mL, about $6 \times 10^{11}$ PFU/mL, about $7 \times 10^{11}$ PFU/mL, about $8 \times 10^{11}$ PFU/mL, about $9 \times 10^{11}$ PFU/mL, or about $10^{12}$ PFU/mL, about $10^{12}$ PFU/mL to about $10^{13}$ PFU/mL, about $10^{13}$ PFU/mL to about $10^{14}$ PFU/mL, or about $10^{14}$ PFU/mL to about $10^{15}$ PFU/mL. In some embodiments, a recombinant vaccinia virus of this disclosure can be administered at a dose that can comprise $5 \times 10^9$ PFU/mL. In some embodiments, a recombinant vaccinia virus of this disclosure can be administered at a dose that can comprise up to $5 \times 10^9$ PFU/mL.

In some instances, where the recombinant vaccinia virus can be administered by an injection, the dosage can comprise about $10^3$ viral particles per injection, $10^4$ viral particles per injection, $10^5$ viral particles per injection, $10^6$ viral particles per injection, $10^7$ viral particles per injection, $10^8$ viral particles per injection, $10^9$ viral particles per injection, $10^{10}$ viral particles per injection, $10^{11}$ viral particles per injection, $10^{12}$ viral particles per injection, $2 \times 10^{12}$ viral particles per injection, $10^{13}$ viral particles per injection, $10^{14}$ viral particles per injection, or $10^{15}$ viral particles per injection. In further instances, where the recombinant vaccinia virus is administered by an injection, the dosage can comprise about $10^3$ infectious viral particles per injection, $10^4$ infectious viral particles per injection, $10^5$ infectious viral particles per injection, $10^6$ infectious viral particles per injection, $10^7$ infectious viral particles per injection, $10^8$ infectious viral particles per injection, $10^9$ infectious viral particles per injection, $10^{10}$ infectious viral particles per injection, $10^{11}$ infectious viral particles per injection, $10^{12}$ infectious viral particles per injection, $2 \times 10^{12}$ infectious viral particles per injection, $10^{13}$ infectious viral particles per injection, $10^{14}$ infectious viral particles per injection, or $10^{15}$ infectious viral particles per injection. Note that herein $10^x$ is alternatively expressed as 1 eX. In certain embodiments, the recombinant vaccinia virus can be administered in one or more doses. In certain embodiments, the virus can be administered in an amount sufficient to induce oncolysis in at least about 20% of cells in a tumor, in at least about 30% of cells in a tumor, in at least about 40% of cells in a tumor, in at least about 50% of cells in a tumor, in at least about 60% of cells in a tumor, in at least about 70% of cells in a tumor, in at least about 80% of cells in a tumor, or in at least about 90% of cells in a tumor.

In certain embodiments, a single dose of recombinant virus can refer to the amount administered to a subject or a tumor over a 1, 2, 5, 10, 15, 20, or 24-hour period. In certain embodiments, the dose can be spread over time or by separate injection. In certain embodiments, multiple doses (e.g., 2, 3, 4, 5, 6 or more doses) of the vaccinia virus can be administered to the subject, for example, where a second treatment can occur within 1, 2, 3, 4, 5, 6, 7 days or weeks of a first treatment. In certain embodiments, multiple doses of the modified oncolytic v can be administered to the subject over a period of 1, 2, 3, 4, 5, 6, 7 or more days or weeks. In certain embodiments, the recombinant vaccinia virus or the pharmaceutical composition as described herein can be administered over a period of about 1 week to about 2 weeks, about 2 weeks to about 3 weeks, about 3 weeks to about 4 weeks, about 4 weeks to about 5 weeks, about 6 weeks to about 7 weeks, about 7 weeks to about 8 weeks, about 8 weeks to about 9 weeks, about 9 weeks to about 10 weeks, about 10 weeks to about 11 weeks, about 11 weeks to about 12 weeks, about 12 weeks to about 24 weeks, about 24 weeks to about 48 weeks, about 48 weeks or about 52 weeks, or longer. The frequency of administration of the recombinant virus or the pharmaceutical composition as described herein can be, in certain instances, once daily, twice daily, once every week, once every three weeks, once every four weeks (or once a month), once every 8 weeks (or once every 2 months), once every 12 weeks (or once every 3 months), or once every 24 weeks (once every 6 months). In some embodiments of the methods disclosed herein, the recombinant vaccinia virus or the pharmaceutical composition can be administered, independently, in an initial dose for a first period of time, an intermediate dose for a second period of time, and a high dose for a third period of time. In some embodiments, the initial dose can be lower than the intermediate dose and the intermediate dose can be lower than the high dose. In some embodiments of the methods disclosed herein, the recombinant vaccinia virus or the pharmaceutical composition can be administered, independently, in a high dose for a first period of time, an intermediate dose for a second period of time, and a low dose for a third period of time. In some embodiments, the initial dose can be higher than the intermediate dose and the intermediate dose can be higher than the low dose. In some embodiments, the first, second, and third periods of time can be, independently, about 1 week to about 2 weeks, about 2 weeks to about 3 weeks, about 3 weeks to about 4 weeks, about 4 weeks to about 5 weeks, about 6 weeks to about 7 weeks, about 7 weeks to about 8 weeks, about 8 weeks to about 9 weeks, about 9 weeks to about 10 weeks, about 10 weeks to about 11 weeks, about 11 weeks to about 12 weeks, about 12 weeks to about 24 weeks, about 24 weeks to about 48 weeks, about 48 weeks or about 52 weeks, or longer. In some embodiments, a recombinant oncolytic vaccinia virus as described herein can be administered using a prime-boost regimen.

In some examples, the subject can be put on a reduced carbohydrate diet, e.g., a ketogenic diet prior to, concurrent with, and following administration of the modified oncolytic vaccinia virus es or the pharmaceutical composition comprising the same, as described herein, according to any of the methods of treatment described herein. In certain embodiments, the subject can be put on a diet that can comprise consuming less than 500 grams of carbohydrates per day, less than 450 grams of carbohydrates per day, less than 450 grams of carbohydrates per day, less than 400 grams of carbohydrates per day, less than 350 grams of carbohydrates per day, less than 300 grams of carbohydrates per day, less than 250 grams of carbohydrates per day, less than 200 grams of carbohydrates per day, less than 150 grams of carbohydrates per day, less than 100 grams of carbohydrates per day, less than 90 grams of carbohydrates per day, less than 80 grams of carbohydrates per day, less than 70 grams of carbohydrates per day, less than 60 grams of carbohydrates per day, less than 50 grams of carbohydrates per day, less than 40 grams of carbohydrates per day, less than 30 grams of carbohydrates per day, less than 20 grams of carbohydrates per day, less or than 10 grams of carbohydrates per day.

An exemplary method for the delivery of a recombinant vaccinia virus of the present disclosure or a pharmaceutical composition comprising the same, to cancer or tumor cells can be via intratumoral injection. However, alternate methods of administration can also be used, e.g., intravenous, via infusion, parenteral, intravenous, intradermal, intramuscular, transdermal, rectal, intraurethral, intravaginal, intranasal, intrathecal, or intraperitoneal. The routes of administration can vary with the location and nature of the tumor. In certain embodiments, the route of administration can be intradental, transdermal, parenteral, intravenous, intramuscular, intranasal, subcutaneous, regional (e.g., in the proximity of a tumor, particularly with the vasculature or adjacent vasculature of a tumor), percutaneous, intrathecal, intratracheal, intraperitoneal, intraarterial, intravesical, intratumoral, inhalation, perfusion, by lavage or orally. An injectable dose of the recombinant vaccinia virus can be administered as a bolus injection or as a slow infusion. In certain embodiments, the modified oncolytic vaccinia virus can be administered to the patient from a source implanted in the patient. In certain embodiments, administration of the modified oncolytic vaccinia virus can occur by continuous infusion over a selected period of time. In some instances, a recombinant vaccinia virus as described herein, or a pharmaceutical composition comprising the same can be administered at a therapeutically effective dose by infusion over a period of about 15 mins, about 30 mins, about 45 mins, about 50 mins, about 55 mins, about 60 minutes, about 75 mins, about 90 mins, about 100 mins, or about 120 mins or longer. The recombinant vaccinia virus or the pharmaceutical composition of the present disclosure can be administered as a liquid dosage, wherein the total volume of administration is about 1 mL to about 5 mL, about 5 mL to 10 mL, about 15 mL to about 20 mL, about 25 mL to about 30 mL, about 30 mL to about 50 mL, about 50 mL to about 100 mL, about 100 mL to 150 mL, about 150 mL to about 200 mL, about 200 mL to about 250 mL, about 250 mL to about 300 mL, about 300 mL to about 350 mL, about 350 mL to about 400 mL, about 400 mL to about 450 mL, about 450 mL to 500 mL, about 500 mL to 750 mL, or about 750 mL to 1000 mL.

Method of Using Recombinant Oncolytic Virus

The recombinant oncolytic viruses described herein or a pharmaceutical composition or a vaccine comprising the same, as described above, can be used for cancer, in cancer immunotherapy and treatment of tumors. The tumors can be solid and liquid tumors including but not limited to melanoma, hepatocellular carcinoma, breast cancer, lung cancer, non-small cell lung cancer, peritoneal cancer, prostate cancer, bladder cancer, ovarian cancer, leukemia, lymphoma, renal cell carcinoma, pancreatic cancer, epithelial carcinoma, gastric/GE junction adenocarcinoma, cervical cancer, colon carcinoma, colorectal cancer, duodenal cancer, pancreatic adenocarcinoma, adenoid cystic, sarcoma, mesothelioma, glioblastoma multiforme, astrocytoma, multiple myeloma, prostate carcinoma, hepatocellular carcinoma, cholangiocarcinoma, pancreatic adenocarcinoma, head and neck squamous cell carcinoma, cervical squamous-cell carcinoma, osteosarcoma, epithelial ovarian carcinoma, acute lymphoblastic lymphoma or myeloproliferative neoplasms. As such, some embodiments of this disclosure provide a method of treatment of a cancer, a tumor, a cancer immunotherapy, by administering a recombinant oncolytic virus as described herein, or a pharmaceutical or immunogenic composition comprising the same.

The recombinant vaccinia virus described herein or a pharmaceutical composition or a vaccine comprising the same, as described above, can be used for treating cancer, in cancer immunotherapy and treatment of tumors. The tumors can be solid and liquid tumors including but not limited to melanoma, hepatocellular carcinoma, breast cancer, lung cancer, non-small cell lung cancer, peritoneal cancer, prostate cancer, bladder cancer, ovarian cancer, leukemia, lymphoma, renal cell carcinoma, pancreatic cancer, epithelial carcinoma, gastric/GE junction adenocarcinoma, cervical cancer, colon carcinoma, colorectal cancer, duodenal cancer, pancreatic adenocarcinoma, adenoid cystic, sarcoma, mesothelioma, glioblastoma multiforme, astrocytoma, multiple myeloma, prostate carcinoma, hepatocellular carcinoma, cholangiocarcinoma, pancreatic adenocarcinoma, head and neck squamous cell carcinoma, cervical squamous-cell carcinoma, osteosarcoma, epithelial ovarian carcinoma, acute lymphoblastic lymphoma or myeloproliferative neoplasms. As such, some embodiments of this disclosure provide a method of treatment of a cancer, a tumor, a cancer immunotherapy, by administering a recombinant vaccinia virus as described herein, or a pharmaceutical or immunogenic composition comprising the same.

Cancer cells that can be treated by the methods of this disclosure include cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In some cases, solid cancers that are metastatic can be treated using the recombinant oncolytic viruses of this disclosure, such as a recombinant oncolytic vaccinia virus that is advantageous for systemic delivery. In some cases, solid cancers that are inaccessible or difficult to access, such as for purpose of intratumoral delivery of therapeutic agents, can be treated using the recombinant oncolytic viruses of this disclosure, such as a recombinant oncolytic virus that is advantageous for systemic delivery. Cancers that are associated with increased expression of free fatty acids can, in some examples, can be treated using the recombinant oncolytic viruses of this disclosure, such as a recombinant oncolytic vaccinia virus that is advantageous for systemic delivery and forms increased amounts of EEV.

Combination Therapies

The methods of this disclosure comprise, in some aspects, administering a recombinant oncolytic virus as disclosed herein or a pharmaceutical or an immunogenic composition comprising the same, followed by, preceded by or in combination with one or more further therapy. Examples of the further therapy can include, but are not limited to, chemotherapy, radiation, oncolytic viral therapy with an additional virus, treatment with immunomodulatory proteins, an anti-cancer agent, or any combinations thereof. The further therapy can be administered concurrently or sequentially with respect to administration of the modified virus, such as oncolytic vaccinia virus. In certain embodiments, the methods of this disclosure can comprise administering a modified oncolytic virus as disclosed herein, followed by, preceded by, or in combination with one or more anti-cancer agents or cancer therapies. Anti-cancer agents can include, but are not limited to, chemotherapeutic agents, radiotherapeutic agents, cytokines, immune checkpoint inhibitors, anti-angiogenic agents, apoptosis-inducing agents, anti-cancer antibodies and/or anti-cyclin-dependent kinase agents. In certain embodiments, the cancer therapies can include chemotherapy, biological therapy, radiotherapy, immunotherapy, hormone therapy, anti-vascular therapy, cryotherapy, toxin therapy and/or surgery or combinations thereof. In certain embodiments, the methods of this disclosure can include administering a recombinant virus, disclosed herein, followed by, preceded by or in combination with a modified oncolytic virus of this disclosure.

In certain embodiments, treatment using a recombinant oncolytic virus can be used alone or in combination with one or immunomodulatory agents. An immunomodulatory agent can include any compound, molecule or substance capable of suppressing antiviral immunity associated with a tumor or cancer. In certain embodiments, the immunomodulatory agent can be capable of suppressing innate immunity or adaptive immunity to the modified virus. Non-limiting examples of immunomodulatory agents include anti-CD33 antibody or variable region thereof, an anti-CD11b antibody or variable region thereof, a COX2 inhibitor, e.g., celecoxib, cytokines, such as IL-12, GM-CSF, IL-2 (having an amino acid sequence as set forth in either SEQ ID NO: 33 or 34), IFN3 and IFN-g, and chemokines, such as MIP-1, MCP-1 and IL-8. In certain embodiments, the immunomodulatory agent can include immune checkpoint modulators such as, but not limited to, anti-CTLA4, anti-PD-1, and anti-PD-L1 and TLR agonists (e.g., Poly I:C). In some examples, the immunomodulatory agent can include an immune checkpoint inhibitor, such as an antagonist of PD-1 (e.g., an antagonist antibody that binds to PD-1), an antagonist of PD-L1 (e.g., an antagonist antibody that binds to PD-L1), an antagonist of CTLA-4 (e.g., an antagonist antibody that binds to CTLA-4), an antagonist of A2AR (e.g., an antagonist antibody that binds to A2AR), an antagonist of B7-H3 (e.g., an antagonist antibody that binds to B7-H3), an antagonist of B7-H4 (e.g., an antagonist antibody that binds to B7-H4), an antagonist of BTLA (e.g., an antagonist antibody that binds to BTLA), an antagonist of IDO (e.g., an antagonist antibody that binds to IDO), an antagonist of KIR (e.g., an antagonist antibody that binds to KIR), an antagonist of LAG3 (e.g., an antagonist antibody that binds to LAG3), an antagonist of TIM-3 (e.g., an antagonist antibody that binds to TIM3). In some embodiments, the further therapy can comprise administering an immune checkpoint regulator. In one example, the immune checkpoint regulator can be TGN1412. In one example, the immune checkpoint regulator can be NKTR-214. In one example, the immune checkpoint regulator can be MEDI0562. In one example, the immune checkpoint regulator can be MEDI6469. In one example, the immune checkpoint regulator can be MEDI6383. In one example, the immune checkpoint regulator can be JTX-2011. In one example, the immune checkpoint regulator can be pembrolizumab. In one example, the immune checkpoint regulator can be nivolumab. In one example, the immune checkpoint regulator can be ipilimumab. In one example, the immune checkpoint regulator can be tremelimumab. In one example, the immune checkpoint regulator can be atezolizumab. In one example, the immune checkpoint regulator can be MGA271. In one example, the immune checkpoint regulator can be indoximod. In one example, the immune checkpoint regulator can be epacadostat. In one example, the immune checkpoint regulator can be lirilumab. In one example, the immune checkpoint regulator can be BMS-986016. In one example, the immune checkpoint regulator can be MPDL3280A. In one example, the immune checkpoint regulator can be avelumab. In one example, the immune checkpoint regulator can be durvalumab. In one example, the immune checkpoint regulator can be MEDI4736. In one example, the immune checkpoint regulator can be MEDI4737. In one example, the immune checkpoint regulator can be TRX518. In one example, the immune checkpoint regulator can be MK-4166. In one example, the immune checkpoint regulator can be urelumab (BMS-663513). In one example, the immune checkpoint regulator can be PF-05082566 (PF-2566).

In certain examples, where the further therapy is radiation exemplary doses can be 5,000 Rads (50 Gy) to 100,000 Rads (1000 Gy), or 50,000 Rads (500 Gy), or other appropriate doses within the recited ranges. Alternatively, the radiation dose can be about 30 to 60 Gy, about 40 to about 50 Gy, about 40 to 48 Gy, or about 44 Gy, or other appropriate doses within the recited ranges, with the dose determined, example, by means of a dosimetry study as described above. "Gy" as used herein can refer to a unit for a specific absorbed dose of radiation equal to 100 Rads. Gy is the abbreviation for "Gray."

In certain examples, where the further therapy is chemotherapy, exemplary chemotherapeutic agents can include without limitation alkylating agents (e.g., nitrogen mustard derivatives, ethylenimines, alkylsulfonates, hydrazines and triazines, nitrosureas, and metal salts), plant alkaloids (e.g., vinca alkaloids, taxanes, podophyllotoxins, and camptothecan analogs), antitumor antibiotics (e.g., anthracyclines, chromomycins, and the like), antimetabolites (e.g., folic acid antagonists, pyrimidine antagonists, purine antagonists, and adenosine deaminase inhibitors), topoisomerase I inhibitors, topoisomerase II inhibitors, and miscellaneous antineoplastics (e.g., ribonucleotide reductase inhibitors, adrenocortical steroid inhibitors, enzymes, antimicrotubule agents, and retinoids). Exemplary chemotherapeutic agents can include, without limitation, anastrozole, bicalutamide, bleomycin sulfate, busulfan, busulfan injection, capecitabine, N4-pentoxycarbonyl-5-deoxy-5-fluorocytidine, carboplatin, carmustine, chlorambucil, cisplatin, cladribine, cyclophosphamide, cytarabine, cytosine arabinoside, cytarabine liposome injection, dacarbazine, dactinomycin, daunorubicin hydrochloride, daunorubicin citrate liposome injection, dexamethasone, docetaxel, doxorubicin hydrochloride, etoposide, fludarabine phosphate, 5-fluorouracil, flutamide, tezacitibine, gemcitabine (difluorodeoxycitidine), hydroxyurea, Idarubicin, ifosfamide, irinotecan, L-asparaginase, leucovorin calcium, melphalan, 6-mercaptopurine, methotrexate, mitoxantrone, mylotarg, paclitaxel, phoenix, pentostatin, polifeprosan 20 with carmustine implant, tamoxifen citrate, teniposide, 6-thioguanine, thiotepa, tirapazamine, topotecan hydrochloride for injection, vinblastine, vincristine, and vinorelbine, ibrutinib, idelalisib, and brentuximab vedotin.

Exemplary alkylating agents can include, without limitation, nitrogen mustards, ethylenimine derivatives, alkyl sulfonates, nitrosoureas and triazenes such as: uracil mustard chlormethine, cyclophosphamide, ifosfamide, melphalan, Chlorambucil, pipobroman, triethylenemelamine, triethylenethiophosphoramine, Temozolomide, thiotepa, busulfan, and dacarbazine. Additional exemplary alkylating agents include, without limitation, oxaliplatin, temozolomide, dactinomycin, L-PAM, L-sarcolysin, hexamethylmelamine, carmustine, bendamustine, busulfan; carboplatin, lomustine, cisplatin, chlorambucil, cyclophosphamide, dacarbazine, altretamine, ifosfamide, prednumustine, procarbazine, mechlorethamine, streptozocin, thiotepa, cyclophosphamide; and bendamustine HCl.

Exemplary anthracyclines can include, without limitation, e.g., doxorubicin, bleomycin, daunorubicin, daunomycin, rubidomycin hydrochloride, mitoxantrone, epirubicin, idarubicin, mitomycin C, geldanamycin, herbimycin, ravidomycin, and desacetylravidomycin.

Exemplary vinca alkaloids can include, but are not limited to, vinorelbine tartrate, vincristin, vindesine, vinblastine; and vinorelbine.

Exemplary proteasome inhibitors can, but are not limited to, bortezomib; carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoac-etamido)-4-phenylbutanamido)-pentanamide), marizomib (NPI-0052), ixazomib citrate, delanzomib, and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide.

"In combination with," as used herein, can mean that the recombinant virus, such as an oncolytic vaccinia virus as described herein or a pharmaceutical composition comprising the same, and the further therapy, such as a further therapy comprising one or more agents are administered to a subject as part of a treatment regimen or plan. In certain embodiments, being used in combination may not require that the recombinant virus and the one or more agents are physically combined prior to administration or that they be administered over the same time frame. For example, and not by way of limitation, the recombinant virus and the one or more agents can be administered concurrently to the subject being treated or can be administered at the same time or sequentially in any order or at different points in time.

The further therapy can be administered, in various embodiments, in a liquid dosage form, a solid dosage form, a suppository, an inhalable dosage form, an intranasal dosage form, in a liposomal formulation, a dosage form comprising nanoparticles, a dosage form comprising microparticles, a polymeric dosage form, or any combinations thereof. In certain embodiments, the further therapy is administered over a period of about 1 week to about 2 weeks, about 2 weeks to about 3 weeks, about 3 weeks to about 4 weeks, about 4 weeks to about 5 weeks, about 6 weeks to about 7 weeks, about 7 weeks to about 8 weeks, about 8 weeks to about 9 weeks, about 9 weeks to about 10 weeks, about 10 weeks to about 11 weeks, about 11 weeks to about 12 weeks, about 12 weeks to about 24 weeks, about 24 weeks to about 48 weeks, about 48 weeks or about 52 weeks, or longer. The frequency of administration of the further therapy can be, in certain instances, once daily, twice daily, once every week, once every three weeks, once every four weeks (or once a month), once every 8 weeks (or once every 2 months), once every 12 weeks (or once every 3 months), or once every 24 weeks (once every 6 months). In certain embodiments, a method of treating a subject having a cancer can include administering, to the subject, an effective amount of a recombinant virus, e.g., a recombinant vaccinia virus, of this disclosure. In certain embodiments, the methods of this disclosure can further include administering to the subject an effective amount of one or more agents. For example, and not by way of limitation, the agent can be an anti-cancer agent, an immunomodulatory agent, or any combinations thereof, as described above. An "anti-cancer agent," as used herein, can be any molecule, compound, chemical or composition that has an anti-cancer effect. Anti-cancer agents include, but are not limited to, chemotherapeutic agents, radiotherapeutic agents, cytokines, immune checkpoint inhibitors, anti-angiogenic agents, apoptosis-inducing agents, anti-cancer antibodies and/or anti-cyclin-dependent kinase agents.

Additional Embodiments

Provided herein are recombinant oncolytic viruses comprising a modification in the viral genome wherein said modification comprises at least one of: a deletion or functional deletion of an endogenous nucleic acid encoding an MHC class II inhibitor; an insertion of an exogenous nucleic acid that results in activation or enhanced activation of MHC class II presentation; and an insertion of an exogenous nucleic acid encoding an MHC class I inhibitor that acts wholly or primarily within the infected cell. Further provided herein are recombinant oncolytic viruses comprising the deletion or functional deletion of an endogenous nucleic acid encoding the MHC class II inhibitor, wherein the deletion or functional deletion results in an increase of MHC class II presentation, and wherein the oncolytic virus is a vaccinia virus. Further provided herein are recombinant oncolytic viruses comprising the deletion or functional deletion of the endogenous nucleic acid encoding the MHC class II inhibitor, wherein the deletion or functional deletion of the endogenous nucleic acid encoding the MHC class II inhibitor comprises a deletion of a gene encoding protein A35 of a vaccinia virus. Further provided herein are recombinant oncolytic viruses wherein the deletion or functional deletion of the gene encoding a vaccinia virus protein A35 is a deletion or functional deletion of gene WR158. Further provided herein are recombinant oncolytic viruses wherein the modification comprises the insertion of an exogenous nucleic acid that results in activation or enhanced activation of the MHC class II presentation, and wherein the exogenous nucleic acid encodes for: an apoptosis inhibitor protein or a necrotic cell death activator protein; an autophagy enhancer protein; an asparaginyl endopeptidase; a class II transactivator; an interferon-gamma; a Toll-like receptor activator; or a dendritic cell maturation activator. Further provided herein are recombinant oncolytic viruses comprising the autophagy enhancer protein, wherein the autophagy enhancer protein is HMGB1 or a functional domain or a variant thereof. Further provided herein are recombinant oncolytic viruses comprising the dendritic cell maturation activator, wherein the dendritic cell maturation activator comprises osteopontin, or TNF-alpha, or functional fragments or variants thereof. Further provided herein are recombinant oncolytic viruses wherein the encoded MHC II upregulating protein is fused to a secretion sequence a cell permeabilizing domain or a combination thereof, to achieve MHC II upregulation throughout the tumor. Further provided herein are recombinant oncolytic viruses wherein the modification comprises the insertion of the exogenous nucleic acid encoding the MHC class I inhibitor, and wherein the insertion results in an inhibition or partial inhibition of MHC class I presentation. Further provided herein are recombinant oncolytic viruses wherein the insertion of the exogenous nucleic acid encoding the MHC class I inhibitor comprises insertion of a gene encoding one or more cowpox virus proteins. Further provided herein are recombinant oncolytic viruses wherein the insertion of an exogenous nucleic acid encoding the MHC class I inhibitor comprises insertion of a gene encoding cowpox protein CPXV012 or a functional fragment or a variant thereof. Further provided herein are recombinant oncolytic viruses wherein the insertion of an exogenous nucleic acid encoding the MHC class I inhibitor comprises insertion of a gene encoding cowpox protein CPXV203 or a functional fragment or a variant thereof. Further provided herein are recombinant oncolytic viruses wherein the insertion of an exogenous nucleic acid encoding the MHC class I inhibitor comprises insertion of a gene encoding at least one of: Epstein-Barr virus encoded nuclear antigen 1 protein; Herpes simplex virus encoded ICP47 protein; Herpes simplex virus encoded UL49.5 protein; Cytomegalovirus encoded US6, US2, US3, US11, or gp48 protein; Epstein-Barr Virus encoded BNLF2a protein; Adenovirus encoded E3-19K protein; Human Immunodeficiency Virus or Simian Immunodeficiency Virus encoded Nef protein; Kaposi's sarcoma-associated herpesvirus encoded kK3, vIRF3 or kK5 protein; or a dominant negative form of IRF7 or IRF3. Further provided herein are recombinant oncolytic viruses wherein the MHC class I inhibitor comprises a TAP inhibitor. Further provided herein are recombinant oncolytic viruses wherein the TAP inhibitor acts wholly or primarily within infected cells. Further provided herein are recombinant oncolytic viruses wherein the modification in the viral genome reduces an immune response targeting a virus-infected tumor cell and increases an immune response targeting cells surrounding the virus-infected tumor cell. Further provided herein are recombinant oncolytic viruses wherein a thymidine kinase gene is deleted from the viral genome. Further provided herein are recombinant oncolytic viruses further comprising an exogenous nucleic acid encoding a hyaluronidase. Further provided herein are recombinant oncolytic viruses wherein the hyaluronidase is PH-20 or HysA. Further provided herein are recombinant oncolytic viruses wherein the oncolytic virus is a vaccinia virus, and the vaccinia virus is a Western Reserve strain Vaccinia virus (ATCC VR-1354), a Copenhagen strain, an IHD strain, a Wyeth strain (ATCC VR-325), a NYCBOH strain, a Tian Tan strain, a Lister strain, an Ankara strain (ATCC VR-1508 or ATTC VR1566), a USSR strain, or an ACAM2000 strain.

Provided herein are recombinant oncolytic viruses comprising a modification in the viral genome wherein the modification comprises a deletion or functional deletion of a vaccinia virus gene encoding A35 protein and insertion of an exogenous gene encoding cowpox protein CPXV012 or cowpox protein CPXV203. Further provided herein are recombinant oncolytic viruses wherein the modification is such that insertion of the exogenous gene encoding cowpox protein CPXV012 is at the locus of the gene encoding A35 protein of a vaccinia virus. Further provided herein are recombinant oncolytic viruses wherein the modification is such that insertion of the exogenous gene encoding cowpox protein CPXV203 is at the locus of the gene encoding A35 protein of a vaccinia virus. Further provided herein are recombinant oncolytic viruses further comprising an additional modification in the viral genome. Further provided herein are recombinant oncolytic viruses wherein the additional modification comprises at least one of: an insertion of an exogenous nucleic acid that codes for a chemokine receptor or a functional domain or a variant thereof; or an insertion of an exogenous nucleic acid that codes for cytokine or a functional domain or a variant thereof. Further provided herein are recombinant oncolytic viruses comprising the exogenous nucleic acid that codes for a cytokine or a functional domain or a variant thereof, wherein the cytokine comprises at least one of: interleukin-2 (IL-2), interleukin-15/interleukin-15Ra (IL15/IL15Ra), interleukin-7 (IL-7), or a functional domain or a variant thereof. Further provided herein are recombinant oncolytic viruses wherein the additional modification comprises an insertion of an exogenous nucleic acid that codes for a fusion protein comprising a cytokine and a metabolic modulator protein. Further provided herein are recombinant oncolytic viruses comprising the exogenous nucleic acid that codes for the chemokine receptor or a functional domain or a variant thereof, wherein the chemokine receptor comprises at least one of: CXCR4, CCR2, or functional domains or variants thereof. Further provided herein are recombinant oncolytic viruses wherein the chemokine receptor comprises the CXCR4 or a functional domain or a variant thereof. Further provided herein are recombinant oncolytic viruses wherein the chemokine receptor comprises the CCR2 or a functional domain or a variant thereof, wherein the CCR2 comprises a wild-type CCR2 or a mutated CCR2. Further provided herein are recombinant oncolytic viruses wherein the exogenous nucleic acid that codes for the chemokine receptor or a functional domain or a variant thereof comprises a codon optimized sequence. Further provided herein are recombinant oncolytic viruses wherein the exogenous nucleic acid that codes for the chemokine receptor or a functional domain or a variant thereof comprises a non-codon optimized sequence. Further provided herein are recombinant oncolytic viruses wherein the additional modification comprises mutation or a complete or a partial deletion of a viral gene comprising at least one of: A52R, B15R, K7R, A46R, N1L, E3L, K1L, M2L, C16, N2R, B8R, B18R, VH1 of a vaccinia virus or a functional domain or fragment or variant thereof, or any combinations thereof. Further provided herein are recombinant oncolytic viruses wherein a thymidine kinase gene is deleted from the viral genome. Further provided herein are recombinant oncolytic viruses further comprising an exogenous nucleic acid encoding a hyaluronidase. Further provided herein are recombinant oncolytic viruses wherein the hyaluronidase is PH-20 or HysA. Further provided herein are recombinant oncolytic viruses wherein the oncolytic virus is a vaccinia virus, and the vaccinia virus is a Western Reserve strain Vaccinia virus (ATCC VR-1354), a Copenhagen strain, an IHD strain, a Wyeth strain (ATCC VR-325), a NYCBOH strain, a Tian Tan strain, a Lister strain, an Ankara strain (ATCC VR-1508 or ATTC VR1566), a USSR strain, or an ACAM2000 strain.

Provided herein are immunogenic compositions comprising a recombinant oncolytic virus according to any embodiments as described herein.

Provided herein are pharmaceutical compositions comprising a recombinant oncolytic virus or an immunogenic composition according to any embodiments as described herein and at least one of: a solubilizing agent, an excipient, or a pharmaceutically acceptable carrier. Further provided herein are pharmaceutical compositions, wherein the excipient comprises one or more of a buffering agent, a stabilizer, an antioxidant, a binder, a diluent, a dispersing agent, a rate controlling agent, a lubricant, a glidant, a disintegrant, a plasticizer, a preservative, or any combinations thereof. Further provided herein are pharmaceutical compositions, wherein the excipient comprises di-sodium hydrogen phosphate dihydrate, sodium dihydrogen phosphate dihydrate, sodium chloride, myo-inositol, sorbitol, or any combinations thereof. Further provided herein are pharmaceutical compositions, wherein the pharmaceutical composition does not comprise a preservative. Further provided herein are pharmaceutical compositions, further comprising one or more of a preservative, a diluent, and a carrier. Further provided herein are pharmaceutical compositions, further comprising an additional active ingredient or a salt thereof. Further provided herein are pharmaceutical compositions, wherein the solubilizing agent is sterile water. Further provided herein are pharmaceutical compositions, further comprising an additional active ingredient, wherein the additional active ingredient is an anti-cancer agent or a further oncolytic virus.

Provided herein are methods of reducing growth of a cancer cell, exemplary methods comprising administering to the cancer cell an effective amount of the recombinant oncolytic virus, the immunogenic composition, or the pharmaceutical composition according to any embodiments as described herein.

Provided herein are methods of regressing the growth of a tumor, exemplary methods comprising administering to the tumor an effective amount of the recombinant oncolytic virus, the immunogenic composition, or the pharmaceutical composition according to any embodiments as described herein. Further provided herein are methods, wherein the tumor is in a subject and the administering comprises administering to the subject. Further provided herein are methods comprising administering a further therapy, wherein the further therapy comprises chemotherapy, radiation, oncolytic viral therapy with an additional virus, treatment with immunomodulatory proteins, a CAR T cellular therapy, an anti-cancer agent, or any combinations thereof. Further provided herein are methods, wherein the further therapy comprises administering an immunomodulatory agent comprising anti-CD33 antibody and variable region thereof, an anti-CD11b antibody and variable region thereof, a COX2 inhibitor, a cytokine, a chemokine, an anti-CTLA4 antibody or an antigen binding fragment thereof, an anti-PD-1 antibody or an antigen binding fragment thereof, an anti-PD-L1 antibody or an antigen binding fragment thereof, or a TLR agonist.

A method of treatment comprising administering to a subject in need thereof an effective amount of a recombinant oncolytic virus, the immunogenic composition, or a pharmaceutical composition according to any embodiments described herein. Further provided herein are methods, wherein the administering comprises an intratumoral administration. Further provided herein are methods, wherein the administering comprises a systemic administration. Further provided herein are methods, wherein the systemic administration comprises at least one of: an intraperitoneal administration, an oral administration, an intravenous administration, an intranasal administration, a sublingual administration, a rectal administration, a transdermal administration, or any combination thereof. Further provided herein are methods, wherein the subject has a cancer, and wherein the cancer is at least one of: a melanoma, a hepatocellular carcinoma, a breast cancer, a lung cancer, a non-small lung cancer, a peritoneal cancer, a prostate cancer, a bladder cancer, an ovarian cancer, a leukemia, a lymphoma, a renal cell carcinoma, a pancreatic cancer, an epithelial carcinoma, a gastric/GE junction adenocarcinoma, a cervical cancer, a colon carcinoma, a colorectal cancer, a duodenal cancer, a pancreatic adenocarcinoma, an adenoid cystic, a sarcoma, a mesothelioma, a glioblastoma multiforme, an astrocytoma, a multiple myeloma, a prostate carcinoma, a hepatocellular carcinoma, a cholangiocarcinoma, a head and neck squamous cell carcinoma, a cervical squamous-cell carcinoma, an osteosarcoma, an epithelial ovarian carcinoma, an acute lymphoblastic lymphoma, a myeloproliferative neoplasm, or any combination thereof. Further provided herein are methods, wherein the recombinant oncolytic virus, the immunogenic composition, or the pharmaceutical composition is administered at a dosage that comprises from about $10^6$ PFU/mL to about $10^{10}$ PFU/mL of the recombinant vaccinia virus. Further provided herein are methods, wherein the recombinant oncolytic virus, or the pharmaceutical composition is administered at a dosage that comprises about $3 \times 10^9$ PFU/mL of the recombinant vaccinia virus. Further provided herein are methods, wherein the recombinant oncolytic virus, the immunogenic composition, or the pharmaceutical composition is administered, independently, in an initial dose for a first period of time, an intermediate dose for a second period of time, and a high dose for a third period of time. Further provided herein are methods, comprising administration of the initial, the intermediate, and the high dose, independently, wherein the initial dose is lower than the intermediate dose and the intermediate dose is lower than the high dose. Further provided herein are methods, wherein the recombinant oncolytic virus, the immunogenic composition, or the pharmaceutical composition is administered, independently, in a high dose for a first period of time, an intermediate dose for a second period of time, and a low dose for a third period of time. Further provided herein are methods, comprising administration of the initial, the intermediate, and the low dose, independently, wherein the initial dose is higher than the intermediate dose and the intermediate dose is higher than the low dose. Further provided herein are methods, wherein the first, second, and third periods of time are each from about 1 day, about 2 days, about 3 days, about 4 days, about 5 days, about 6 days, about 1 week, about 2 week, about 3 weeks, about 4 weeks, about 6 weeks, about 7 weeks, about 8 weeks, about 9 weeks, about 10, weeks, about 12 weeks, about 4 months, about 5 months, about 6 months, about 7 months, about 8 months, about 9 months, about 10 months, about 11 months or about 1 year. Further provided herein are methods, wherein the recombinant oncolytic virus, the immunogenic composition, or the pharmaceutical composition independently comprises a liquid dosage form that is administered at a volume of about 1 mL to about 5 mL, about 5 mL to 10 mL, about 15 mL to about 20 mL, about 25 mL to about 30 mL, about 30 mL to about 50 mL, about 50 mL to about 100 mL, about 100 mL to 150 mL, about 150 mL to about 200 mL, about 200 mL to about 250 mL, about 250 mL to about 300 mL, about 300 mL to about 350 mL, about 350 mL to about 400 mL, about 400 mL to about 450 mL, about 450 mL to 500 mL, about 500 mL to 750 mL, or about 750 mL to 1000 mL. Further provided herein are methods, wherein the recombinant oncolytic virus, the immunogenic composition, or the pharmaceutical composition is administered in a liquid dosage form, a solid dosage form, an inhalable dosage form, an intranasal dosage form, a liposomal formulation, a dosage form comprising nanoparticles, a dosage form comprising microparticles, a polymeric dosage form, or any combination thereof. Further provided herein are methods, wherein the recombinant oncolytic virus, the immunogenic composition, or the pharmaceutical composition is administered for a duration of about 1 day, about 2 days, about 3 days, about 4 days, about 5 days, about 6 days, about 1 week, about 2 week, about 3 weeks, about 4 weeks, about 6 weeks, about 7 weeks, about 8 weeks, about 9 weeks, about 10, weeks, about 12 weeks, about 4 months, about 5 months, about 6 months, about 7 months, about 8 months, about 9 months, about 10 months, about 11 months, or about 1 year. Further provided herein are methods, wherein the recombinant oncolytic virus, the immunogenic composition, or the pharmaceutical composition is administered once daily, twice daily, once every week, once every two weeks, or once every three weeks. Further provided herein are methods, wherein the recombinant oncolytic virus, the immunogenic composition, or the pharmaceutical composition is administered as a bolus injection or a slow infusion. Further provided herein are methods, wherein the administration of the recombinant oncolytic virus, the immunogenic composition, or the pharmaceutical composition results in a first peak viral load after about 1 hour to about 3 days and a second peak viral load after about 3 days to about 10 days from administration of a first dose. Further provided herein are methods, comprising administration of a further therapy, wherein the further therapy is administered for a duration of about 1 day, about 2 days, about 3 days, about 4 days, about 5 days, about 6 days, about 1 week, about 2 week, about 3 weeks, about 4 weeks, about 6 weeks, about 7 weeks, about 8 weeks, about 9 weeks, about 10, weeks, or about 12 weeks. Further provided herein are methods, wherein the further therapy is administered once daily, twice daily, once every 1 day, once every 2 days, once every 3 days, once every 4 days, once every 5 days, once every 6 days, once every 1 week, once every 2 week, once every 3 weeks, once every 4 weeks, once every 6 weeks, once every 7 weeks, once every 8 weeks, once every 9 weeks, once every 10, weeks, once every 12 weeks, once every 4 months, once every 5 months, once every 6 months, once every 7 months, once every 8 months, once every 9 months, once every 10 months, once every 11 months, or once every 1 year. Further provided herein are methods, wherein the further therapy is administered in a liquid dosage form, a solid dosage form, an inhalable dosage form, an intranasal dosage form, a liposomal formulation, a dosage form comprising nanoparticles, a dosage form comprising microparticles, a polymeric dosage form, or any combination thereof. Further provided herein are methods, wherein the further therapy is administered in a liquid dosage form, a solid dosage form, an inhalable dosage form, an intranasal dosage form, a liposomal formulation, a dosage form comprising nanoparticles, a dosage form comprising microparticles, a polymeric dosage form, or any combinations thereof. Further provided herein are methods, wherein the further therapy is administered orally, intravenously, by an intratumoral injection, by intraperitoneal injection, or by radiation. Further provided herein are methods, wherein the further therapy comprises chemotherapy, radiation, oncolytic viral therapy with an additional virus, treatment with immunomodulatory proteins, a CAR T cellular therapy, an anti-cancer agent, or any combinations thereof. Further provided herein are methods, wherein the further therapy comprises administration of an immunomodulatory agent comprising anti-CD33 antibody and variable region thereof, an anti-CD11b antibody and variable region thereof, a COX2 inhibitor, a cytokine, a chemokine, an anti-CTLA4 antibody or an antigen binding fragment thereof, an anti-PD-1 antibody or an antigen binding fragment thereof, an anti-PD-L1 antibody or an antigen binding fragment thereof, or a TLR agonist. Further provided herein are methods, wherein the further therapy comprises administration of the anti-cancer agent, wherein the anti-cancer agent is a chemotherapeutic agent. Further provided herein are methods, wherein the subject is human.

EXAMPLES

The examples below further illustrate the described embodiments without limiting the scope of this disclosure.

Example 1: Tumor Model

Recombinant vaccinia virus was assayed in comparison to the same strain of virus without the modification as described herein in a tumor model system. The below table lists the viruses for testing and the modifications in the viral genome for the same:

TABLE 1

| MODEL | Unique Identifier UID | DESCRIPTION |
|---|---|---|
| B16 Tumor Model | WO0416N | A52R- mut CXCR4 TK- |
| | WO0434N | A52R- mut CXCR4 TK- 158- cpx012+ |
| | HCCTKM | WR.TK- |
| | VFB | Vehicle Formulated Buffer |

Table 1 above shows that the viruses used in the study were recombinant vaccinia virus WO0434N (shown as A52R- mutCXCR4 TK- 158- cpx012+) and reference vaccinia virus WO0416N (A52R- mutCXCR4 TK-). The modification to WO0434N was by deletion of TK gene and substitution of A52 gene with P7.5-driven mutant CXCR4 and substitution of A35 gene (WR158) with cowpox virus gene CPXV012. The reference vaccinia virus WO0416N had a deletion of TK gene and substitution of A52 gene with P7.5-driven mutant CXCR4. The controls were vaccinia virus Western Reserve Thymidine Kinase negative (WR.TK-) strain (HCCTKM) and vehicle formulated buffer (VFB). The nucleic acid sequence of the P7.5 promoter is defined by SEQ ID NO: 1. The nucleic acid sequence of the mutant CXCR4 gene is defined by SEQ ID NO: 15. The nucleic acid sequence of the CPXV012 is defined by SEQ ID NO: 2. The study was performed in B16 tumor model. The tumor volumes were measured 17 days after the virus administration for each group and controls. The results as shown in FIG. 1 indicate an enhancement in the therapeutic activity with WO0434N virus as compared to reference virus WO0416N or the controls HCCTKM and VFB.

Example 2: Strain Characterization

To assess whether a given virus is replication-competent or replication-defective in a cell type, replication capacity is assessed of a recombinant vaccinia virus is assessed via PCR assay using sera from a mammal or a rodent infected with the recombinant virus, a viral plaque assay, or any combinations thereof. For viral plaque assays, confluent monolayers of susceptible cells in tissue culture flasks are infected with vaccinia virus. After incubation, cytopathic effects (CPE) are observed and visualized through formation of a halo or circular clearing the cell monolayer. Cell culture media is replaced with a solution that increases the viscosity. The replaced solution includes gelatin or carboxymethylcellulose. The viral plaque assays are visualized by staining with an agent that increases cell contrast by eye or by microscopy. Incubation following infection can be for 4 to 48 hours before plaque can be observed. The staining agent is Crystal Violet. For PCR based assays, vaccinia virus content is quantified using qPCR-based approaches.

Example 3: Tumor Growth Inhibition

Animal assays were performed in mouse models of cancer to assess tumor growth impact of compositions described herein. Briefly, modified vaccinia viruses were intratumorally injected (IT) to Renca and EMT6 tumor bearing mice.

Modified vaccinia viruses were assessed in comparison to a Vehicle Formulated Buffer (VFB). Group 1 was treated with a modified vaccinia virus comprising a TK gene deletion, insertion of nucleic acid encoding the cowpox virus V012 protein (CPXV012) (SEQ ID NO: 2), a P7.5 promoter (SEQ ID NO: 1) and a loxP sequence (SEQ ID NO: 35). Group 2 was treated with a modified vaccinia virus comprising a WR158 gene deletion, insertion of nucleic acid encoding CPXV012 protein (SEQ ID NO: 2), a P7.5 promoter (SEQ ID NO: 1), and a loxP sequence (SEQ ID NO: 35). Group 3 was treated with a vaccinia virus comprising a TK gene deletion and insertion of nucleic acid encoding dominant negative interferon regulatory factor 7 (dnIRF7, SEQ ID NO: 36). Group 4 was treated with a modified vaccinia virus comprising a TK gene deletion and insertion of nucleic acid encoding viral interferon regulator factor 3 (vIRF3, SEQ ID NO: 38).

Balb/c mice were implanted subcutaneously with RENCA cell or EMT6 cell tumors. Mice were divided into groups of 10. Tumors were injected with a single dose of $1\times10^7$ pfu modified vaccinia virus or vehicle control.

Figure 2A:
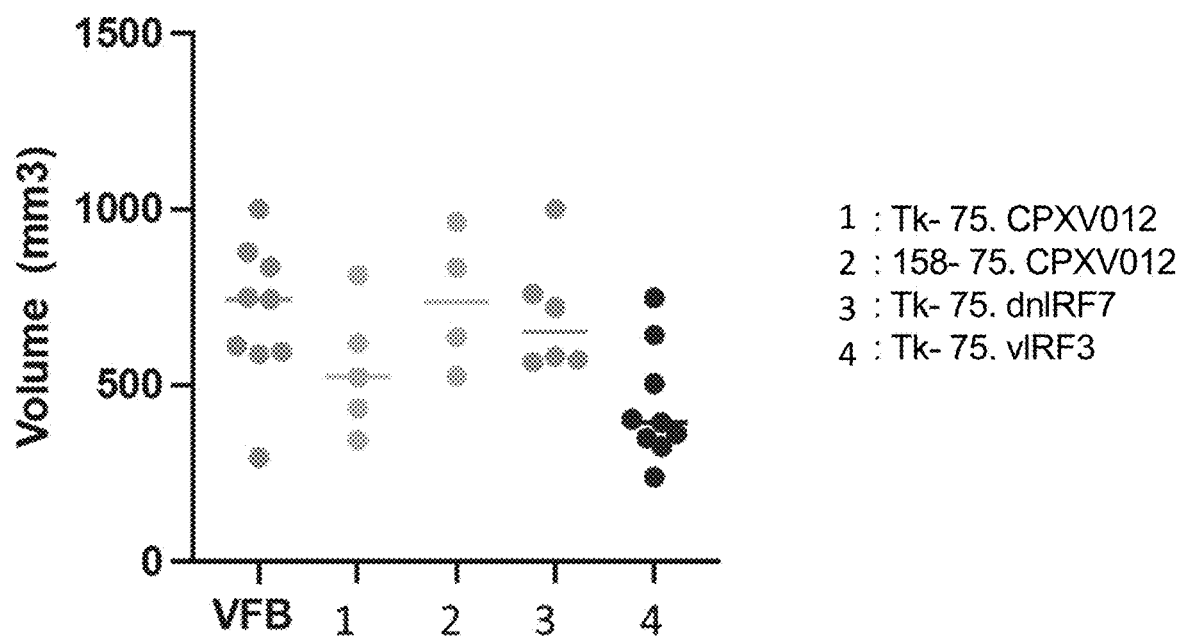
FIGS. 2A and 2B depict the change in Renca (FIG. 2A) or EMT6 (FIG. 2B) tumor volume, shown in cubic millimeters on the y-axis, following treatment with vehicle formulated buffer (VFB), or recombinant vaccinia virus comprising: (1) a TK gene deletion and insertion of nucleic acid encoding the cowpox virus V012 protein; (2) a WR158 gene deletion and insertion of nucleic acid encoding the cowpox virus V012 protein; (3) a TK gene deletion and insertion of nucleic acid encoding dominant negative interferon regulatory factor 7 (dnIRF7); or (4) a TK gene deletion and insertion of nucleic acid encoding viral interferon regulator factor 3 (vIRF3).

Tumor volumes in mice with Renca tumors were measured after 23 days, as shown in FIG. 2A. Groups treated with virus expressing cowpox virus V012 and vIRF3 showed the most effective reduction in Renca tumor volume.

Figure 2B:
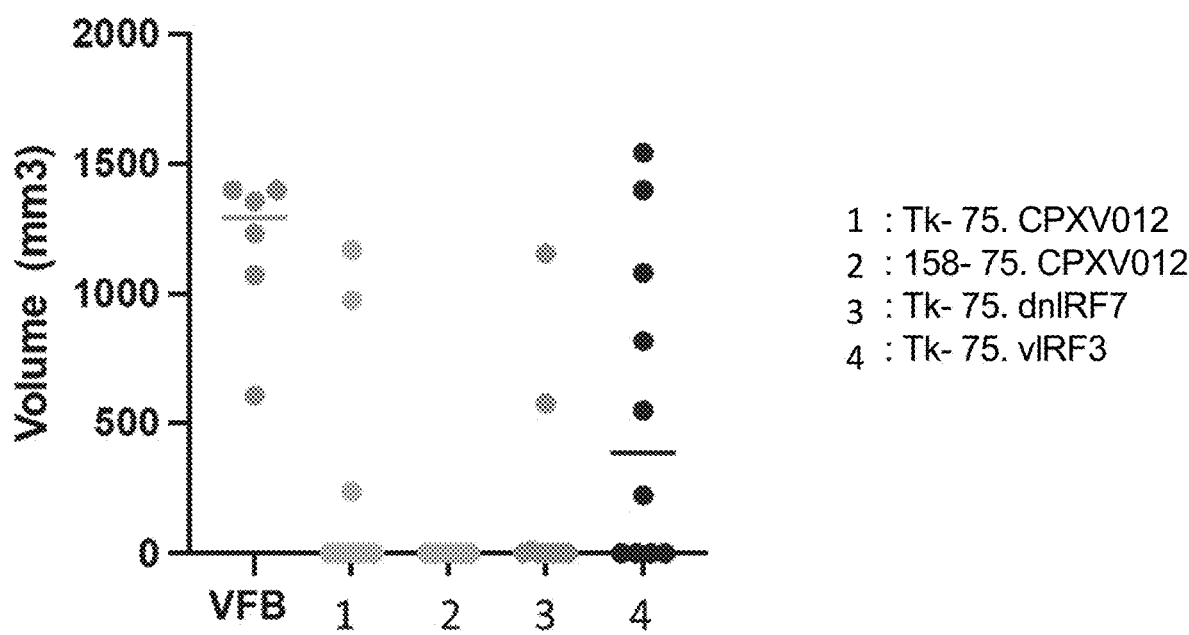

Tumor volumes in mice with EMT6 tumors were measured after 27 days, as shown in FIG. 2B. Groups treated with virus expressing cowpox virus V012 and dnIRF7 showed the most effective reduction in EMT6 tumor volume.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

TABLE 2

Sequences

| SEQ ID NO: | PROTEIN/ NUCLEIC ACID NAME | SEQUENCES |
|---|---|---|
| 1 | P7.5 promoter (DNA) | TCACTAATTCCAAACCCACCCGCTTTTTATAGTAAGTTTTTCACC CATAAATAATAAATACAATAATTAATTTCTCGTAAAAGTAGAAAA TATATTCTAATTTATTGCACGGTAAGGAAGTAGATCATAA |
| 2 | CPXV012 (DNA) | ATGTTCATCATGCGCGAGAGCATTTACCGCGTGATGATTGTCATT TTGTATTTGAGCTTGATTTCTTCGTTTTTGGTTATCTGCTCTATG GAGCACGGCTACTTCCAGGAGGGCATCAGCCGCTTCAAGATTTGT CCCTATCATTGGTATAAACAACACATGAGTTTATTGTTTCGTCGT TACTATCACAAGCTGGATAGTATCATCTAG |
| 3 | CPXV012 (polypeptide) | MFIMRESIYRVMIVILYLSLISSFLVICSMEHGYFQEGISRFKIC PYHWYKQHMSLLFRRYYHKLDSII |
| 4 | HMGB1 (human, mutant, DNA) | GGCAAAGGAGATCCTAAGAAGCCGAGAGGCAAAATGTCATCATAT GCATTCTTCGTGCAAACTTGTCGGGAGGAGCATAAGAAGAAGCAC CCAGATGCTGCAGTCAACTTCGCTGAGTTTGCAAAGAAGTGCGCT |

TABLE 2-continued

Sequences

| SEQ ID NO: | PROTEIN/ NUCLEIC ACID NAME | SEQUENCES |
|---|---|---|
|  |  | GAGAGGTGGAAGACCATGGCAGCTAAAGAGAAAGGAAAATTTGAA GATATGGCAAAAGCGGACAAGGCCCGTTATGAAAGAGAAATGAAA ACCTATATCCCTCCCAAAGGGGAGACAAAAAAGAAGTTCAAGGAC CCCAATGCACCCAAGAGGCCTCCTTCGGCCTTCTTCCTCTTCTGC TCTGAGTATCGCCCAAAAATCAAAGGAGAACATCCTGGCCTGTCC ATTGGTGATGTTGCGAAGAAACTGGGAGAGATGTGGAATAACACT GCTGCAGATGACAAGCAGCCTTATGAAAAGAAGGCTGCCAAGCTG AAGGAAAAATATGAAAGGATATTGCTGCATATCGAGCTAAAGGA AAGCCTGATGCAGCAAAAAAGGGAGTTGTCAAGGCTGAAAAAGCG AAGAAAAAGAAGGAAGAGGAGGAAGATGAGGAAGATGAAGAGGAT GAGGAGGAGGAGGAAGATGAAGAAGATGAAGATGAAGAAGAAGAT GATGATGATGAATAA |
| 5 | HMGB1 (human, mutant, protein) | GKGDPKKPRGKMSSYAFFVQTCREEHKKKHPDAAVNFAEFAKKCA ERWKTMAAKEKGKFEDMAKADKARYEREMKTYIPPKGETKKKFKD PNAPKRPPSAFFLFCSEYRPKIKGEHPGLSIGDVAKKLGEMWNNT AADDKQPYEKKAAKLKEKYEKDIAAYRAKGKPDAAKKGVVKAEKA KKKKEEEEDEEDEEEEEDEEDEDEEEDDDDE |
| 6 | IgE derived signal sequence (DNA) | ATGGACTGGACATGGATTCTCTTTCTAGTGGCCGCAGCCACAAGG GTCCACTCC |
| 7 | IgE derived signal sequence (polypeptide) | MDWTWILFLVAAATRVHS |
| 8 | HMGB1 with IgE-derived signal sequence (human, mutant, DNA) | ATGGACTGGACATGGATTCTCTTTCTAGTGGCCGCAGCCACAAGG GTCCACTCCGGCAAAGGAGATCCTAAGAAGCCGAGAGGCAAAATG TCATCATATGCATTCTTCGTGCAAACTTGTCGGGAGGAGCATAAG AAGAAGCACCCAGATGCTGCAGTCAACTTCGCTGAGTTTGCAAAG AAGTGCGCTGAGAGGTGGAAGACCATGGCAGCTAAAGAGAAAGGA AAATTTGAAGATATGGCAAAAGCGGACAAGGCCCGTTATGAAAGA GAAATGAAAACCTATATCCCTCCCAAAGGGGAGACAAAAAAGAAG TTCAAGGACCCCAATGCACCCAAGAGGCCTCCTTCGGCCTTCTTC CTCTTCTGCTCTGAGTATCGCCCAAAAATCAAAGGAGAACATCCT GGCCTGTCCATTGGTGATGTTGCGAAGAAACTGGGAGAGATGTGG AATAACACTGCTGCAGATGACAAGCAGCCTTATGAAAAGAAGGCT GCGAAGCTGAAGGAAAAATATGAAAGGATATTGCTGCATATCGA GCTAAAGGAAAGCCTGATGCAGCAAAAAAGGGAGTTGTCAAGGCT GAAAAAGCGAAGAAAAAGAAGGAAGAGGAGGAAGATGAGGAAGAT GAAGAGGATGAGGAGGAGGAGGAAGATGAAGAAGATGAAGATGAA GAAGAAGATGATGATGATGAATAA |
| 9 | HMGB1 with IgE-derived signal sequence (human, mutant, polypeptide) | MDWTWILFLVAAATRVHSGKGDPKKPRGKMSSYAFFVQTCREEHK KKHPDAAVNFAEFAKKCAERWKTMAAKEKGKFEDMAKADKARYER EMKTYIPPKGETKKKFKDPNAPKRPPSAFFLFCSEYRPKIKGEHP GLSIGDVAKKLGEMWNNTAADDKQPYEKKAAKLKEKYEKDIAAYR AKGKPDAAKKGVVKAEKAKKKKEEEEDEEDEEDEEEEEDEEDEDE EEDDDDE |
| 10 | IL15 (human, polypeptide) | MRISKPHLRSISIQCYLCLLLNSHFLTEAGIHVFILGCFSAGLPK TEANWVNVISDLKKIEDLIQSMHIDATLYTESDVHPSCKVTAMKC FLLELQVISLESGDASIHDTVENLIILANNSLSSNGNVTESGCKE CEELEEKNIKEFLQSFVHIVQMFINTS |
| 11 | IL-7 (mouse, DNA) | ATGTTCCATGTTTCTTTTAGATATATCTTTGGAATTCCTCCACTG ATCCTTGTTCTGCTGCCTGTCACATCATCTGAGTGCCACATTAAA GACAAAGAAGGTAAAGCATATGAGAGTGTACTGATGATCAGCATC GATGAATTGGACAAAATGACAGGAACTGATAGTAATTGCCCGAAT AATGAACCAAACTTTTTTAGAAAACATGTATGTGATGATACAAAG GAAGCTGCTTTTCTAAATCGTGCTGCTCGCAAGTTGAAGCAATTT CTTAAAATGAATATCAGTGAAGAATTCAATGTCCACTTACTAACA GTATCACAAGGCACACAAACACTGGTGAACTGCACAAGTAAGGAA GAAAAAAACGTAAAGGAACAGAAAAAGAATGATGCATGTTTCCTA AAGAGACTACTGAGAGAAATAAAAACTTGTTGGAATAAAATTTTG AAGGGCAGTATATAA |
| 12 | IL-7 (human, DNA) | ATGTTCCATGTTTCTTTTAGGTATATCTTTGGACTTCCTCCCCTG ATCCTTGTTCTGTTGCCAGTAGCATCATCTGATTGTGATATTGAA GGTAAAGATGGCAAACAATATGAGAGTGTTCTAATGGTCAGCATC GATCAATTATTGGACAGCATGAAAGAAATTGGTAGCAATTGCCTG AATAATGAATTTAACTTTTTTAAAAGACATATCTGTGATGCTAAT AAGGAAGGTATGTTTTTATTCCGTGCTGCTCGCAAGTTGAGGCAA |

TABLE 2-continued

Sequences

| SEQ ID NO: | PROTEIN/ NUCLEIC ACID NAME | SEQUENCES |
|---|---|---|
| | | TTTCTTAAAATGAATAGCACTGGTGATTTTGATCTCCACTTATTA AAAGTTTCAGAAGGCACAACAATACTGTTGAACTGCACTGGCCAG GTTAAAGGAAGAAAACCAGCTGCCCTGGGTGAAGCCCAACCAACA AAGAGTTTGGAAGAAAATAAATCTTTAAAGGAACAGAAAAAACTG AATGACTTGTGTTTCCTAAAGAGACTATTACAAGAGATAAAAACT TGTTGGAATAAAATTTTGATGGGCACTAAAGAACACTGA |
| 13 | IL-7 (mouse, protein) | MFHVSFRYIFGIPPLILVLLPVTSSECHIKDKEGKAYESVLMISI DELDKMTGTDSNCPNNEPNFFRKHVCDDTKEAAFLNRAARKLKQF LKMNISEEFNVHLLTVSQGTQTLVNCTSKEEKNVKEQKKNDACFL KRLLREIKTCWNKILKGSI |
| 14 | IL-7 (human, protein) | MFHVSFRYIFGLPPLILVLLPVASSDCDIEGKDGKQYESVLMVSI DQLLDSMKEIGSNCLNNEFNFFKRHICDANKEGMFLFRAARKLRQ FLKMNSTGDFDLHLLKVSEGTTILLLNCTGQVKGRKPAALGEAQPT KSLEENKSLKEQKKLNDLCFLKRLLQEIKTCWNKILMGTKEH |
| 15 | CXCR4 (Y157A, human, DNA) | ATGGAGGGGATCAGTATATACACTTCGATAACTACACCGAGGAA ATGGGCTCAGGGGACTATGACTCCATGAAGGAACCCTGTTTCCGT GAAGAAAATGCTAATTTCAATAAAATCTTCCTGCCCACCATCTAC TCCATCATCTTCTTAACTGGCATTGTGGGCAATGGATTGGTCATC CTGGTCATGGGTTACCAGAAGAAACTGAGAAGCATGACGGACAAG TACAGGCTGCACCTGTCAGTGGCCGACCTCCTCTTTGTCATCACG CTTCCCTTCTGGGCAGTTGATGCCGTGGCAAACTGGTACTTTGGG AACTTCCTATGCAAGGCAGTCCATGTCATCTACACAGTCAACCTC TACAGCAGTGTCCTCATCCTGGCCTTCATCAGTCTGGACCGCTAC CTGGCCATCGTCCACGCCACCAACAGTCAGAGGCCAAGGAAGCTG TTGGCTGAAAAGGTGGTCGCTGTTGGCGTCTGGATCCCTGCCCTC CTGCTGACTATTCCCGACTTCATCTTTGCCAACGTCAGTGAGGCA GATGACAGATATATCTGTGACCGCTTCTACCCCAATGACTTGTGG GTGGTTGTGTTCCAGTTTCAGCACATCATGGTTGGCCTTATCCTG CCTGGTATTGTCATCCTGTCCTGCTATTGCATTATCATCTCCAAG CTGTCACACTCAAGGGCCACCAGAAGCGCAAGGCCCTCAAGACC ACAGTCATCCTCATCCTGGCTTTCTTCGCCTGTTGGCTGCCTTAC TACATTGGGATCAGCATCGACTCCTTCATCCTCCTGGAAATCATC AAGCAAGGGTGTGAGTTTGAGAACACTGTGCACAAGTGGATTTCC ATCACCGAGGCCCTAGCTTTCTTCCACTGTTGTCTGAACCCCATC CTCTATGCTTTCCTTGGAGCCAAATTTAAAACCTCTGCCCAGCAC GCACTCACCTCTGTGAGCAGAGGGTCCAGCCTCAAGATCCTCTCC AAAGGAAAGCGAGGTGGACATTCATCTGTTTCCACTGAGTCTGAG TCTTCAAGTTTTCACTCCAGCTAA |
| 16 | CXCR4 (Y159A, mouse, DNA) | ATGGAACCGATCAGTGTGAGTATATACACTTCTGATAACTACTCT GAAGAAGTGGGTTCTGGAGACTATGACTCCAACAAGGAACCCTGC TTCCGGGATGAAAACGTCCATTTCAATAGGATCTTCCTGCCCACC ATCTACTTCATCATCTTCTTGACTGGCATAGTCGGCAATGGATTG GTGATCCTGGTCATGGGTTACCAGAAGAAGCTAAGGAGCATGACG GACAAGTACCGGCTGCACCTGTCAGTGGCTGACCTCCTCTTTGTC ATCACACTCCCCTTCTGGGCAGTTGATGCCATGGCTGACTGGTAC TTTGGGAAATTTTTGTGTAAGGCTGTCCATATCATCTACACTGTC AACCTCTACAGCAGCGTTCTCATCCTGGCCTTCATCAGCCTGGAC CGATACCTCGCTATTGTCCACGCCACCAACAGTCAGAGGCCAAGG AAACTGCTGGCTGAAAAGGCAGTCGCTGTGGGCGTCTGGATCCCA GCCCTCCTCCTGACTATACCTGACTTCATCTTTGCCGACGTCAGC CAGGGGGACATCAGTCAGGGGATGACAGGTACATCTGTGACCGC CTTTACCCCGATAGCCTGTGGATGGTGGTGTTTCAATTCCAGCAT ATAATGGTGGGTCTCGTCCTGCCCGGCATCGTCATCCTCTCCTGT TACTGCATCATCATCTCTAAGCTGTCACACTCCAAGGGCCACCAG AAGCGCAAGGCCCTCAAGACGACAGTCATCCTCATCCTAGCTTTC TTTGCCTGCTGGCTGCCATATTATGTGGGGATCAGCATCGACTCC TTCATCCTTTTGGGGGTCATCAAGCAAGGATGTGACTTCGAGAGC ATCGTGCACAAGTGGATCTCCATCACAGAGGCCCTCGCCTTCTTC CACTGTTGCCTGAACCCCATCCTCTATGCCTTCCTCGGGGCCAAG TTCAAAAGCTCTGCCCAGCATGCACTCAACTCCATGAGCAGAGGC TCCAGCCTCAAGATCCTTTCCAAAGGAAAGCGGGGTGGACACTCT TCCGTCTCCACGGAGTCAGAATCCTCCAGTTTTCACTCCAGCTAA |
| 17 | CXCR4 (wild-type, human, DNA) | ATGGAGGGGATCAGTATATACACTTCGATAACTACACCGAGGAA ATGGGCTCAGGGGACTATGACTCCATGAAGGAACCCTGTTTCCGT GAAGAAAATGCTAATTTCAATAAAATCTTCCTGCCCACCATCTAC TCCATCATCTTCTTAACTGGCATTGTGGGCAATGGATTGGTCATC CTGGTCATGGGTTACCAGAAGAAACTGAGAAGCATGACGGACAAG TACAGGCTGCACCTGTCAGTGGCCGACCTCCTCTTTGTCATCACG CTTCCCTTCTGGGCAGTTGATGCCGTGGCAAACTGGTACTTTGGG |

TABLE 2-continued

Sequences

| SEQ ID NO: | PROTEIN/ NUCLEIC ACID NAME | SEQUENCES |
|---|---|---|
|  |  | AACTTCCTATGCAAGGCAGTCCATGTCATCTACACAGTCAACCTC TACAGCAGTGTCCTCATCCTGGCCTTCATCAGTCTGGACCGCTAC CTGGCCATCGTCCACGCCACCAACAGTCAGAGGCCAAGGAAGCTG TTGGCTGAAAAGGTGGTCTATGTTGGCGTCTGGATCCCTGCCCTC CTGCTGACTATTCCCGACTTCATCTTTGCCAACGTCAGTGAGGCA GATGACAGATATATCTGTGACCGCTTCTACCCCAATGACTTGTGG GTGGTTGTGTTCCAGTTTCAGCACATCATGGTTGGCCTTATCCTG CCTGGTATTGTCATCCTGTCCTGCTATTGCATTATCATCTCCAAG CTGTCACACTCCAAGGGCCACCAGAAGCGCAAGGCCCTCAAGACC ACAGTCATCCTCATCCTGGCTTTCTTCGCCTGTTGGCTGCCTTAC TACATTGGGATCAGCATCGACTCCTTCATCCTCCTGGAAATCATC AAGCAAGGGTGTGAGTTTGAGAACACTGTGCACAAGTGGATTTCC ATCACCGAGGCCCTAGCTTTCTTCCACTGTTGTCTGAACCCCATC CTCTATGCTTTCCTTGGAGCCAAATTTAAAACCTCTGCCCAGCAC GCACTCACCTCTGTGAGCAGAGGGTCCAGCCTCAAGATCCTCTCC AAAGGAAAGCGAGGTGGACATTCATCTGTTTCCACTGAGTCTGAG TCTTCAAGTTTTCACTCCAGCTAA |
| 18 | CXCR4 (Y157A, human) (polypeptide) | MEGISIYTSDNYTEEMGSGDYDSMKEPCFREENANFNKIFLPTIY SIIFLTGIVGNGLVILVMGYQKKLRSMTDKYRLHLSVADLLFVIT LPFWAVDAVANWYFGNFLCKAVHVIYTVNLYSSVLILAFISLDRY LAIVHATNSQRPRKLLAEKVVAVGVWIPALLLTIPDFIFANVSEA DDRYICDRFYPNDLWVVVFQFQHIMVGLILPGIVILSCYCIIISK LSHSKGHQKRKALKTTVILILAFFACWLPYYIGISIDSFILLEII KQGCEFENTVHKWISITEALAFFHCCLNPILYAFLGAKFKTSAQH ALTSVSRGSSLKILSKGKRGGHSSVSTESESSSFHSS |
| 19 | CXCR4 (Y159A, mouse) (polypeptide) | MEPISVSIYTSDNYSEEVGSGDYDSNKEPCFRDENVHFNRIFLPT IYFIIFLTGIVGNGLVILVMGYQKKLRSMTDKYRLHLSVADLLFV ITLPFWAVDAMADWYFGKFLCKAVHIIYTVNLYSSVLILAFISLD RYLAIVHATNSQRPRKLLAEKAVAVGVWIPALLLTIPDFIFADVS QGDISQGDDRYICDRLYPDSLWMVVFQFQHIMVGLVLPGIVILSC YCIIISKLSHSKGHQKRKALKTTVILILAFFACWLPYYVGISIDS FILLGVIKQGCDFESIVHKWISITEALAFFHCCLNPILYAFLGAK FKSSAQHALNSMSRGSSLKILSKGKRGGHSSVSTESESSSFHSS |
| 20 | CXCR4 (wild-type, human, polypeptide) | MEGISIYTSDNYTEEMGSGDYDSMKEPCFREENANFNKIFLPTIY SIIFLTGIVGNGLVILVMGYQKKLRSMTDKYRLHLSVADLLFVIT LPFWAVDAVANWYFGNFLCKAVHVIYTVNLYSSVLILAFISLDRY LAIVHATNSQRPRKLLAEKVVYVGVWIPALLLTIPDFIFANVSEA DDRYICDRFYPNDLWVVVFQFQHIMVGLILPGIVILSCYCIIISK LSHSKGHQKRKALKTTVILILAFFACWLPYYIGISIDSFILLEII KQGCEFENTVHKWISITEALAFFHCCLNPILYAFLGAKFKTSAQH ALTSVSRGSSLKILSKGKRGGHSSVSTESESSSFHSS |
| 21 | CCR2 (Human, DNA) | ATGCTGTCCACATCTCGTTCTCGGTTTATCAGAAATACCAACGAG AGCGGTGAAGAAGTCACCACCTTTTTTGATTATGATTACGGTGCT CCCTGTCATAAATTTGACGTGAAGCAAATTGGGGCCCAACTCCTG CCTCCGCTCTACTCGCTGGTGTTCATCTTTGGTTTTGTGGGCAAC ATGCTGGTCGTCCTCATCTTAATAAACTGCAAAAAGCTGAAGTGC TTGACTGACATTTACCTGCTCAACCTGGCCATCTCTGATCTGCTT TTTCTTATTACTCTCCCATTGTGGGCTCACTCTGCTGCAAATGAG TGGGTCTTTGGGAATGCAATGTGCAAATTATTCACAGGGCTGTAT CACATCGGTTATTTTGGCGGAATCTTCTTCATCATCCTCCTGACA ATCGATAGATACCTGGCTATTGTCCATGCTGTGTTTGCTTTAAAA GCCAGGACGGTCACCTTTGGGGTGGTGACAAGTGTGATCACCTGG TTGGTGGCTGTGTTTGCTTCTGTCCCAGGAATCATCTTTACTAAA TGCCAGAAAGAAGATTCTGTTTATGTCTGTGGCCCTTATTTTCCA CGAGGATGGAATAATTTCCACACAATAATGAGGAACATTTTGGGG CTGGTCCTGCCGCTGCTCATCATGGTCATCTGCTACTCGGGAATC CTGAAAACCCTGCTTCGGTGTCGAAACGAGAAGAAGAGGCATAGG GCAGTGAGAGTCATCTTCACCATCATGATTGTTTACTTTCTCTTC TGGACTCCCTATAATATTGTCATTCTCCTGAACACCTTCCAGGAA TTCTTCGGCCTGAGTAACTGTGAAAGCACCAGTCAACTGGACCAA GCCACGCAGGTGACAGAGACTCTTGGGATGACTCACTGCTGCATC AATCCCATCATCTATGCCTTCGTGGGGAGAAGTTCAGAAGCCTT TTTCACATAGCTCTTGCTGTAGGATTGCCCCACTCCAAAACCA GTGTGTGGAGGTCCAGGAGTGAGACCAGGAAAGAATGTGAAAGTG ACTACACAAGGACTCCTCGATGGTCGTGGACAAAGGAAAGTCAATT GGCAGAGCCCCTGAAGCCAGTCTTCAGGACAAAGAAGGAGCCTAG |
| 22 | CCR2 (Mouse, DNA) | ATGGAAGACAATAATATGTTACCTCAGTTCATCCACGGCATACTA TCAACATCTCATTCTCTATTTACACGAAGTATCCAAGAGCTTGAT GAAGGGGCCACCACACCGTATGACTACGATGATGGTGAGCCTTGT |

TABLE 2-continued

Sequences

| SEQ ID NO: | PROTEIN/ NUCLEIC ACID NAME | SEQUENCES |
|---|---|---|
| | | CATAAAACCAGTGTGAAGCAAATTGGAGCTTGGATCCTGCCTCCA<br>CTCTACTCCCTGGTATTCATCTTTGGTTTTGTGGGCAACATGTTG<br>GTCATTATAATTCTGATAGGCTGTAAAAAGCTGAAGAGCATGACT<br>GATATCTATCTGCTCAACTTGGCCATCTCTGACCTGCTCTTCCTG<br>CTCACATTACCATTCTGGGCTCACTATGCTGCAAATGAGTGGGTC<br>TTTGGGAATATAATGTGTAAAGTATTCACAGGGCTCTATCACATT<br>GGTTATTTTGGTGGAATCTTTTTCATTATCCTCCTGACAATTGAT<br>AGGTACTTGGCTATTGTTCATGCTGTGTTTGCTTTAAAAGCCAGG<br>ACAGTTACCTTTGGGGTGATAACAAGTGTAGTCACTTGGGTGGTG<br>GCTGTGTTTGCCTCTCTACCAGGAATCATATTTACTAAATCCAAA<br>CAAGATGATCACCATTACACCTGTGGCCCTTATTTTACACAACTA<br>TGGAAGAATTTCCAAACAATAATGAGAAATATCTTGAGCCTGATC<br>CTGCCTCTACTTGTCATGGTCATCTGCTACTCAGGAATTCTCCAC<br>ACCCTGTTTCGCTGTAGGAATGAGAAGAAGAGGCACAGGGCTGTG<br>AGGCTCATCTTTGCCATCATGATTGTCTACTTTCTCTTCTGGACT<br>CCATACAATATTGTTCTCTTCTTGACCACCTTCCAGGAATCCTTG<br>GGAATGAGTAACTGTGTGATTGACAAGCACTTAGACCAGGCCATG<br>CAGGTGACAGAGACTCTTGGAATGACACACTGCTGCATTAATCCT<br>GTCATTTATGCCTTTGTTGGAGAGAAGTTCCGAAGGTATCTCTCC<br>ATATTTTTCAGAAAGCACATTGCTAAACGTCTCTGCAAACAGTGC<br>CCAGTTTTCTATAGGGAGACAGCAGATCGAGTAAGCTCTACATTC<br>ACTCCTTCCACTGGGGAGCAAGAGGTCTCGGTTGGGTTGTAA |
| 23 | CCR2 (Human, protein) | MLSTSRSRFIRNTNESGEEVTTFFDYDYGAPCHKFDVKQIGAQLL<br>PPLYSLVFIFGFVGNMLVVLILINCKKLKCLTDIYLLNLAISDLL<br>FLITLPLWAHSAANEWVFGNAMCKLFTGLYHIGYFGGIFFIILLT<br>IDRYLAIVHAVFALKARTVTFGVVTSVITWLVAVFASVPGIIFTK<br>CQKEDSVYVCGPYFPRGWNNFHTIMRNILGLVLPLLIMVICYSGI<br>LKTLLRCRNEKKRHRAVRVIFTIMIVYFLFWTPYNIVILLNTFQE<br>FFGLSNCESTSQLDQATQVTETLGMTHCCINPIIYAFVGEKFRSL<br>FHIALGCRIAPLQKPVCGGPGVRPGKNVKVTTQGLLDGRGKGKSI<br>GRAPEASLQDKEGA |
| 24 | CCR2 (Mouse, protein) | MEDNNMLPQFIHGILSTSHSLFTRSIQELDEGATTPYDYDDGEPC<br>HKTSVKQIGAWILPPLYSLVFIFGFVGNMLVIIILIGCKKLKSMT<br>DIYLLNLAISDLLFLLTLPFWAHYAANEWVFGNIMCKVFTGLYHI<br>GYFGGIFFHILLTIDRYLAIVHAVFALKARTVTFGVITSVVTWVV<br>AVFASLPGIIFTKSKQDDHHYTCGPYFTQLWKNFQTIMRNILSLI<br>LPLLVMVICYSGILHTLFRCRNEKKRHRAVRLIFAIMIVYFLFWT<br>PYNIVLFLTTFQESLGMSNCVIDKHLDQAMQVTETLGMTHCCINP<br>VIYAFVGEKFRRYLSIFFRKHIAKRLCKQCPVFYRETADRVSSTF<br>TPSTGEQEVSVGL |
| 25 | PH-20 (human, full-length) (DNA) | ATGGGAGTGCTAAAATTCAAGCACATCTTTTTCAGAAGCTTTGTT<br>AAATCAAGTGGAGTATCCCAGATAGTTTTCACCTTCCTTCTGATT<br>CCATGTTGCTTGACTCTGAATTTCAGAGCACCTCCTGTTATTCCA<br>AATGTGCCTTTCCTCTGGGCCTGGAATGCCCCAAGTGAATTTTGT<br>CTTGGAAAATTTGATGAGCCACTAGATATGAGCCGTCTTCTCTTTC<br>ATAGGAAGCCCCCGAATAAACGCCACCGGGCAAGGTGTTACAATA<br>TTTTATGTTGATAGACTTGGCTACTATCCTTACATAGATTCAATC<br>ACAGGAGTAACTGTGAATGGAGGAATCCCCCAGAAGATTTCCTTA<br>CAAGACCATCTGGACAAAGCTAAGAAAGACATTACATTTTATATG<br>CCAGTAGACAATTTGGGAATGGCTGTTATTGACTGGGAAGAATGG<br>AGACCCACTTGGGCAAGAAACTGGAAACCTAAAGATGTTTACAAG<br>AATAGGTCTATTGAATTGGTTCAGCAACAAAATGTACAACTTAGT<br>CTCACAGAGGCCACTGAGAAAGCAAAACAAGAATTTGAAAAGGCA<br>GGGAAGGATTTCCTGGTAGAGACTATAAAATTGGGAAAATTACTT<br>CGGCCAAATCACTTGTGGGGTTATTATCTTTTTCCGGATTGTTAC<br>AACCATCACTATAAGAAACCCGGTTACAATGGAAGTTGCTTCAAT<br>GTAGAAATAAAAAGAAATGATGATCTCAGCTGGTTGTGGAATGAA<br>AGCACTGCTCTTTACCCATCCATTTATTTGAACACTCAGCAGTCT<br>CCTGTAGCTGCTACACTCTATGTGCGCAATCGAGTTCGGGAAGCC<br>ATCAGAGTTTCCAAAATACCTGATGCAAAAAGTCCACTTCCGGTT<br>TTTGCATATACCCGCATAGTTTTTACTGATCAAGTTTTGAAATTC<br>CTTTCTCAAGATGAACTTGTGTATACATTTGGCGAAACTGTTGCT<br>CTGGGTGCTTCTGGAATTGTAATATGGGGAACCCTCAGTATAATG<br>CGAAGTATGAAATCTTGCTTGCTCCTAGACAATTACATGGAGACT<br>ATACTGAATCCTTACATAATCAACGTCACACTAGCAGCCAAAATG<br>TGTAGCCAAGTGCTTTGCCAGGAGCAAGGAGTGTGTATAAGGAAA<br>AACTGGAATTCAAGTGACTATCTTCACCTCAACCCAGATAATTTT<br>GCTATTCAACTTGAGAAGGTGGAAAGTTCACAGTACGTGGAAAA<br>CCGACACTTGAAGACCTGGAGCAATTTTCTGAAAAATTTTATTGC<br>AGCTGTTATAGCACCTTGAGTTGTAAGGAGAAAGCTGATGTAAAA<br>GACACTGATGCTGTTGATGTGTGTATTGCTGATGGTGTCTGTATA |

TABLE 2-continued

Sequences

| SEQ ID NO: | PROTEIN/ NUCLEIC ACID NAME | SEQUENCES |
|---|---|---|
| | | GATGCTTTTCTAAAACCTCCCATGGAGACAGAAGAACCTCAAATT TTCTACAATGCTTCACCCTCCACACTATCTGCCACAATGTTCATT GTTAGTATTTTGTTTCTTATCATTTCTTCTGTAGCGAGTTTGTAA |
| 26 | PH-20 (human, full-length) (protein) | MGVLKFKHIFFRSFVKSSGVSQIVFTFLLIPCCLTLNFRAPPVIP NVPFLWAWNAPSEFCLGKFDEPLDMSLFSFIGSPRINATGQGVTI FYVDRLGYYPYIDSITGVTVNGGIPQKISLQDHLDKAKKDITFYM PVDNLGMAVIDWEEWRPTWARNWKPKDVYKNRSIELVQQQNVQLS LTEATEKAKQEFEKAGKDFLVETIKLGKLLRPNHLWGYYLFPDCY NHHYKKPGYNGSCFNVEIKRNDDLSWLWNESTALYPSIYLNTQQS PVAATLYVRNRVREAIRVSKIPDAKSPLPVFAYTRIVFTDQVLKF LSQDELVYTFGETVALGASGIVIWGTLSIMRSMKSCLLLDNYMET ILNPYIINVTLAAKMCSQVLCQEQGVCIRKNWNSSDYLHLNPDNF AIQLEKGGKFTVRGKPTLEDLEQFSEKFYCSCYSTLSCKEKADVK DTDAVDVCIADGVCIDAFLKPPMETEEPQIFYNASPSTLSATMFI VSILFLIISSVASL |
| 27 | Hyaluronidase (DNA) | CCGCGATACGAATGTTCAAACGCCAGATTATGAAAAGTTGAGGAA CACATGGCTGAACGTTAACTACGGTTATGATCAGTATGATGGAAA GAATGACGCAATGAAGAAGAAGTTTGATGCTACGGAGAAAGAGGC AGAGAAATTACTCAGTAGCATGAAAACTGAAAGTGGAAGGACTTA CTTGTGGGATAGTGCAAAAGATTTAGATAACAAGTCTGCGGATAT GACTCGTACCTATCGTAATATTGAGAAAATCGCAGAAGCGATGAA GCATAAAGATACTAAGTTAAATACTCCGGATAATAAAAACAAAGT TAAAGATGCCCTTGAGTGGCTGCATAAAAATGCCTATGGAAAAGA ACCGGTGAAAAAACTTGAAGAACTAAAACAAATTTCTCAAAATC AGCACCTCAAAAGAATACAAACTTAAATTGGTGGGATTATGAAAT TGGAACACCTAGAGCACTAACAAATACCCTTATACTCTTAAAAGA AGATTTTACTGATGAAGAAAAGAAAAAAATACACTGCCCCTATTAA AACTTTCGCCCCAAAAAGTGATGAAATATTATCTTCTGTAGGAAA AGCTGAACCTGCTAAAGGCGGAAATTTAGTAGACATTTCTAAAGT AAAACTTTTAGAAAGTATTATCGAAGAAGATGCAACTATGATGAA AGAATCAATAGAGGCATTTAATAAAGTCTTCACTTACGTTCAAAG TAATGCAACTGGTAAAGAACGTAATGGATTCTATAAAGACGGCTC TTATATTGATCATCAAGACGTCCCATACACTGGTGCTTATGGCGT TGTACTCTTAGAGGGGATTTCTCAAATGATGCCGATGATAAAAGA AACACCTTTTAAAGATAGTAATCAAATGATACAACATTAAAGTC GTGGATTGATGAAGGATTTATGCCACTCATTTATAAAGGTGAAAT GATGGATTTATCACGTGGTAGAGCCATTAGCCGTGAAAATGAAAC GAGTCACTCAACATCTGCAACTGTAATGAAATCATTGTTGAGATT AAGTGATGCCATGGATGAGTCAACAAAAGCTAAATATAAGCAAAT CGTTAAAACTTCTGTTAAATCTGATTCAAGTTATAAACAAAACGA TTATTTAAGCTCTTATTCAGATATAAGCAAAATGAAGTCTTTAAT TGAAGACAGCACTATTTCTACTAACGGTTTAACACAACAACTTAA AATATATAATGACATGAATCGTGTCACCTATCATAACAAAGACTT AGACTTTGCATTTGGCTTAAGTATGACGTCGAAAAACGTCGCACA TTACGAAAGTATCAACGGAGAGAACTTAAAAGGTTGGCACACTGG TGCTGGAATGTCTTATTTATACAATAGCGATGTGAAACACTACCG TGATAACTTCTGGGCGACAGCTGATATGAAACGTTTAGCAGGTAC TACAACTTTAGATAATGAAGAACCTAAAGAAAATAAGAACTCCGA TAAAACTTTTGTAGGCGGAACAAAATTCGATGACCAACATGCTAG TATCGGAATGGATTTTGAAAATCAGGACAAAACTTTAACTGCCAA AAAATCATATTTCATATTAAACGATAAAATTGTCTTCTTAGGAAC TGGCATTAAAAGTACTGATTCATCAAAGAATCCAGTGACAACGAT TGAAAATCGCAAATCGAATGGGTATACGTTATTTACAGACGATAA ACAAACAACCGCTTCAAATATTAATGATCAGGAAACCAATTCAGT CTTTTTAGAGTCCACAGATACAAAAAAGAACATCGGTTATCATTT TTTAAACGAATCGAAAATAACTGTAAAAAAAGAAAGTCATACTGG TAAGTGGAGTGATATAAATAAAAGTCAAAAGTCAGATGACAAAAC TGATGAGTATTATGAAGTAACTCAAAAGCATTCTAATACAGATGA TAAATATGCATATGTCTTGTATCCAGGCTTATCTAAAGATAATTT TAAATCCAAAGCAAGCCAAGTAACTATCGTTAAACAAGATGATGA CTTCCACATTGTGAAAGATAATGAATCGGTTTGGGCTGGTGTCAA TTATAGTAATAGCACTCAAACTTTTGACATTAACAACACCAAGGT TGAGGTTAAAGCGAAAGGGATGTTCATTTTGAAAAACAAGGACGA TAATACGTACGAATGCTCATTCTATAATCCTGAGTCTACGAATAC GGCTTCAGACATAGAAAGTAAGATCAGTATGACGGGATACTCAAT CACGAATAAAAACAAGTACGTCCAACGAAAGTGGTGTGCATTT CGAGTTGACTAAATATGCTGCCGCGATGTCTGGAGCAGGTCCGTG GGCAGCCTGGCCATTCCTACTCTCACTGGCGCTCATGCTACTATG GCTGCTCTCATGA |

TABLE 2-continued

Sequences

| SEQ ID NO: | PROTEIN/ NUCLEIC ACID NAME | SEQUENCES |
|---|---|---|
| 28 | Hyaluronidase (protein) | GRDTNVQTPDYEKLRNTWLNVNYGYDQYDEKNDAMKKKFDATEKE AEKLLSSMKTESGRTYLWDSAKDLDNKSADMTRTYRNIEKIAEAM KHKDTKLNTPDNKNKVKDALEWLHKNAYGKEPVKKLEELKTNFSK SAPQKNTNLNWWDYEIGTPRALTNTLILLKEDFTDEEKKKYTAPI KTFAPKSDEILSSVGKAEPAKGGNLVDISKVKLLESIIEEDATMM KESIEAFNKVFTYVQSNATGKERNGFYKDGSYIDHQDVPYTGAYG VVLLEGISQMMPMIKETPFKDSNQNDTTLKSWIDEGFMPLIYKGE MMDLSRGRAISRENETSHSTSATVMKSLLRLSDAMDESTKAKYKQ IVKTSVKSDSSYKQNDYLSSYSDISKMKSLIEDSTISTNGLTQQL KIYNDMNRVTYHNKDLDFAFGLSMTSKNVAHYESINGENLKGWHT GAGMSYLYNSDVKHYRDNFWATADMKRLAGTTTLDNEEPKENKNS DKTFVGGTKFDDQHASIGMDFENQDKTLTAKKSYFILNDKIVFLG TGIKSTDSSKNPVTTIENRKSNGYTLFTDDKQTTASNINDQETNS VFLESTDTKKNIGYHFLNESKITVKKESHTGKWSDINKSQKSDDK TDEYYEVTQKHSNTDDKYAYVLYPGLSKDNFKSKASQVTIVKQDD DPFHIVKDNESVWAGVNYSNSTQTFDINNTKVEVKAKGMFILKNKD DNTYECSFYNPESTNTASDIESKISMTGYSITNKNTSTSNESGVH FELTKYAAAMSGAGPWAAWPFLLSLALMLLWLLS |
| 29 | Hyaluronidase with IgE-derived signal sequence (DNA) | ATGGACTGGACATGGATTCTCTTTCTAGTGGCCGCAGCCACAAGG GTCCACAGCGGCCGCGATACGAATGTTCAAACGCCAGATTATGAA AAGTTGAGGAACACATGGCTGAACGTTAACTACGGTTATGATCAG TATGATGAGAAGAATGACGCAATGAAGAAGTTTGATGCTACG GAGAAAGAGGCAGAGAATTACTCAGTAGCATGAAAACTGAAAGT GGAAGGACTTACTTGTGGGATAGTGCAAAAGATTTAGATAACAAG TCTGCGGATATGACTCGTACCTATCGTAATATTGAGAAAATCGCA GAAGCGATGAAGCATAAAGATACTAAGTTAAATACTCCGGATAAT AAAAACAAAGTTAAAGATGCCCTTGAGTGGCTGCATAAAAATGCC TATGGAAAAGAACCGGTGAAAAAACTTGAAGAACTAAAAACAAAT TTCTCAAAATCAGCACCTCAAAAGAATACAAACTTAAATTGGTGG GATTATGAAATTGGAACACCTAGAGCACTAACAAATACCCTTATA CTCTTAAAAGAAGATTTTACTGATGAAGAAAAGAAAAAATACACT GCCCCTATTAAAACTTTCGCCCCAAAAAGTGATGAAATATTATCT TCTGTAGGAAAAGCTGAACCTGCTAAAGGCGGAAATTTAGTAGAC ATTTCTAAAGTAAAACTTTTAGAAAGTATTATCGAAGAAGATGCA ACTATGATGAAAGAATCAATAGAGGCATTTAATAAAGTCTTCACT TACGTTCAAAGTAATGCAACTGGTAAAGAACGTAATGGATTCTAT AAAGACGGCTCTTATATTGATCATCAAGACGTCCCATACACTGGT GCTTATGGCGTTGTACTCTTAGAGGGGATTTCTCAAATGATGCCG ATGATAAAAGAAACACCTTTTAAAGATAGTAATCAAAATGATACA ACATTAAAGTCGTGGATTGATGAAGGATTTATGCCACTCATTTAT AAAGGTGAAATGATGGATTTATCACGTGGTAGAGCCATTAGCCGT GAAAATGAAACGAGTCACTCAACATCTGCAACTGTAATGAAATCA TTGTTGAGATTAAGTGATGCCATGGATGAGTCAACAAAAGCTAAA TATAAGCAAATCGTTAAAACTTCTGTTAAATCTGATTCAAGTTAT AAACAAAACGATTATTTAAGCTCTTATTCAGATATAAGCAAAATG AAGTCTTTAATTGAAGACAGCACTATTTCTACTAACGGTTTAACA CAACAACTTAAAATATATAATGACATGAATCGTGTCACCTATCAT AACAAAGACTTAGACTTTGCATTTGGCTTAAGTATGACGTCGAAA AACGTCGCACATTACGAAAGTATCAACGGAGAGAACTTAAAAGGT TGGCACACTGGTGCTGGAATGTCTTATTTATACAATAGCGATGTG AAACACTACCGTGATAACTTCTGGGCGACAGCTGATATGAAACGT TTAGCAGGTACTACAACTTTAGATAATGAAGAACCTAAAGAAAAT AAGAACTCCGATAAAACTTTTGTAGGCGGAACAAAATTCGATGAC CAACATGCTAGTATCGGAATGGATTTTGAAAATCAGGACAAAACT TTAACTGCCAAAAAATCATATTTCATATTAAACGATAAAATTGTC TTCTTAGGAACTGGCATTAAAAGTACTGATTCATCAAAGAATCCA GTGACAACGATTGAAAATCGCAAATCGAATGGGTATACGTTATTT ACAGACGATAAACAAACAACCGCTTCAAATATTAATGATCAGGAA ACCAATTCAGTCTTTTTAGAGTCCACAGATACAAAAAAGAACATC GGTTATCATTTTTTAAACGAATCGAAAATAACTGTAAAAAAAGAA AGTCATACTGGTAAGTGGAGTGATATAAATAAAAGTCAAAAGTCA GATGACAAAACTGATGAGTATTATGAAGTAACTCAAAAGCATTCT AATACAGATGATAAATATGCATATGTCTTGTATCCAGGCTTATCT AAAGATAATTTTAAATCCAAAGCAAGCCAAGTAACTATCGTTAAA CAAGATGATGACTTCCACATTGTGAAAGATAATGAATCGGTTTGG GCTGGTGTCAATTATAGTAATAGCACTCAAACTTTTGACATTAAC AACACCAAGGTTGAGGTTAAAGCGAAAGGGATGTTCATTTTGAAA AACAAGGACGATAATACGTACGAATGCTCATTCTATAATCCTGAG TCTACGAATACGGCTTCAGACATAGAAAGTAAGATCAGTATGACG GGATACTCAATCACGAATAAAAACACAAGTACGTCCAACGAAAGT |

TABLE 2-continued

Sequences

| SEQ ID NO: | PROTEIN/ NUCLEIC ACID NAME | SEQUENCES |
|---|---|---|
| | | GGTGTGCATTTCGAGTTGACTAAATATGCTGCCGCGATGTCTGGA GCAGGTCCGTGGGCAGCCTGGCCATTCCTACTCTCACTGGCGCTC ATGCTACTATGGCTGCTCTCATGA |
| 30 | Hyaluronidase with IgE-derived signal sequence (protein) | MDWTWILFLVAAATRVHSGRDTNVQTPDYEKLRNTWLNVNYGYDQ YDEKNDAMKKKFDATEKEAEKLLSSMKTESGRTYLWDSAKDLDNK SADMTRTYRNIEKIAEAMKHKDTKLNTPDNKNKVKDALEWLHKNA YGKEPVKKLEELKTNFSKSAPQKNTNLNWWDYEIGTPRALTNTLI LLKEDFTDEEKKKYTAPIKTFAPKSDEILSSVGKAEPAKGGNLVD ISKVKLLESIIEEDATMMKESIEAFNKVFTYVQSNATGKERNGFY KDGSYIDHQDVPYTGAYGVVLLEGISQMMPMIKETPFKDSNQNDT TLKSWIDEGFMPLIYKGEMMDLSRGRAISRENETSHSTSATVMKS LLRLSDAMDESTKAKYKQIVKTSVKSDSSYKQNDYLSSYSDISKM KSLIEDSTISTNGLTQQLKIYNDMNRVTYHNKDLDFAFGLSMTSK NVAHYESINGENLKGWHTGAGMSYLYNSDVKHYRDNFWATADMKR LAGTTTLDNEEPKENKNSDKTFVGGTKFDDQHASIGMDFENQDKT LTAKKSYFILNDKIVFLGTGIKSTDSSKNPVTTIENRKSNGYTLF TDDKQTTASNINDQETNSVFLESTDTKKNIGYHFLNESKITVKKE SHTGKWSDINKSQKSDDKTDEYYEVTQKHSNTDDKYAYVLYPGLS KDNFKSKASQVTIVKQDDDFHIVKDNESVWAGVNYSNSTQTFDIN NTKVEVKAKGMFILKNKDDNTYECSFYNPESTNTASDIESKISMT GYSITNKNTSTSNESGVHFELTKYAAAMSGAGPWAAWPFLLSLAL MLLWLLS |
| 31 | IL-2 (mouse, DNA) | AATTCTATGGCTCCGACTTCAAGTTCTACCAAGAAGACCCAGCTT CAATTAGAACATTTACTTCTAGATTTACAAATGATTCTGAATGGT ATCAACAATTATAAGAATCCAAAGCTTACTCGTATGTTGACCTTT AAATTCTATATGCCTAAGAAGGCTACTGAATTAAAACACCTGCAG TGTTTAGAAGAAGAGCTCAAACCGTTAGAAGAAGTTCTGAATCTG GCTCAATCTAAAAACTTCCATTTACGTCCACGAGATCTTATCTCT AATATTAACGTAATCGTTTTGGAACTTAAAGGATCCGAAACTACC TTCATGTGTGAATATGCTGACGAAACCGCTACGATCGTAGAATTT CTTAATCGATGGATTACTTTCTGTCAATCTATTATCTCTACCTTA ACTTGAGTCGACG |
| 32 | IL-2 (human, DNA) | ATGTACAGGATGCAACTCCTGTCTTGCATTGCACTAAGTCTTGCA CTTGTCACAAACAGTGCACCTACTTCAAGTTCTACAAAGAAAACA CAGCTACAACTGGAGCATTTACTGCTGGATTTACAGATGATTTTG AATGGAATTAATAATTACAAGAATCCCAAACTCACCAGGATGCTC ACATTTAAGTTTTACATGCCCAAGAAGGCCACAGAACTGAAACAT CTTCAGTGTCTAGAAGAAGAACTCAAACCTCTGGAGGAAGTGCTA AATTTAGCTCAAAGCAAAAACTTTCACTTAAGACCCAGGGACTTA ATCAGCAATATCAACGTAATAGTTCTGGAACTAAAGGGATCTGAA ACAACATTCATGTGTGAATATGCTGATGAGACAGCAACCATTGTA GAATTTCTGAACAGATGGATTACCTTTTGTCAAAGCATCATCTCA ACACTGACTTGA |
| 33 | IL-2 (mouse, protein) | MYSMQLASCVTLTLVLLVNSAPTSSSTSSSTAEAQQQQQQQQQQQ QHLEQLLMDLQELLSRMENYRNLKLPRMLTFKFYLPKQATELKDL QCLEDELGPLRHVLDLTQSKSFQLEDAENFISNIRVTVVKLKGSD NTFECQFDDESATVVDFLRRWIAFCQSIISTSPQ |
| 34 | IL-2 (human, protein) | MYRMQLLSCIALSLALVTNSAPTSSSTKKTQLQLEHLLLDLQMIL NGINNYKNPKLTRMLTFKFYMPKKATELKHLQCLEEELKPLEEVL NLAQSKNFHLRPRDLISNINVIVLELKGSETTFMCEYADETATIV EFLNRWITFCQSIISTLT |
| 35 | loxP | ATAACTTCGTATAGCATACATTATACGAAGTTAT |
| 36 | dnIRF7 (DNA) | ATGCCAGGGCTCCCTGCTGGGGAGCTGTACGGGTGGGCAGTAGAG ACGACCCCCAGCCCCGGGCCCAGCCCGCGGCACTAACGACAGG GAGGCCGCGGCCCCAGAGTCCCCGCACCAGGCAGAGCCGTACCTG TCACCCTCCCCAAGCGCCTGCACCGCGGTGCAAGAGCCCAGCCCA GGGGCGCTGGACGTGACCATCATGTACAAGGGCCGCACGGTGCTG CAGAAGGTGGTGGGACACCCGAGCTGCACGTTCCTATACGGCCCC CCAGACCCAGCTGTCCGGGCCACAGACCCCCAGCAGGTAGCATTC CCCAGCCCTGCCGAGCTACCGGACCAGAAGCAGCTGCGCTACACG GAGGAACTGCTGCGGCACGTGGCCCCTGGGTTGCACTGGAGCTT CGGGGGCCCACAGCTGTGGGCCGGCGCATGGGCAAGTGCAAGGTG TACTGGGAGGTGGGCGGACCCCCAGGCTCCGCCAGCCCCTCCACC CCAGCCTGCCTGCTGCCTCGGAACTGTGACACCCCCATCTTCGAC TTCAGAGTCTTCTTCCAAGAGCTGGTGGAATTCCGGGCACGGCAG CGCCGTGGCTCCCCACGCTATACCATCTACCTGGGCTTCGGGCAG GACCTGTCAGCTGGGAGGCCCAAGGAGAAGAGCCTGGTCCTGGTG |

TABLE 2-continued

Sequences

| SEQ ID NO: | PROTEIN/ NUCLEIC ACID NAME | SEQUENCES |
|---|---|---|
| | | AAGCTGGAACCCTGGCTGTGCCGAGTGCACCTAGAGGGCACGCAG CGTGAGGGTGTGTCTTCCCTGGATAGCAGCAGCCTCAGCCTCTGC CTGTCCAGCGCCAACAGCCTCTATGACACATCGAGTGCTTCCTT ATGGAGCTGGAGCAGCCCGCCTAG |
| 37 | dnIRF7 (polypeptide) | MPGLPAGELYGWAVETTPSPGPQPAALTTGEAAAPESPHQAEPYL SPSPSACTAVQEPSPGALDVTIMYKGRTVLQKVVGHPSCTFLYGP PDPAVRATDPQQVAFPSPAELPDQKQLRYTEELLRHVAPGLHLEL RGPQLWARRMGKCKVYWEVGGPPGSASPSTPACLLPRNCDTPIFD FRVFFQELVEFRARQRRGSPRYTIYLGFGQDLSAGRPKEKSLVLV KLEPWLCRVHLEGTQREGVSSLDSSSLSLCLSSANSLYDDIECFL MELEQPA |
| 38 | vIRF3 (DNA) | ATGGCAGGCAGACGGCTTACATGGATCAGCGAGTTTATCGTAGGT GCCCTGGACTCTGATAAGTACCCCTTGGTAAAATGGCTTGATCGG TCAACGGGAACTTTTCTGGCTCCCGCTGCGAGAAATGACGTAATA CCACTGGATTCCCTGCAGTTTTTCATAGATTTTAAGAGGGAGTGT TTGTCAAAGGGGCTCCACCCCCGAGATCTTTTGGGTAGTCCAATA ACTGCGTTCGGTAAGATTTGTACAACTAGCCGACGGCTGAGACGA TTGCCCGGTGAAGAGTACGAAGTTGTCCAAGGAATCAACTGCCGG CGGTGGCGGCTTCTCTGCGCCGAAGTGAAAGAATGCTGGTGGTGT GTACACGCGCGAACACATCTGCACTCCGGAAGCAGCCTTTGGGAA ATTCTCTACCAGCATTCCGTAAGACTTGAAAAGCACCGACGAAGG CCCAGGCCCTTTGTAGGAGAGAACAGTGATTCTTCTGAGGAAGAC CACCCTGCTTTCTGCGATGTGCCCGTAACACAAACGGGCGCGGAG AGCGAGGACAGCGGCGATGAAGGTCCTTCCACCAGACACAGCGCC TCAGGTGTCCAACCGGTAGACGATGCTAATGCCGACTCCCCTGGT TCTGGAGACGAAGGTCCCAGCACCCGCCATAGCGACAGTCAACCT CCTCCCGCCGATGAAACCACTGTCCACACAGACAATGTAGAGGAC GATTTGACACTCCTTGATAAAGAGTCCGCGTGCGCATTGATGTAT CACGTGGGGCAGGAGATGGACATGCTTATGCGAGCGATGTGCGAT GAAGACTTGTTTGATTTGCTTGGGATCCCTGAGGATGTAATAGCC ACAAGTCAGCCTGGTGGTGATACGGACGCCTCGGCGTTGTTACG GAGGGTAGTATTGCTGCTAGCGCCGTGGGCGCAGGGGTTGAAGAT GTCTACTTGGCAGGAGCCCTCGAAGCACAGAATGTCGCAGGGGAG TATGTGCTTGAGATCTCTGATGAGGAAGTAGACGATGGCGCTGGA CTCCCTCCCGCCTCAAGGCGGAGACCCGTTGTTGGAGAGTTCTTG TGGGACGACGGTCCTAGGCGCCACGAAAGGCCAACGACCCGCAGA ATTAGGCACAGGAAACTCAGGTCTGCGTACTACAGAGTAGCACGG CCCCCAGTGATGATCACGGACAGGCTGGGCGTTGAGGTTTTTTAC TTCGGAAGGCCGGCTATGAGCCTTGAAGTGGAACGAAAAGTATTC ATCTTGTGTAGCCAGAATCCGCTGGCAGACATCAGTCACTCCTGC CTCCATTCACGAAAAGGGCTTCGAGTCCTGCTGCCAAAACCGGAC GACAATAATACTGGTCCGGGAGATGTTAACCTCCTCGCAGCGGTG TTGAGATCTTTTGCATCAGGCTTGGTGATAGTCTCACTCCGAAGC GGAATCTACGTGAAGAACCTCTGCAAGAGCACCGTCCTGTATCAC GGAAACAACCCCCCAAAAAAGTTTGGCGTTATATGCGGACTTTCA TCCAGAGCAGTTCTTGACGTGTTTAATGTTGCCCAATACCGGATT CAGGGCCATGAACACATCAAAAAGACAACCGTCTTCATCGGGGGA GACCCGACTTCAGCGGAGCAATTTGATATGGTGCCACTCGTTATC AAGCTTCGGTTGAGATCAGTGACGTGCGACGATTAA |
| 39 | vIRF3 (polypeptide) | MAGRRLTWISEFIVGALDSDKYPLVKWLDRSTGTFLAPAARNDVI PLDSLQFFIDFKRECLSKGLHPRDLLGSPITAFGKICTTSRRLRR LPGEEYEVVQGINCRRWRLLCAEVKECWWCVHARTHLHSGSSLWE ILYQHSVRLEKHRRRPRPFVGENSDSSEEDHPAFCDVPVTQTGAE SEDSGDEGPSTRHSASGVQPVDDANADSPGSGDEGPSTRHSDSQP PPADETTVHTDNVEDDLTLLDKESACALMYHVGQEMDMLMRAMCD EDLFDLLGIPEDVIATSQPGGDTDASGVVTEGSIAASAVGAGVED VYLAGALEAQNVAGEYVLEISDEEVDDGAGLPPASRRRPVVGEFL WDDGPRRHERPTTRRIRHRKLRSAYYRVARPPVMITDRLGVEVFY FGRPAMSLEVERKVFILCSQNPLADISHSCLHSRKGLRVLLPKPD DNNTGPGDVNLLAAVLRSFASGLVIVSLRSGIYVKNLCKSTVLYH GNNPPKKFGVICGLSSRAVLDVFNVAQYRIQGHEHIKKTTVFIGG DPTSAEQFDMVPLVIKLRLRSVTCDD |

We claim:

1. A composition, wherein the composition comprises:
   an oncolytic virus, wherein the oncolytic virus comprises a genome modification,
   wherein the genome modification comprises an exogenous nucleic acid encoding for an MHC I inhibitor, wherein the MHC I inhibitor comprises vIRF3.

2. The composition of claim 1, wherein the genome modification further comprises:
   a deletion or functional deletion of an endogenous nucleic acid encoding an MHC II inhibitor; or
   an exogenous nucleic acid that results in activation or enhanced activation of MHC II presentation.

3. The composition of claim 2, wherein the deletion or functional deletion of the endogenous nucleic acid encoding the MHC II inhibitor comprises a deletion or functional deletion of a vaccinia virus gene encoding protein A35.

4. The composition of claim 3, wherein the deletion or functional deletion of the vaccinia virus gene encoding protein A35 is a deletion or functional deletion of gene WR158.

5. The composition of claim 2, wherein the exogenous nucleic acid that results in activation or enhanced activation of the MHC II presentation encodes for a protein selected from:
   a) an apoptosis inhibitor protein;
   b) a necrotic cell death activator protein;
   c) an autophagy enhancer protein;
   d) an asparaginyl endopeptidase;
   e) a class II transactivator;
   f) an interferon-gamma;
   g) a Toll-like receptor activator; or
   h) a dendritic cell maturation activator.

6. The composition of claim 5, wherein the exogenous nucleic acid that results in activation or enhanced activation of MHC II presentation encodes for the autophagy enhancer protein, and wherein the autophagy enhancer protein is HMGB1 or a functional domain or a variant thereof.

7. The composition of claim 5, wherein the exogenous nucleic acid that results in activation or enhanced activation of MHC II presentation encodes for the dendritic cell maturation activator, wherein the dendritic cell maturation activator comprises osteopontin, TNF-alpha, or a functional fragment or variant thereof.

8. The composition of claim 5, wherein the protein encoded by the exogenous nucleic acid is fused to a secretion sequence, a cell permeabilizing domain, or a combination thereof.

9. The composition of claim 1, wherein the oncolytic virus comprises a poxvirus, an adeno associated virus, an adenovirus, Newcastle disease virus (NDV), Reovirus (RV), mengovirus, Myxoma virus (MYXV), Measles virus (MV), Herpes Simplex virus (HSV), Vaccinia virus (VV), Vesicular Stomatitis virus (VSV), and Polio virus (PV).

10. The composition of claim 9, wherein the poxvirus comprises a betaentomopoxvirus, a yatapoxvirus, a cervidpoxvirus, a gammaentomopoxvirus, a leporipoxvirus, a suipoxvirus, a molluscipoxvirus, a crocodylidpoxvirus, an alphaentomopoxvirus, a capripoxvirus, an avipoxvirus, or a parapoxvirus.

11. The composition of claim 1, wherein the oncolytic virus is a vaccinia virus.

12. The composition of claim 1, wherein the MHC I inhibitor causes an inhibition or partial inhibition of MHC I presentation.

13. The composition of claim 1, wherein the genome modification reduces an immune response targeting a virus-infected tumor cell and increases an immune response targeting cells surrounding the virus-infected tumor cell.

14. The composition of claim 1, wherein the genome modification further comprises mutation or a complete or a partial deletion of a viral gene comprising at least one of: A52R, B15R, K7R, A46R, N1L, E3L, K1L, M2L, C16, N2R, B8R, B18R, or VH1 of a vaccinia virus or a functional domain or fragment or variant thereof, or any combinations thereof.

15. The composition of claim 1, wherein the genome modification further comprises a deletion of a thymidine kinase gene.

16. The composition of claim 1, wherein the oncolytic virus is a vaccinia virus, and the vaccinia virus is a Western Reserve strain Vaccinia virus (ATCC VR-1354), a Copenhagen strain, an IHD strain, a Wyeth strain (ATCC VR-325), a NYCBOH strain, a Tian Tan strain, a Lister strain, an Ankara strain (ATCC VR-1508 or ATTC VR1566), a USSR strain, or an ACAM2000 strain.

17. A pharmaceutical composition comprising the composition according claim 1 and a pharmaceutically acceptable excipient.

18. The pharmaceutical composition of claim 17, wherein the excipient comprises one or more of a buffering agent, a stabilizer, an antioxidant, a binder, a diluent, a dispersing agent, a rate controlling agent, a lubricant, a glidant, a disintegrant, a plasticizer, a preservative, or any combinations thereof.

19. The pharmaceutical composition of claim 17, wherein the excipient comprises di-sodium hydrogen phosphate dihydrate, sodium dihydrogen phosphate dihydrate, sodium chloride, myo-inositol, sorbitol, or any combinations thereof.

20. The pharmaceutical composition of claim 17, wherein the pharmaceutical composition does not comprise a preservative.

21. The pharmaceutical composition of claim 17, further comprising one or more of a preservative, a diluent, and a carrier.

22. The pharmaceutical composition of claim 17, further comprising an additional active ingredient or a salt thereof.

23. The pharmaceutical composition of claim 17, wherein the excipient is sterile water.

24. The pharmaceutical composition of claim 17, further comprising an additional active ingredient, wherein the additional active ingredient is an anti-cancer agent or a further oncolytic virus.

* * * * *

SEQUENCE LISTING

```
Sequence total quantity: 39
SEQ ID NO: 1                    moltype = DNA   length = 130
FEATURE                         Location/Qualifiers
misc_feature                    1..130
                                note = Description of Artificial Sequence:
                                Syntheticpolynucleotide
source                          1..130
                                mol_type = other DNA
                                organism = synthetic construct
SEQUENCE: 1
tcactaattc caaacccacc cgcttttat agtaagtttt tcacccataa ataataaata   60
caataattaa tttctcgtaa aagtagaaaa tatattctaa tttattgcac ggtaaggaag  120
tagatcataa                                                         130

SEQ ID NO: 2                    moltype = DNA   length = 210
FEATURE                         Location/Qualifiers
source                          1..210
                                mol_type = genomic DNA
                                organism = Cowpox virus
SEQUENCE: 2
atgttcatca tgcgcgagag catttaccgc gtgatgattg tcattttgta tttgagcttg   60
atttcttcgt ttttggttat ctgctctatg gagcacggct acttccagga gggcatcagc  120
cgcttcaaga tttgtcccta tcattggtat aaacaacaca tgagtttatt gtttcgtcgt  180
tactatcaca agctggatag tatcatctag                                   210

SEQ ID NO: 3                    moltype = AA   length = 69
FEATURE                         Location/Qualifiers
source                          1..69
                                mol_type = protein
                                organism = Cowpox virus
SEQUENCE: 3
MFIMRESIYR VMIVILYLSL ISSFLVICSM EHGYFQEGIS RFKICPYHWY KQHMSLLFRR   60
YYHKLDSII                                                          69

SEQ ID NO: 4                    moltype = DNA   length = 645
FEATURE                         Location/Qualifiers
misc_feature                    1..645
                                note = Description of Artificial Sequence:
                                Syntheticpolynucleotide
source                          1..645
                                mol_type = other DNA
                                organism = synthetic construct
SEQUENCE: 4
ggcaaaggag atcctaagaa gccgagaggc aaaatgtcat catatgcatt cttcgtgcaa   60
acttgtcggg aggagcataa gaagaagcac ccagatgctg cagtcaactt cgctgagttt  120
gcaaagaagt gcgctgagag gtggaagacc atggcagcta agagaaagg aaaatttgaa  180
gatatgcaa aagcggacaa ggcccgttat gaaagagaaa tgaaaaccta tatccctccc  240
aaaggggaga caaaaaagaa gttcaaggac cccaatgcac ccaagaggcc tccttcggcc  300
ttcttcctct tctgctctga gtatcgccca aaaatcaaag gagaacatcc tggcctgtcc  360
attggtgatg ttgcgaagaa actgggagag atgtggaata acactgctgc agatgacaag  420
cagcctatg aaaagaaggc tgcgaagctg aaggaaaaat atgaaaagga tattgctgca  480
tatcgagcta aaggaaagcc tgatgcagca aaaaagggga ttgtcaaggc tgaaaaagcg  540
aagaaaaaga aggaagagga ggaagatgag gaagatgaag aggatgagga ggaggaggaa  600
gatgaagaag atgaagatga agaagaagat gatgatgatg aataa                  645

SEQ ID NO: 5                    moltype = AA   length = 214
FEATURE                         Location/Qualifiers
REGION                          1..214
                                note = Description of Artificial Sequence:
                                Syntheticpolypeptide
source                          1..214
                                mol_type = protein
                                organism = synthetic construct
SEQUENCE: 5
GKGDPKKPRG KMSSYAFFVQ TCREEHKKKH PDAAVNFAEF AKKCAERWKT MAAKEKGKFE   60
DMAKADKARY EREMKTYIPP KGETKKKFKD PNAPKRPPSA FFLFCSEYRP KIKGEHPGLS  120
IGDVAKKLGE MWNNTAADDK QPYEKKAAKL KEKYEKDIAA YRAKGKPDAA KKGVVKAEKA  180
KKKKEEEEDE EDEEDEEEE DEEDEDEEED DDDE                               214

SEQ ID NO: 6                    moltype = DNA   length = 54
FEATURE                         Location/Qualifiers
misc_feature                    1..54
                                note = Description of Unknown:IgE derived signal sequence
source                          1..54
                                mol_type = other DNA
                                organism = unidentified
SEQUENCE: 6
atggactgga catggattct ctttctagtg gccgcagcca caagggtcca ctcc          54
```

```
SEQ ID NO: 7              moltype = AA   length = 18
FEATURE                   Location/Qualifiers
REGION                    1..18
                          note = Description of Unknown:IgE derived signal sequence
source                    1..18
                          mol_type = protein
                          organism = unidentified
SEQUENCE: 7
MDWTWILFLV AAATRVHS                                                       18

SEQ ID NO: 8              moltype = DNA   length = 699
FEATURE                   Location/Qualifiers
misc_feature              1..699
                          note = Description of Artificial Sequence:
                          Syntheticpolynucleotide
source                    1..699
                          mol_type = other DNA
                          organism = synthetic construct
SEQUENCE: 8
atggactgga catggattct ctttctagtg gccgcagcca caagggtcca ctccggcaaa    60
ggagatccta agaagccgag aggcaaaatg tcatcatatg cattcttcgt gcaaacttgt   120
cgggaggagc ataagaagaa gcacccagat gctgcagtca acttcgctga gtttgcaaag   180
aagtgcgctg agaggtggaa gaccatggca gctaaagaga aaggaaaatt tgaagatatg   240
gcaaagcgg acaaggcccg ttatgaaaga gaaatgaaaa cctatatccc tcccaaaggg   300
gagacaaaaa agaagttcaa ggaccccaat gcacccaaga ggcctccttc ggccttcttc   360
ctcttctgct ctgagtatcg cccaaaaatc aaggagaaa atcctggcct gtccattggt   420
gatgttgcga gaaactggg agagatgtgg aataacactg ctgcagatga caagcagcct   480
tatgaaaaga aggctgcgaa gctgaaggaa aaatatgaaa aggatattgc tgcatatcga   540
gctaaaggaa agcctgatgc agcaaaaaag ggagttgtca aggctgaaaa agcgaagaaa   600
aagaaggaag aggaggaaga tgaggaagat gaagaggaag aggaggagga ggaagatgaa   660
gaagatgaag atgaagaaga agatgatgat gatgaataa                           699

SEQ ID NO: 9              moltype = AA   length = 232
FEATURE                   Location/Qualifiers
REGION                    1..232
                          note = Description of Artificial Sequence:
                          Syntheticpolypeptide
source                    1..232
                          mol_type = protein
                          organism = synthetic construct
SEQUENCE: 9
MDWTWILFLV AAATRVHSGK GDPKKPRGKM SSYAFFVQTC REEHKKKHPD AAVNFAEFAK    60
KCAERWKTMA AKEKGKFEDM AKADKARYER EMKTYIPPKG ETKKKFKDPN APKRPPSAFF   120
LFCSEYRPKI KGEHPGLSIG DVAKKLGEMW NNTAADDKQP YEKKAAKLKE KYEKDIAAYR   180
AKGKPDAAKK GVVKAEKAKK KKEEEEDEED EEDEEEEEDE EDEDEEEDDD DE           232

SEQ ID NO: 10             moltype = AA   length = 162
FEATURE                   Location/Qualifiers
source                    1..162
                          mol_type = protein
                          organism = Homo sapiens
SEQUENCE: 10
MRISKPHLRS ISIQCYLCLL LNSHFLTEAG IHVFILGCFS AGLPKTEANW VNVISDLKKI    60
EDLIQSMHID ATLYTESDVH PSCKVTAMKC FLLELQVISL ESGDASIHDT VENLIILANN   120
SLSSNGNVTE SGCKECEELE EKNIKEFLQS FVHIVQMFIN TS                      162

SEQ ID NO: 11             moltype = DNA   length = 465
FEATURE                   Location/Qualifiers
source                    1..465
                          mol_type = genomic DNA
                          organism = Mus sp.
SEQUENCE: 11
atgttccatg tttcttttag atatatcttt ggaattcctc cactgatcct tgttctgctg    60
cctgtcacat catctgagtg ccacattaaa gacaaagaag gtaaagcata tgagagtgta   120
ctgatgatca gcatcgatga attggacaaa atgacaggaa ctgatagtaa ttgcccgaat   180
aatgaaccaa acttttttag aaaacatgta tgtgatgata caaaggaagc tgcttttcta   240
aatcgtgctg ctcgcaagtt gaagcaattt cttaaaatga atatcagtga agaattcaat   300
gtccacttac taacagtatc acaaggcaca caaactgtg tgaactgcac aagtaaggaa   360
gaaaaaaacg taaggaaca gaaaagaat gatgcatgtt tcctaaagag actactgaga   420
gaaataaaaa cttgttggaa taaaattttg aagggcagta tataa                  465

SEQ ID NO: 12             moltype = DNA   length = 534
FEATURE                   Location/Qualifiers
source                    1..534
                          mol_type = genomic DNA
                          organism = Homo sapiens
SEQUENCE: 12
atgttccatg tttcttttag gtatatcttt ggacttcctc ccctgatcct tgttctgttg    60
```

```
ccagtagcat catctgattg tgatattgaa ggtaaagatg gcaaacaata tgagagtgtt    120
ctaatggtca gcatcgatca attattggac agcatgaaag aaattggtag caattgcctg    180
aataatgaat ttaactttt taaaagacat atctgtgatg ctaataagga aggtatgttt    240
ttattccgtg ctgctcgcaa gttgaggcaa tttcttaaaa tgaatagcac tggtgatttt    300
gatctccact tattaaaagt ttcagaaggc acaacaatac tgttgaactg cactggccag    360
gttaaaggaa gaaaaccagc tgccctgggt gaagcccaac caacaaagag tttggaagaa    420
aataaatctt taaggaaca gaaaaaactg aatgacttgt gtttcctaaa gagactatta    480
caagagataa aacttgttg gaataaaatt ttgatgggca ctaaagaaca ctga           534

SEQ ID NO: 13              moltype = AA   length = 154
FEATURE                    Location/Qualifiers
source                     1..154
                           mol_type = protein
                           organism = Mus sp.
SEQUENCE: 13
MFHVSFRYIF GIPPLILVLL PVTSSECHIK DKEGKAYESV LMISIDELDK MTGTDSNCPN    60
NEPNFFRKHV CDDTKEAAFL NRAARKLKQF LKMNISEEFN VHLLTVSQGT QTLVNCTSKE    120
EKNVKEQKKN DACFLKRLLR EIKTCWNKIL KGSI                                154

SEQ ID NO: 14              moltype = AA   length = 177
FEATURE                    Location/Qualifiers
source                     1..177
                           mol_type = protein
                           organism = Homo sapiens
SEQUENCE: 14
MFHVSFRYIF GLPPLILVLL PVASSDCDIE GKDGKQYESV LMVSIDQLLD SMKEIGSNCL    60
NNEFNFFKRH ICDANKEGMF LFRAARKLRQ FLKMNSTGDF DLHLLKVSEG TTILLNCTGQ    120
VKGRKPAALG EAQPTKSLEE NKSLKEQKKL NDLCFLKRLL QEIKTCWNKI LMGTKEH       177

SEQ ID NO: 15              moltype = DNA   length = 1059
FEATURE                    Location/Qualifiers
misc_feature               1..1059
                           note = Description of Artificial Sequence:
                           Syntheticpolynucleotide
source                     1..1059
                           mol_type = other DNA
                           organism = synthetic construct
SEQUENCE: 15
atggaggga tcagtatata cacttcagat aactacaccg aggaaatggg ctcaggggac    60
tatgactcca tgaaggaacc ctgtttccgt gaagaaaatg ctaatttcaa taaaatcttc    120
ctgcccacca tctactccat catcttctta actggcattg tgggcaatgg attggtcatc    180
ctggtcatgg gttaccagaa gaaactgaga agcatgacgg acaagtacag gctgcacctg    240
tcagtggccg acctcctctt tgtcatcacg ctttcccttc ggcagttga tgccgtggca    300
aactggtact ttgggaactt cctatgcaag gcagtccatg tcatctacac agtcaacctc    360
tacagcagtg tcctcatcct ggccttcatc agtctggacc gctacctggc catcgtccac    420
gccaccaaca gtcagaggcc aaggaagctg ttggctaaaa ggtggtcgc tgttggcgtc    480
tggatccctg ccctcctgct gactattccc gacttcatct ttgccaacgt cagtgaggca    540
gatgacagat atatctgtga ccgcttctac cccaatctgt gtgggtggt tgtgttccag    600
tttcagcaca tcatggttgg ccttatcctg cctggtattg tcatcctgtc ctgctattgc    660
attatcatct ccaagctgtc acactccaag ggccaccaga agcgcaaggc cctcaagacc    720
acagtcatcc tcatcctggc tttcttcgcc tgttggctgc cttactacat tgggatcagc    780
atcgactcct tcatcctcct ggaaaatcat caagcaaggg tgtgagtttga gaacactgtg    840
cacaagtgga tttccatcac cgaggcccta gctttcttcc actgttgtct gaaccccatc    900
ctctatgctt tccttggagc caaatttaaa acctctgccc agcacgcact cacctctgtg    960
agcagagggt ccagcctcaa gatcctctcc aaaggaaagc gaggtggaca ttcatctgtt    1020
tccactgagt ctgagtcttc aagttttcac tccagctaa                           1059

SEQ ID NO: 16              moltype = DNA   length = 1080
FEATURE                    Location/Qualifiers
misc_feature               1..1080
                           note = Description of Artificial Sequence:
                           Syntheticpolynucleotide
source                     1..1080
                           mol_type = other DNA
                           organism = synthetic construct
SEQUENCE: 16
atggaaccga tcagtgtgag tatatacact tctgataact actctgaaga agtgggttct    60
ggagactatg actccaacaa ggaaccctgc ttccgggatg aaaacgtcca tttcaatagg    120
atcttcctgc ccaccatcta cttcatcatc ttcttgactg gcatatcgg caatggttct    180
gtgatcctgg tcatgggtta ccagaagaag ctaaggagca tgacggacaa gtaccggctg    240
cacctgtcag tggctgacct cctctttgtc atcacactcc ccttctgggc agttgatgcc    300
atggctgact ggtactttgg gaattttttg tgtaaggctg tccatatcat ctacactgtc    360
aacctctaca gcagcgttct catcctggcc ttcatcagcc tggaccgata cctcgctatt    420
gtccacgcca ccaacagtca gaggccaagg aaactgctgg ctgaaaaggc agtcgctgt    480
ggcgtctgga tccagccct cctgactg atacctgact tcatctttgc cgacgtcagc    540
caggggaca tcagtcaggg gatgacagg tacatctgtg accgccttta cccgatagc    600
ctgtggatgt tgtgtttca attccagcat ataatggtgg gtctcgtcct gcccggcatc    660
gtcatcctc cctgttactg catcatcatc tctaagctgt cacactccaa gggccaccag    720
aagcgcaagg ccctcaagac gacagtcatc ctcatcctag ctttctttgc ctgctggctg    780
```

```
                                     -continued
ccatattatg tgggaatcag catcgactcc ttcatccttt tgggggtcat caagcaagga       840
tgtgacttcg agagcatcgt gcacaagtgg atctccatca cagaggccct cgccttcttc       900
cactgttgcc tgaaccccat cctctatgcc ttcctggggg ccaagttcaa aagctctgcc       960
cagcatgcac tcaactccat gagcagaggc tccagcctca agatcctttc aaaggaaagc      1020
cggggtggac actcttccgt ctccacgagt cagaatcct ccagttttca ctccagctaa      1080

SEQ ID NO: 17          moltype = DNA   length = 1059
FEATURE                Location/Qualifiers
source                 1..1059
                       mol_type = genomic DNA
                       organism = Homo sapiens
SEQUENCE: 17
atggagggga tcagtatata cacttcagat aactacaccg aggaaatggg ctcaggggac        60
tatgactcca tgaaggaacc ctgtttccgt gaagaaaatg ctaatttcaa taaaatcttc       120
ctgcccacca tctactccat catcttctta actggcattg tgggcaatgg attggtcatc       180
ctggtcatgg gttaccagaa gaaactgaga agcatgacgg acaagtacag gctgcacctg       240
tcagtggccg acctcctctt tgtcatcacg cttcccttct gggcagttga tgccgtggca       300
aactggtact ttgggaactt cctatgcaag gcagtccata tcatctacac agtcaacctc       360
tacagcagtg tcctcatcct ggccttcatc agtctggacc gctacctggc catcgtccac       420
gccaccaaca tcagaggcc aaggaagctg ttggctgaaa aggtggtcta tgttggcgtc       480
tggatccctg ccctcctgct gactattccc gacttcatct ttgccaacgt cagtgaggca       540
gatgacagat atatctgtga ccgcttctac cccaatgact tgtgggtggt tgtgttccag       600
tttcagcaca tcatggttgg ccttatcctg cctggtattg tcatcctgtc ctgctattgc       660
attatcatct ccaagctgtc acactccaag ggccaccaga agcgcaaggc cctcaagacc       720
acagtcatcc tcatcctggc ctttcttgcc tgttggctgc cttactacat tgggatcagc       780
atcgactcct tcatcctcct ggaaatcatc aagcaaggt gtgagtttga aaactgttg       840
cacaagtgga tttccatcac cgaggcccta gctttcttcc actgttgtct gaacccatc       900
ctctatgctt tccttggagc caaatttaaa acctctgccc agcacgcact cacctctgtg       960
agcagaggt ccagcctcaa gatcctctcc aaaggaaagc gaggtggaca ttcatctgtt      1020
tccactgagt ctgagtcttc aagttttcac tccagctaa                            1059

SEQ ID NO: 18          moltype = AA    length = 352
FEATURE                Location/Qualifiers
REGION                 1..352
                       note = Description of Artificial Sequence:
                       Syntheticpolypeptide
source                 1..352
                       mol_type = protein
                       organism = synthetic construct
SEQUENCE: 18
MEGISIYTSD NYTEEMGSGD YDSMKEPCFR EENANFNKIF LPTIYSIIFL TGIVGNGLVI        60
LVMGYQKKLR SMTDKYRLHL SVADLLFVIT LPFWAVDAVA NWYFGNFLCK AVHVIYTVNL       120
YSSVLILAFI SLDRYLAIVH ATNSQRPRKL LAEKVVAVGV WIPALLLTIP DFIFANVSEA       180
DDRYICDRFY PNDLWVVVFQ FQHIMVGLIL PGIVILSCYC IIISKLSHSK GHQKRKALKT       240
TVILILAFFA CWLPYYIGIS IDSFILLEII KQGCEFENTV HKWISITEAL AFFHCCLNPI       300
LYAFLGAKFK TSAQHALTSV SRGSSLKILS KGKRGGHSSV STESESSSFH SS              352

SEQ ID NO: 19          moltype = AA    length = 359
FEATURE                Location/Qualifiers
REGION                 1..359
                       note = Description of Artificial Sequence:
                       Syntheticpolypeptide
source                 1..359
                       mol_type = protein
                       organism = synthetic construct
SEQUENCE: 19
MEPISVSIYT SDNYSEEVGS GDYDSNKEPC FRDENVHFNR IFLPTIYFII FLTGIVGNGL        60
VILVMGYQKK LRSMTDKYRL HLSVADLLFV ITLPFWAVDA MADWYFGKFL CKAVHIIYTV       120
NLYSSVLILA FISLDRYLAI VHATNSQRPR KLLAEKAVAV GVWIPALLLT IPDFIFADVS       180
QGDISQGDDR YICDRLYPDS LWMVVFQFQH IMVGLVLPGI VILSCYCIII SKLSHSKGHQ       240
KRKALKTTVI LILAFFACWL PYYVGISIDS FILLGVIKQG CDFESIVHKW ISITEALAFF       300
HCCLNPILYA FLGAKFKSSA QHALNSMSRG SSLKILSKGK RGGHSSVSTE SESSSFHSS       359

SEQ ID NO: 20          moltype = AA    length = 352
FEATURE                Location/Qualifiers
source                 1..352
                       mol_type = protein
                       organism = Homo sapiens
SEQUENCE: 20
MEGISIYTSD NYTEEMGSGD YDSMKEPCFR EENANFNKIF LPTIYSIIFL TGIVGNGLVI        60
LVMGYQKKLR SMTDKYRLHL SVADLLFVIT LPFWAVDAVA NWYFGNFLCK AVHVIYTVNL       120
YSSVLILAFI SLDRYLAIVH ATNSQRPRKL LAEKVVYVGV WIPALLLTIP DFIFANVSEA       180
DDRYICDRFY PNDLWVVVFQ FQHIMVGLIL PGIVILSCYC IIISKLSHSK GHQKRKALKT       240
TVILILAFFA CWLPYYIGIS IDSFILLEII KQGCEFENTV HKWISITEAL AFFHCCLNPI       300
LYAFLGAKFK TSAQHALTSV SRGSSLKILS KGKRGGHSSV STESESSSFH SS              352

SEQ ID NO: 21          moltype = DNA    length = 1125
FEATURE                Location/Qualifiers
source                 1..1125
```

|  |  |  |  |  |  |
|---|---|---|---|---|---|
|  |  | mol_type = genomic DNA |  |  |  |
|  |  | organism = Homo sapiens |  |  |  |

SEQUENCE: 21

```
atgctgtcca catctcgttc tcggtttatc agaaatacca cgagagcggt gaagaagtc    60
accacctttt ttgattatga ttacggtgct ccctgtcata aatttgacgt gaagcaaatt  120
ggggcccaac tcctgcctcc gctctactcg ctggtgttca tctttggttt tgtgggcaac  180
atgctggtcg tcctcatctt aataaactgc aaaaagctga agtgcttgac tgacatttac  240
ctgctcaacc tggccatctc tgatctgctt tttcttatta ctctcccatt gtgggctcac  300
tctgctgcaa atgagtgggt ctttgggaat gcaatgtgca aattattcac agggctgtat  360
cacatcggtt attttggcgg aatcttcttc atcatcctcc tgacaatcga tagatacctg  420
gctattgtcc atgctgtgtt tgctttaaaa gccaggacgg tcacctttgg ggtggtgaca  480
agtgtgatca cctggttggt ggctgtgttt gcttctgtcc caggaatcat ctttactaaa  540
tgccagaaag aagattctgt ttatgtctgt ggcccttatt ttccacgagg atggaataat  600
ttccacacaa taatgaggaa cattttgggg ctggtcctgc cgctgctcat catggtcatc  660
tgctactcgg gaatcctgaa aaccctgctt cggtgtcgaa acgagaagaa gaggcatagg  720
gcagtgagag tcatcttcac catcatgatt gtttactttc tcttctggac tcccataat   780
attgtcattc tcctgaacac cttccaggaa ttcttcggcc tgagtaactg tgaaagcacc  840
agtcaactgg accaagccac gcaggtgaca gagactcttg ggatgactca ctgctgccata  900
aatcccatca tctatgcctt cgttgggag aagttcagaa gccttttca catagctctt   960
ggctgtagga ttgccccact ccaaaaacca gtgtgtggag gtccaggagt gagaccagga 1020
aagaatgtga aagtgactac acaaggactc ctcgatggtc gtggaaaagg aaagtcaatt 1080
ggcagagccc ctgaagccag tcttcaggac aaagaaggag cctag                 1125
```

| SEQ ID NO: 22 | moltype = DNA  length = 1122 |
|---|---|
| FEATURE | Location/Qualifiers |
| source | 1..1122 |
|  | mol_type = genomic DNA |
|  | organism = Mus sp. |

SEQUENCE: 22

```
atggaagaca ataatatgtt acctcagttc atccacggca tactatcaac atctcattct   60
ctatttacac gaagtatcca agagcttgat gaaggggcca ccacccgta tgactacgat   120
gatggtgagc cttgtcataa aaccagtgtg aagcaaattg gagctggat cctgcctcca   180
ctctactccc tggtattcat ctttggtttt gtgggcaaca tgttggtcat tataattctg   240
ataggctgta aaaagctcaa gagcatgact gatatctatc tgctcaactt ggccatctct   300
gacctgctct tcctgctcac attaccattc tgggctcact atgctgcaaa tgagtgggtc   360
tttgggaata taatgtgtaa agtattcaca gggctctatc acattggtta ttttggtgga   420
atcttttttca ttatcctcct gacaattgat aggtacttgg ctattgttca tgctgtgttt   480
gctttaaaag ccaggacagt taccttggg gtgataacaa gtgtagtcac ttgggtggta   540
gctgtgtttg cctctctacc aggaatcata ttactaaat ccaaacaaga tcatcaccat   600
tacacctgtg gcccttattt tacacaacta tggaagaatt ccaaacaat aatgagaaat   660
atcttgagcc tgatcctgcc tctacttgtc atggtcatct gctactcagg aattctccac   720
accctgtttc gctgtaggaa tgagaagaag aggcacaggg ctgtgaggct catctttgcc   780
atcatgattg tctactttct cttctggact ccatacaata ttgttctctt ctgaccacc   840
ttccaggaat ccttgggaat gagtaactgt gtgattgaca agcacttaga ccaggccatg   900
caggtgacag agactcttgg aatgacacac tgctgcatta tcctgtcat ttatgccttt   960
gttggagaga gttccgaagg tatctctccc atattttca gaaagcacat tgctaaacgt 1020
ctctgcaaac agtgcccagt tttctatag gagacacagag atcgagtaag ctctacattc 1080
actccttcca ctggggagca agaggtctcg gttgggttgt aa                   1122
```

| SEQ ID NO: 23 | moltype = AA  length = 374 |
|---|---|
| FEATURE | Location/Qualifiers |
| source | 1..374 |
|  | mol_type = protein |
|  | organism = Homo sapiens |

SEQUENCE: 23

```
MLSTSRSRFI RNTNESGEEV TTFFDYDYGA PCHKFDVKQI GAQLLPPLYS LVFIFGFVGN   60
MLVVLILINC KKLKCLTDIY LLNLAISDLL FLITLPLWAH SAANEWVFGN AMCKLFTGLY  120
HIGYFGGIFF IILLTIDRYL AIVHAVFALK ARTVTFGVVT SVITWLVAVF ASVPGIIFTK  180
CQKEDSVYVC GPYFPRGWNN FHTIMRNILG LVLPLLIMVI CYSGILKTLL RCRNEKKRHR  240
AVRVIFTIMI VYFLFWTPYN IVILLNTFQE FFGLSNCEST SQLDQATQVT ETLGMTHCCI  300
NPIIYAFVGE KFRSLFHIAL GCRIAPLQKP VCGGPGVRPG KNVKVTTQGL LDGRGKGKSI  360
GRAPEASLQD KEGA                                                   374
```

| SEQ ID NO: 24 | moltype = AA  length = 373 |
|---|---|
| FEATURE | Location/Qualifiers |
| source | 1..373 |
|  | mol_type = protein |
|  | organism = Mus sp. |

SEQUENCE: 24

```
MEDNNMLPQF IHGILSTSHS LFTRSIQELD EGATTPYDYD DGEPCHKTSV KQIGAWILPP   60
LYSLVFIFGF VGNMLVIIIL IGCKKLKSMT DIYLLNLAIS DLLFLLTLPF WAHYAANEWV  120
FGNIMCKVFT GLYHIGYFGG IFFIILLTID RYLAIVHAVF ALKARTVTFG VITSVVTWVV  180
AVFASLPGII FTKSKQDDHH YTCGPYFTQL WKNFQTIMRN ILSLILPLLV MVICYSGILH  240
TLFRCRNEKK RHRAVRLIFA IMIVYFLFWT PYNIVLFLTT FQESLGMSNC VIDKHLDQAM  300
QVTETLGMTH CCINPVIYAF VGEKFRRYLS IFFRKHIAKR LCKQCPVFYR ETADRVSSTF  360
TPSTGEQEVS VGL                                                    373
```

| SEQ ID NO: 25 | moltype = DNA  length = 1530 |
|---|---|
| FEATURE | Location/Qualifiers |

```
source                  1..1530
                        mol_type = genomic DNA
                        organism = Homo sapiens
SEQUENCE: 25
atgggagtgc taaaattcaa gcacatcttt ttcagaagct tgttaaatc aagtggagta      60
tcccagatag ttttcacctt ccttctgatt ccatgttgct tgactctgaa tttcagagca    120
cctcctgtta ttccaaatgt gcctttcctc tgggcctgga atgccccaag tgaattttgt    180
cttggaaaat ttgatgagcc actagatatg agcctcttct ctttcatagg aagcccccga    240
ataaacgcca ccgggcaagg tgttacaata ttttatgttg atagacttgg ctactatcct    300
tacatagatt caatcacagg agtaactgtg aatggaggaa tccccagaa gatttcctta    360
caagaccatc tggacaaagc taagaaagac attacatttt atatgccagt agacaatttg    420
ggaatggctc ttattgactg ggaagaatgg agacccactt gggcaagaaa ctggaaacct    480
aaagatgttt acaagaatag gtctattgaa ttggttcagc aacaaaatgt acaacttagt    540
ctcacagagg ccactgagaa agcaaaacaa gaatttgaaa aggcagggaa ggatttcctg    600
gtagagacta taaaattggg aaaattactt cggccaaatc acttgtgggg ttattatctt    660
tttccggatt gttacaacca tcactataag aaacccggtt acaatggaag ttgcttcaat    720
gtagaaataa aagaaatga tgatctcagc tggttgtgga atgaaagcac tgctctttac    780
ccatccattt atttgaacac tcagcagtct cctgtagctc tacactcta tgtgcgcaat    840
cgagttcggg aagccatcag agtttccaaa atacctgatg caaaaagtcc acttccggtt    900
tttgcatata cccgcatagt ttttactgat caagttttga aattcctttc tcaagatgaa    960
cttgtgtata catttggcga aactgttgct ctgggtgctt ctggaattgt aatatgggga   1020
acccctcagta taatgcgaag tatgaaatct tgcttgctcc tagacaatta catggagact   1080
atactgaatc cttacataat caacgtcaca ctagcagcca aaatgtgtag ccaagtgctt   1140
tgccaggagc aaggagtgtg tataaggaaa aactggaatt caagtgacta tcttcacctc   1200
aacccagata ttttgctat tcaacttgag aaaggtggaa agttcacagt acgtggaaaa   1260
ccgacacttg aagacctgga gcaattttct gaaaaatttt attgcagctg ttatagcacc   1320
ttgagttgta aggagaaagc tgatgtaaaa gacactgatg ctgttgatgt gtgtattgct   1380
gatggtgtct gtatagatgc ttttctaaaa cctcccatgg agacagaaga acctcaaatt   1440
ttctacaatg cttcaccctc cacactatct gccacaatgt tcattgttag tattttgttt   1500
cttatcattt cttctgtagc gagtttgtaa                                    1530

SEQ ID NO: 26          moltype = AA  length = 509
FEATURE                Location/Qualifiers
source                 1..509
                       mol_type = protein
                       organism = Homo sapiens
SEQUENCE: 26
MGVLKFKHIF FRSFVKSSGV SQIVFTFLLI PCCLTLNFRA PPVIPNVPFL WAWNAPSEFC     60
LGKFDEPLDM SLFSFIGSPR INATGQGVTI FYVDRLGYYP YIDSITGVTV NGGIPQKISL    120
QDHLDKAKKD ITFYMPVDNL GMAVIDWEEW RPTWARNWKP KDVYKNRSIE LVQQQNVQLS    180
LTEATEKAKQ EFEKAGKDFL VETIKLGKLL RPNHLWGYYL FPDCYNHHYK KPGYNGSCFN    240
VEIKRNDDLS WLWNESTALY PSIYLNTQQS PVAATLYVRN RVREAIRVSK IPDAKSPLPV    300
FAYTRIVFTD QVLKFLSQDE LVYTFGETVA LGASGIVIWG TLSIMRSMKS CLLLDNYMET    360
ILNPYIINVT LAAKMCSQVL CQEQGVCIRK NWNSSDYLHL NPDNFAIQLE KGGKFTVRGK    420
PTLEDLEQFS EKFYCSCYST LSCKEKADVK DTDAVDVCIA DGVCIDAFLK PPMETEEPQI    480
FYNASPSTLS ATMFIVSILF LIISSVASL                                     509

SEQ ID NO: 27          moltype = DNA  length = 2398
FEATURE                Location/Qualifiers
misc_feature           1..2398
                       note = Description of Unknown:Hyaluronidase sequence
source                 1..2398
                       mol_type = unassigned DNA
                       organism = unidentified
SEQUENCE: 27
ccgcgatacg aatgttcaaa cgccagatta tgaaaagttg aggaacacat ggctgaacgt     60
taactacggt tatgatcagt atgatgagaa gaatgacgca atgaagaaga gtttgatgc    120
tacggagaaa gaggcagaga aattactcag tagcatgaaa actgaaagtg aaggactta    180
cttgtgggat agtgcaaaag atttagataa caagtctgcg gatatgactc gtacctatcg    240
taatattgag aaaatcgcag aagcgatgaa gcataaagat actaagttaa atactccgga    300
taataaaaac aaagttaaag atgcccttga gtggctgcat aaaaatgcct atggaaaaga    360
accggtgaaa aaacttgaag aactaaaaac aaatttctca aaatcagcac ctcaaaagaa    420
tacaaactta aattggtggg attatgaaat tggaacacct agagcactaa caaataccct    480
tatactctta aaagaagatt ttactgatga agaaaagaaa aaatacactg ccctattaa    540
aactttcgcc ccaaaaagtg atgaaatatt atccttctgta ggaaaagctg aacctgctaa    600
aggcggaaat ttagtagaca tttctaaagt aaaactttta gaaagtatta tcgaagaaga    660
tgcaactatg atgaaagaat caatagaggc atttaataaa gtcttcactt acgttcaaag    720
taatgcaact ggtaaagaac gtaatggatt ctataaagac ggctcttata ttgatcatca    780
agacgtccca tacactggtg cttatgtcgt tgtactctta gaggggattt ctcaaatgat    840
gccgatgata aaagaaacac cttttaaaga tagtaatcaa atgataacaa cattaaagtc    900
gtggattgat gaaggattta tgccactcat ttataaaggt gaaatgatgg atttatcacg   960
tggtagagcc attagccgtg aaaatgaaac gagtcactca acatctgcaa ctgtaatgaa   1020
atcattgttg agattaagtg atgccatgga tgagtcaaca aaagctaaat ataagcaaat   1080
aaaact cgttaaaact ctgttaaat ctgattcaag tataaacaa acgattatt aagctctta   1140
ttcagatata agcaaaatga agtctttaat tgaagacagc actatttcta ctaacgtttt   1200
aacacaacaa cttaaaatat ataatgcat gaatcgtgtc acctatcata caaagagactt   1260
agactttgca tttggcttaa gtatgacgtc gaaaacgtc gcacattacg aaagtatcaa   1320
cggagagaac ttaaaaggtt ggcacactgg tgctggaatg tcttatttat acaatagcga   1380
tgtgaaacac taccgtgata acttctgggc gacagctgat atgaaacgtt tagcaggtac   1440
```

```
tacaacttta gataatgaag aacctaaaga aaataagaac tccgataaaa ctttttgtagg   1500
cggaacaaaa ttcgatgacc aacatgctag tatcggaatg gattttgaaa atcaggacaa   1560
aactttaact gccaaaaaat catatttcat attaaacgat aaaattgtct tcttaggaac   1620
tggcattaaa agtactgatt catcaaagaa tccagtgaca acgattgaaa atcgcaaatc   1680
gaatgggtat acgttattta cagacgataa acaaacgacc gcttcaaata ttaatgatca   1740
ggaaaccaat tcagtctttt tagagtccac agatacaaaa aagaacatcg gttatcattt   1800
tttaaacgaa tcgaaaataa ctgtaaaaaa agaaagtcat actggtaagt ggagtgatat   1860
aaataaaagt caaaagtcag atgacaaaac tgatgagtat tatgaagtaa ctcaaaagca   1920
ttctaataca gatgataaat atgcatatgt cttgtatcca ggcttatcta aagataattt   1980
taaatccaaa gcaagccaag taactatcgt taaacaagat gatgacttcc acattgtgaa   2040
agataatgaa tcggtttggg ctggtgtcaa ttatagtaat agcactcaaa cttttgacat   2100
taacaacacc aaggttgagg ttaaagcgaa agggatgttc attttgaaaa acaaggacga   2160
taatacgtac gaatgctcat tctataatcc tgagtctacg aatacggctt cagacataga   2220
aagtaagatc agtatgacgg gatactcaat cacgaataaa acacaagta cgtccaacga   2280
aagtggtgtg catttcgagt tgactaaata tgctgccgcg atgtctggag caggtccgtg   2340
ggcagcctgg ccattcctac tctcactggg gctcatgcta ctatggctgc tctcatga    2398

SEQ ID NO: 28         moltype = AA   length = 799
FEATURE               Location/Qualifiers
REGION                1..799
                      note = Description of Unknown:Hyaluronidase sequence
source                1..799
                      mol_type = protein
                      organism = unidentified
SEQUENCE: 28
GRDTNVQTPD YEKLRNTWLN VNYGYDQYDE KNDAMKKKFD ATEKEAEKLL SSMKTESGRT    60
YLWDSAKDLD NKSADMTRTY RNIEKIAEAM KHKDTKLNTP DNKNKVKDAL EWLHKNAYGK   120
EPVKKLEELK TNFSKSAPQK NTNLNWWDYE IGTPRALTNT LILLKEDFTD EEKKKYTAPI   180
KTFAPKSDEI LSSVGKAEPA KGGNLVDISK VKLLESIIEE DATMMKESIE AFNKVFTYVQ   240
SNATGKERNG FYKDGSYIDH QDVPYTGAYG VVLLEGISQM MPMIKETPFK DSNQNDTTLK   300
SWIDEGFMPL IYKGEMMDLS RGRAISRENE TSHSTSATVM KSLLRLSDAM DESTKAKYKQ   360
IVKTSVKSDS SYKQNDYLSS YSDISKMKSL IEDSTISTNG LTQQLKIYND MNRVTYHNKD   420
LDFAFGLSMT SKNVAHYESI NGENLKGWHT GAGMSYLYNS DVKHYRDNFW ATADMKRLAG   480
TTTLDNEEPK ENKNSDKTFV GGTKFDDQHA SIGMDFENQD KTLTAKKSYF ILNDKIVFLG   540
TGIKSTDSSK NPVTTIENRK SNGYTLFTDD KQTTASNIND QETNSVFLES TDTKKNIGYH   600
FLNESKITVK KESHTGKWSD INKSQKSDDK TDEYYEVTQK HSNTDDKYAY VLYPGLSKDN   660
FKSKASQVTI VKQDDDFHIV KDNESVWAGV NYSNSTQTFD INNTKVEVKA KGMFILKNKD   720
DNTYECSFYN PESTNTASDI ESKISMTGYS ITNKNTSTSN ESGVHFELTK YAAAMSGAGP   780
WAAWPFLLSL ALMLLWLLS                                                799

SEQ ID NO: 29         moltype = DNA   length = 2454
FEATURE               Location/Qualifiers
misc_feature          1..2454
                      note = Description of Artificial Sequence:
                      Syntheticpolynucleotide
source                1..2454
                      mol_type = other DNA
                      organism = synthetic construct
SEQUENCE: 29
atggactgga catggattct ctttctagtg gccgcagcca caagggtcca cagcggccgc    60
gatacgaatg ttcaaacgcc agattatgaa aagttgagga acacatggct gaacgttaac   120
tacggttatg atcagtatga tgagaagaat gacgcaatga agaagaagtt tgatgctacg   180
gagaaagagg cagagaaatt actcagtagc atgaaaactg aaagtggaag gacttacttg   240
tgggatagtg caaaagattt agataacaag tctgcggata tgactcgtac ctatcgtaat   300
attgagaaaa tcgcagaagc gatgaagcat aaagtatcta agttaaatac tccggataat   360
aaaaacaaag ttaaagatgc ccttgagtgg ctgcataaaa atgcctatgg aaaagaaccg   420
gtgaaaaaac ttgaagaact aaaaacaaat ttctcaaaat cagcacctca aagaatacaa   480
aacttaaatt ggtgggatta tgaaattgga acacctagag cactaacaaa taccctttata   540
ctcttaaaag aagattttac tgatgaagaa aagaaaaaat acactgcccc tattaaaact   600
ttcgccccaa aaagtgatga aatattatct tctgtaggaa aagctgaacc tgctaaaggc   660
ggaaatttag tagacatttc taagtaaaa cttttagaaa gtattatcga agaagatgca   720
actatgatga agaatcaat agaggcattt aataaagtct tcacttacgt tcaaagtaat   780
gcaactggta agaacgtaa tggattctat aagacggct cttatattga tcatcaagac   840
gtcccataca ctggtgctta tggcgttgta tcttagagg ggatttctca aatgatgccg   900
atgataaaag aaacaccttt taagatagt aatcaaaatg atacaacatt aaagtcgtgg   960
attgatgaag gatttatgcc actcatttat aaaggtgaaa tgatggattt atcacgtggt  1020
agagccatta gccgtgaaaa tgaaacgagt cactcaacat ctgcaactgt aatgaaatca  1080
ttgttgagat taagtgatgc catggatgag tcaacaaaag ctaaatataa gcaaatcgtt  1140
aaaacttctg ttaaatctga ttcaagttat aaacaaaacg attatttaag ctcttattca  1200
gataagca aaatgaagtc tttaattgaa gacagcacta tttctactaa cggtttaaca  1260
caacaactta aaatatataa tgacatgaat cgtgtcacct atcataacaa agacttagac  1320
tttgcatttg gcttaagtat gacgtcgaaa aacgtcgcac attacgaaag tatcaacgga  1380
gagaacttaa aaggttggca cactggtgct ggaatgtctt atttatacaa tagcgatgtg  1440
aaacactacc gtgataactt ctgggcgaca gctgatatga acgtttgac aggtactaca  1500
actttagata tgaagaacc taagaaaat aagaactccg ataaaacttt tgtaggcgga  1560
acaaaattcg atgaccaaca tgctagtatc ggaatggatt ttgaaaatca ggacaaaact  1620
ttaactgcca aaaaatcata tttcatatta acgataaaa ttgtcttctt aggaactggc  1680
attaaaagta ctgattcatc aaagaatcca gtgacaacga ttgaaaatcg caaatcgaat  1740
gggtatacgt tatttacaga cgataaacaa acaaccgctt caaatattaa tgatcaggaa  1800
```

```
accaattcag tcttttaga gtccacagat acaaaaaga acatcggtta tcatttttta  1860
aacgaatcga aaataactgt aaaaaagaa agtcatactg gtaagtggag tgatataaat  1920
aaaagtcaaa agtcagatga caaaactgat gagtattatg aagtaactca aaagcattct  1980
aatacagatg ataaatatgc atatgtcttg tatccaggct tatctaaaga taattttaaa  2040
tccaaagcaa gccaagtaac tatcgttaaa caagatgata acttccacat tgtgaaagat  2100
aatgaatcgg tttgggctgg tgtcaattat agtaatagca ctcaaacttt tgacattaac  2160
aacaccaagg ttgaggttaa agcgaaaggg atgttcattt tgaaaaacaa ggacgataat  2220
acgtacgaat gctcattcta taatcctgag tctacgaata cggcttcaga catagaaagt  2280
aagatcagta tgacgggata ctcaatcacg aataaaaaca caagtacgtc caacgaaagt  2340
ggtgtgcatt tcgagttgac taaaatatgct gccgcgatgt ctggagcagg tccgtgggca  2400
gcctggccat tcctactctc actggcgctc atgctactat ggctgctctc atga          2454

SEQ ID NO: 30          moltype = AA   length = 817
FEATURE                Location/Qualifiers
REGION                 1..817
                       note = Description of Artificial Sequence:
                       Syntheticpolypeptide
source                 1..817
                       mol_type = protein
                       organism = synthetic construct
SEQUENCE: 30
MDWTWILFLV AAATRVHSGR DTNVQTPDYE KLRNTWLNVN YGYDQYDEKN DAMKKKFDAT    60
EKEAEKLLSS MKTESGRTYL WDSAKDLDNK SADMTRTYRN IEKIAEAMKH KDTKLNTPDN   120
KNKVKDALEW LHKNAYGKEP VKKLEELKTN FSKSAPQKNT NLNWWDYEIG TPRALTNTLI   180
LLKEDFTDEE KKKYTAPIKT FAPKSDEILS SVGKAEPAKG GNLVDISKVK LLESIIEEDA   240
TMMKESIEAF NKVFTYVQSN ATGKERNGFY KDGSYIDHQD VPYTGAYGVV LLEGISQMMP   300
MIKETPFKDS NQNDTTLKSW IDEGFMPLIY KGEMMDLSRG RAISRENETS HSTSATVMKS   360
LLRLSDAMDE STKAKYKQIV KTSVKSDSSY KQNDYLSSYS DISKMKSLIE DSTISTNGLT   420
QQLKIYNDMN RVTYHNKDLD FAFGLSMTSK NVAHYESING ENLKGWHTGA GMSYLYNSDV   480
KHYRDNFWAT ADMKRLAGTT TLDNEEPKEN KNSDKTFVGG TKFDDQHASI GMDFENQDKT   540
LTAKKSYFIL NDKIVFLGTG IKSTDSSKNP VTTIENRKSN GYTLFTDDKQ TTASNINDQE   600
TNSVFLESTD TKKNIGYHFL NESKITVKKE SHTGKWSDIN KSQKSDDKTD EYYEVTQKHS   660
NTDDKYAYVL YPGLSKDNFK SKASQVTIVK QDDDFHIVKD NESVWAGVNY SNSTQTFDIN   720
NTKVEVKAKG MFILKNKDDN TYECSFYNPE STNTASDIES KISMTGYSIT NKNTSTSNES   780
GVHFELTKYA AAMSGAGPWA AWPFLLSLAL MLLWLLS                            817

SEQ ID NO: 31          moltype = DNA   length = 418
FEATURE                Location/Qualifiers
source                 1..418
                       mol_type = genomic DNA
                       organism = Mus sp.
SEQUENCE: 31
aattctatgg ctccgacttc aagttctacc aagaagaccc agcttcaatt agaacattta    60
cttctagatt tacaaatgat tctgaatggt atcaacaatt ataagaatcc aaagcttact   120
cgtatgttga cctttaaatt ctatatgcct aagaaggcta ctgaattaaa acacctgcag   180
tgtttagaag aagagctcaa accgttagaa gaagttctga atctggctca atctaaaaac   240
ttccatttac gtccacgaga tctttatctct aatattaact taatcgtttt ggaacttaaa   300
ggatccgaaa ctaccttcat tgtgtgaatat gctgacgaaa ccgctacgat cgtagaattt   360
cttaatcgat ggattacttt ctgtcaatct attatctcta ccttaacttg agtcgacg      418

SEQ ID NO: 32          moltype = DNA   length = 462
FEATURE                Location/Qualifiers
source                 1..462
                       mol_type = genomic DNA
                       organism = Homo sapiens
SEQUENCE: 32
atgtacagga tgcaactcct gtcttgcatt gcactaagtc ttgcacttgt cacaaacagt    60
gcacctactt caagttctac aaagaaaaca cagctacaac tggagcattt actgctggat   120
ttacagatga ttttgaatgg aattaataat tacaagaatc ccaaactcac caggatgctc   180
acatttaagt tttacatgcc caagaaggcc acagaactga aacatctca gtgtctagaa   240
gaagaactca aacctctgga ggaagtgcta aatttagctc aaagcaaaaa ctttcactta   300
agacccaggg acttaatcag caatatcaac gtaatagttc tggaactaaa gggatctgaa   360
acaacattca tgtgtgaata tgctgatgag acagcaacca ttgtagaatt tctgaacaga   420
tggattacct ttgtcaaag catcatctca acactgactt ga                       462

SEQ ID NO: 33          moltype = AA   length = 169
FEATURE                Location/Qualifiers
source                 1..169
                       mol_type = protein
                       organism = Mus sp.
SEQUENCE: 33
MYSMQLASCV TLTLVLLVNS APTSSSTSSS TAEAQQQQQQ QQQQQHLEQ LLMDLQELLS     60
RMENYRNLKL PRMLTFKFYL PKQATELKDL QCLEDELGPL RHVLDLTQSK SFQLEDAENF   120
ISNIRVTVVK LKGSDNTFEC QFDDESATVV DFLRRWIAFC QSIISTSPQ               169

SEQ ID NO: 34          moltype = AA   length = 153
FEATURE                Location/Qualifiers
source                 1..153
                       mol_type = protein
```

```
                        organism = Homo sapiens
SEQUENCE: 34
MYRMQLLSCI ALSLALVTNS APTSSSTKKT QLQLEHLLLD LQMILNGINN YKNPKLTRML    60
TFKFYMPKKA TELKHLQCLE EELKPLEEVL NLAQSKNFHL RPRDLISNIN VIVLELKGSE   120
TTFMCEYADE TATIVEFLNR WITFCQSIIS TLT                                153

SEQ ID NO: 35           moltype = DNA   length = 34
FEATURE                 Location/Qualifiers
misc_feature            1..34
                        note = Description of Artificial Sequence:
                        Syntheticoligonucleotide
source                  1..34
                        mol_type = other DNA
                        organism = synthetic construct
SEQUENCE: 35
ataacttcgt atagcataca ttatacgaag ttat                                34

SEQ ID NO: 36           moltype = DNA   length = 834
FEATURE                 Location/Qualifiers
misc_feature            1..834
                        note = Description of Artificial Sequence:
                        Syntheticpolynucleotide
source                  1..834
                        mol_type = other DNA
                        organism = synthetic construct
SEQUENCE: 36
atgccagggc tccctgctgg ggagctgtac gggtgggcag tagagacgac ccccagcccc    60
gggccccagc ccgcggcact aacgacaggc gaggccgcgg ccccagagtc cccgcaccag   120
gcagagccgc acctgtcacc ctccccaagc gcctgcaccg cggtgcaaga gcccagccca   180
ggggcgctgg acgtgaccat catgtacaag ggccgcacgg tgctgcagaa ggtggtggga   240
caccgagct gcacgttcct atacggcccc ccagacccag ctgtccgggc cacagaccca   300
cagcaggtag cattccccag ccctgccgag ctaccggacc agaagcagct gcgctacacg   360
gaggaactgc tgcggcacgt ggcccctggg ttgcacctgg agcttcgggg ccacagctg   420
tgggcccggc gcatgggcaa gtgcaaggtg tactgggagg tgggcggacc cccaggctcc   480
gccagccct ccaccccagc ctgcctgctg cctcggaact gtgacacccc catcttcgac   540
ttcagagtct tcttccaaga gctggtggaa ttccgggcac ggcagcgccg tggctcccca   600
cgctatacca tctacctggg cttcgggcag gacctgtcag ctgggaggcc caaggagaag   660
agcctggtcc tggtgaagct ggaaccctgg ctgtgccgag tgcacctaga gggcacgcag   720
cgtgagggtg tgtcttccct ggatagcagc agcctcagcc tctgcctgtc cagcgccaac   780
agcctctatg acgacatcga gtgcttcctt atggagctgg agcagcccgc ctag         834

SEQ ID NO: 37           moltype = AA   length = 277
FEATURE                 Location/Qualifiers
REGION                  1..277
                        note = Description of Artificial Sequence:
                        Syntheticpolypeptide
source                  1..277
                        mol_type = protein
                        organism = synthetic construct
SEQUENCE: 37
MPGLPAGELY GWAVETTPSP GPQPAALTTG EAAAPESPHQ AEPYLSPSPS ACTAVQEPSP    60
GALDVTIMYK GRTVLQKVVG HPSCTFLYGP PDPAVRATDP QQVAFPSPAE LPDQKQLRYT   120
EELLRHVAPG LHLELRGPQL WARRMGKCKV YWEVGGPPGS ASPSTPACLL PRNCDTPIFD   180
FRVFFQELVE FRARQRRGSP RYTIYLGFGQ DLSAGRPKEK SLVLVKLEPW LCRVHLEGTQ   240
REGVSSLDSS SLSLCLSSAN SLYDDIECFL MELEQPA                            277

SEQ ID NO: 38           moltype = DNA   length = 1701
FEATURE                 Location/Qualifiers
misc_feature            1..1701
                        note = Description of Artificial Sequence:
                        Syntheticpolynucleotide
source                  1..1701
                        mol_type = other DNA
                        organism = synthetic construct
SEQUENCE: 38
atggcaggca gacggcttac atggatcagc gagtttatcg taggtgccct ggactctgat    60
aagtacccct tggtaaaatg gcttgatcgg tcaacgggaa cttttctggc tcccgctgcg   120
agaaatgacg taataccact ggattccctg cagttttca tagattttaa gagggagtgt   180
ttgtcaaagg ggctccaccc ccgagatctt ttgggtagtc caataactgc gttcggtaag   240
atttgtacaa ctagccgacg gctgagacga ttgcccggtg aagagtacga agttgtccaa   300
ggaatcaact gccggcggtg gcggcttctc tgcgccgaag tgaaagaatg ctggtggtgt   360
gtacacgcgc aacacatctg cactccgga agcagccttt ggaaattct ctaccagcat   420
tccgtaagac ttgaaaagca ccgacgaagg cccaggccct tgtaggaga gaacagtgat   480
tcttctgagg aagaccccc tgctttctgc gatgtgcccg taacacaaac gggcgcggaa   540
agcgaggaca gcggcgatga aggtccttcc accagacaca gcgcctcagg tgtccaaccg   600
gtagacgatg ctaatgccga ctcccctggt tctggagacg aaggtccag cacccgccat   660
agcgacagtc aacctcctcc cgccgatgaa accactgtcc acacagacaa gtagaggac   720
gatttgacac tccttgataa agagtccgcg tgcgcattga gtgtatcacgt ggggcaggag   780
atggacatgc ttatgcgagc gatgtgcgat gaagacttgt tgatttgct tgggatccct   840
```

-continued

```
gaggatgtaa tagccacaag tcagcctggt ggtgatacgg acgcctctgg cgttgttacg    900
gagggtagta ttgctgctag cgccgtgggc gcagggggttg aagatgtcta cttggcagga   960
gccctcgaag cacagaatgt cgcaggggag tatgtgcttg agatctctga tgaggaagta   1020
gacgatggcg ctggactccc tcccgcctca aggcggagac ccgttgttgg agagttcttg   1080
tgggacgacg gtcctaggcg ccacgaaagg ccaacgacc gcagaattag gcacaggaaa   1140
ctcaggtctg cgtactacag agtagcacgg cccccagtga tgatcacgga caggctgggc   1200
gttgaggttt tttacttcgg aaggccggct atgagccttg aagtggaacg aaaagtattc   1260
atcttgtgta gccagaatcc gctggcagac atcagtcact cctgcctcca ttcacgaaaa   1320
gggcttcgag tcctgctgcc aaaaccggac gacaataata ctggtccggg agatgttaac   1380
ctcctcgcag cggtgttgag atcttttgca tcaggcttgg tgatagtctc actccgaagc   1440
ggaatctacg tgaagaacct ctgcaagagc accgtcctgt atcacggaaa caaccccca   1500
aaaaagtttg gcgttatatg cggactttca tccagagcag ttcttgacgt gtttaatgtt   1560
gcccaatacc ggattcaggg ccatgaacac atcaaaaaga caaccgtctt catcggggga   1620
gacccgactt cagcggagca atttgatatg gtgccactcg ttatcaagct tcggttgaga   1680
tcagtgacgt gcgacgatta a                                             1701

SEQ ID NO: 39          moltype = AA  length = 566
FEATURE                Location/Qualifiers
REGION                 1..566
                       note = Description of Artificial Sequence:
                       Syntheticpolypeptide
source                 1..566
                       mol_type = protein
                       organism = synthetic construct
SEQUENCE: 39
MAGRRLTWIS EFIVGALDSD KYPLVKWLDR STGTFLAPAA RNDVIPLDSL QFFIDFKREC    60
LSKGLHPRDL LGSPITAFGK ICTTSRRLRR LPGEEYEVVQ GINCRRWRLL CAEVKECWWC   120
VHARTHLHSG SSLWEILYQH SVRLEKHRRR PRPFVGENSD SSEEDHPAFC DVPVTQTGAE   180
SEDSGDEGPS TRHSASGVQP VDDANADSPG SGDEGPSTRH SDSQPPPADE TTVHTDNVED   240
DLTLLDKESA CALMYHVGQE MDMLMRAMCD EDLFDLLGIP EDVIATSQPG GDTDASGVVT   300
EGSIAASAVG AGVEDVYLAG ALEAQNVAGE YVLEISDEEV DDGAGLPPAS RRRPVVGEFL   360
WDDGPRRHER PTTRRIRHRK LRSAYYRVAR PPVMITDRLG VEVFYFGRPA MSLEVERKVF   420
ILCSQNPLAD ISHSCLHSRK GLRVLLPKPD DNNTGPGDVN LLAAVLRSFA SGLVIVSLRS   480
GIYVKNLCKS TVLYHGNNPP KKFGVICGLS SRAVLDVFNV AQYRIQGHEH IKKTTVFIGG   540
DPTSAEQFDM VPLVIKLRLR SVTCDD                                        566
```